United States Patent
Fukuda

(10) Patent No.: US 11,941,098 B2
(45) Date of Patent: Mar. 26, 2024

(54) AUTHENTICATION DEVICE, AUTHENTICATION SYSTEM, AUTHENTICATION METHOD, AND PROGRAM

(71) Applicant: NEC Corporation, Tokyo (JP)

(72) Inventor: Hiroshi Fukuda, Tokyo (JP)

(73) Assignee: NEC CORPORATION, Tokyo (JP)

(*) Notice: Subject to any disclaimer, the term of this patent is extended or adjusted under 35 U.S.C. 154(b) by 0 days.

(21) Appl. No.: 17/959,518

(22) Filed: Oct. 4, 2022

(65) Prior Publication Data

US 2023/0023622 A1 Jan. 26, 2023

Related U.S. Application Data

(63) Continuation of application No. 15/744,471, filed as application No. PCT/JP2016/069479 on Jun. 30, 2016, now Pat. No. 11,487,855.

(30) Foreign Application Priority Data

Jul. 15, 2015 (JP) ................. 2015-141177

(51) Int. Cl.
| | | |
|---|---|---|
| *G06F 21/32* | (2013.01) | |
| *A61B 5/117* | (2016.01) | |
| *G06T 1/00* | (2006.01) | |
| *G06V 10/147* | (2022.01) | |
| *G06V 40/13* | (2022.01) | |

(Continued)

(52) U.S. Cl.
CPC .............. *G06F 21/32* (2013.01); *A61B 5/117* (2013.01); *G06T 1/00* (2013.01); *G06V 10/147* (2022.01); *G06V 40/13* (2022.01); *G06V 40/145* (2022.01); *G06V 40/18* (2022.01); *G06V 40/67* (2022.01); *G06V 40/70* (2022.01); *G06F 2221/2111* (2013.01); *G06V 40/14* (2022.01)

(58) Field of Classification Search
None
See application file for complete search history.

(56) References Cited

U.S. PATENT DOCUMENTS 8,166,523 B2 4/2012 Ezaki et al.
8,996,726 B2 3/2015 Amano
(Continued)

FOREIGN PATENT DOCUMENTS

CN 104182871 12/2014 ......... G06Q 20/4014
JP 2002-244085 A 8/2002
(Continued)

OTHER PUBLICATIONS

Sesame ring (https://www.kickstarter.com/projects/1066401427/sesame-ring-where-will-it-take-you , 2014). (Year: 2014).*
(Continued)

*Primary Examiner* — Randolph I Chu
(74) *Attorney, Agent, or Firm* — Sughrue Mion, PLLC

(57) ABSTRACT

An authentication device includes: a wearing position determination unit that determines a wearing position, the wearing position being a position at which a wearable article comprising a sensor is being worn on a body; and an authentication unit that performs authentication by using biometric information of the body, the biometric information being detected by the sensor at the wearing position.

17 Claims, 27 Drawing Sheets

(51) Int. Cl.
*G06V 40/145* (2022.01)
*G06V 40/18* (2022.01)
*G06V 40/60* (2022.01)
*G06V 40/70* (2022.01)
*G06V 40/14* (2022.01)

(56) References Cited

U.S. PATENT DOCUMENTS

| | | | |
|---|---|---|---|
| 9,183,433 B2 | 11/2015 | Amano | |
| 9,594,427 B2 | 3/2017 | Priyantha | G06F 1/1698 |
| 9,711,060 B1 | 7/2017 | Lusted et al. | |
| 10,216,272 B2 | 2/2019 | Keller | H04B 10/114 |
| 10,281,953 B2 | 5/2019 | von Badinski et al. | |
| 10,310,632 B2 | 6/2019 | Nirjon | G06F 3/014 |
| 10,317,940 B2 | 6/2019 | Bim et al. | |
| 10,331,168 B2 | 6/2019 | von Badinski et al. | |
| 2003/0037264 A1 | 2/2003 | Ezaki et al. | |
| 2008/0247607 A1 | 10/2008 | Amano | |
| 2009/0282258 A1 | 11/2009 | Burke | G06F 21/46 |
| | | | 713/184 |
| 2010/0237990 A1 | 9/2010 | Amano et al. | |
| 2012/0075173 A1 | 3/2012 | Ashbrook | G06F 3/014 |
| | | | 345/156 |
| 2013/0183646 A1 | 7/2013 | Lusted et al. | |
| 2014/0193045 A1 | 7/2014 | Otis et al. | |
| 2014/0226872 A1 | 8/2014 | Amano | |
| 2014/0279528 A1* | 9/2014 | Slaby | G06F 1/163 |
| | | | 455/411 |
| 2015/0220109 A1 | 8/2015 | von Badinski et al. | |
| 2015/0277559 A1 | 10/2015 | Vescovi | G06F 3/016 |
| | | | 345/173 |
| 2015/0338926 A1* | 11/2015 | Park | G06F 3/005 |
| | | | 345/156 |
| 2016/0034742 A1 | 2/2016 | Kim | G06F 21/35 |
| | | | 382/124 |
| 2016/0077587 A1* | 3/2016 | Kienzle | G06F 3/033 |
| | | | 345/156 |
| 2016/0092665 A1 | 3/2016 | Cowan | G06F 21/32 |
| | | | 726/9 |
| 2016/0171201 A1 | 6/2016 | Schroder | H04B 5/0031 |
| | | | 726/20 |
| 2016/0213267 A1 | 7/2016 | Laakkonen | A61B 5/02433 |
| 2016/0350581 A1* | 12/2016 | Manuel | G06V 40/11 |
| 2017/0011210 A1 | 1/2017 | Cheong et al. | |
| 2017/0156036 A1 | 6/2017 | Laakkonen | A61B 5/6826 |
| 2017/0346635 A1 | 11/2017 | Gummeson | G06F 1/20 |
| 2017/0351346 A1* | 12/2017 | Hsieh | G06F 3/0346 |
| 2018/0120892 A1 | 3/2018 | von Badinski et al. | |
| 2018/0234415 A1* | 8/2018 | Fukuda | A61B 5/0062 |
| 2018/0342229 A1* | 11/2018 | Yan | G10H 1/344 |
| 2019/0086951 A1 | 3/2019 | von Badinski et al. | |
| 2019/0131812 A1 | 6/2019 | Lee et al. | |

FOREIGN PATENT DOCUMENTS

| | | | | |
|---|---|---|---|---|
| JP | 2003-58509 A | 2/2003 | | |
| JP | 2005-242907 A | 9/2005 | | |
| JP | 2006011614 A | 1/2006 | | |
| JP | 2008-257553 A | 10/2008 | | |
| JP | 2013-003075 A | 1/2013 | | |
| JP | 5598687 B2 | 10/2014 | | |
| JP | 2015-94961 A | 5/2015 | | |
| JP | 2015-185097 A | 10/2015 | | |
| JP | 2016-033815 A | 3/2016 | | |
| WO | WO-2014162296 A1 * | 10/2014 | | G06Q 20/102 |
| WO | WO-2016137514 A1 * | 9/2016 | | G06F 3/014 |

OTHER PUBLICATIONS

JP Office Action for JP Application No. 2021-129263, dated Aug. 2, 2022 with English Translation.
Japanese Office Action for JP Application No. 2019-187053 dated Jan. 5, 2021 with English Translation.
Communication dated Jul. 22, 2019, from the United States Patent and Trademark Office in U.S. Appl. No. 16/286,111.
Communication dated Jun. 25, 2019, from the Japanese Patent Office in counterpart Application No. 2017-528378.
Communication dated Apr. 3, 2019 from the United States Patent and Trademark Office in counterpart U.S. Appl. No. 16/286,111.
Communication dated Dec. 4, 2018, from Japanese Patent Office in counterpart application No. 2017-528378.
International Search Report for PCT/JP2016/069479 dated Sep. 27, 2016 [PCT/ISA/210].
And bgr.in, "Smart' ring sends phone updates to your finger", Dec. 2013, https://www.bgr.in/news/smart-ring-sends-phone-updates-to-your-finger-289407/ (Year: 2013).
U.S. Office Action for U.S. Appl. No. 15/744,471 dated Oct. 21, 2019.
U.S. Office Action for U.S. Appl. No. 15/744,471 dated Feb. 18, 2020.
U.S. Office Action for U.S. Appl. No. 15/744,471 dated Aug. 6, 2020.
U.S. Office Action for U.S. Appl. No. 15/744,471 dated Feb. 24, 2021.
U.S. Office Action for U.S. Appl. No. 15/744,471 dated Jul. 29, 2021.
U.S. Office Action for U.S. Appl. No. 15/744,471 dated Mar. 8, 2022.
U.S. Notice of Allowance for U.S. Appl. No. 15/744,471 dated Jul. 12, 2022.

* cited by examiner

AUTHENTICATION DEVICE, AUTHENTICATION SYSTEM, AUTHENTICATION METHOD, AND PROGRAM

CROSS-REFERENCE TO RELATED APPLICATIONS

The present application is a continuation application of U.S. patent application Ser. No. 15/744,471 filed on Jan. 12, 2018, which is a National Stage Entry of international application No. PCT/JP2016/069479 filed on Jun. 30, 2016, which claims the benefit of priority from Japanese Patent Application No. 2015-141177 filed on Jul. 15, 2015, the disclosures of all of which are incorporated in their entirety by reference herein.

TECHNICAL FIELD

The present invention relates to an authentication device, an authentication system, an authentication method and a program.

BACKGROUND ART

In biometric authentication technologies such as fingerprint authentication and vein authentication, the finger of an authentication subject must be appropriately placed on a placement surface on which the finger is to be placed, in order to allow the fingerprint or the vein pattern of the authentication subject to be collated with pre-registered authentication data.

For example, Patent Document 1 describes a biometric authentication method wherein a fingertip sensor for detecting misalignment of the finger placement position is provided on a tip placement surface of a tip placement portion on which the inside tip of a finger is to be placed, whereby misalignment of the inside tip of the finger is detected and the user is notified of misalignment of the finger placement position.

Additionally, in recent years, so-called wearable terminals, in which an information terminal is installed in a device that is worn on the body, such as a wristwatch, eyeglasses, a wristband or a finger ring (ring), have been provided. Wearable terminals often store information regarding the individual wearing that terminal, and mechanisms for authenticating whether or not they are being worn by the owner have been sought for security purposes.

Consider examples in which biometric authentication technologies are used in wearable terminals. For example, in the case of a wristwatch-type wearable terminal, an authentication method wherein a unit for fingerprint authentication is installed in the wearable terminal and fingerprint authentication is performed, for example, when a user places a finger on the display unit of the wristwatch, might be contemplated.

PRIOR ART DOCUMENTS

Patent Documents

[Patent Document 1]
Japanese Patent Publication No. 5598687

DISCLOSURE OF THE INVENTION

Problem to be Solved by the Invention

Many users feel that such wristwatch-type wearable terminals are too large and unwieldy to be worn on the body all of the time. For this reason, there has been a demand, from users, for more compact wearable terminals (e.g., ring-type wearable terminals) having an authentication function.

An exemplary object of the present invention is to provide an authentication device, a wearable article, a contact lens, a finger ring, an authentication system, an authentication method and a program that can solve one of the above-mentioned problems.

Means for Solving the Problem

An authentication device according to an exemplary aspect of the present invention includes: a wearing position determination unit that determines a wearing position, the wearing position being a position at which a wearable article including a sensor is being worn on a body; and an authentication unit that performs authentication by using biometric information of the body, the biometric information being detected by the sensor at the wearing position.

A wearable article according to an exemplary aspect of the present invention includes the above-mentioned authentication device.

A finger ring according to an exemplary aspect of the present invention includes the above-mentioned authentication device.

A contact lens according to an exemplary aspect of the present invention includes: a surface that is coated with a fluorescent coating; and the above-mentioned authentication device.

An authentication system according to an exemplary aspect of the present invention includes: the above-mentioned authentication device; and a display device that obtains, from the authentication device, information indicating the wearing position, and displays information for improving the wearing position based on the information indicating the wearing position.

An authentication system according to an exemplary aspect of the present invention includes: a wearable article including a sensor that detects the biometric information; and an information processing device including the above-mentioned authentication device.

An authentication method according to an exemplary aspect of the present invention includes: determining a wearing position, the wearing position being a position at which a wearable article including a sensor is being worn on a body; and performing authentication by using biometric information of the body, the biometric information being detected by the sensor at the wearing position.

A program according to an exemplary aspect of the present invention for causing a computer of an authentication device to execute: determining a wearing position, the wearing position being a position at which a wearable article including a sensor is being worn on a body; and performing authentication by using biometric information of the body, the biometric information being detected by the sensor at the wearing position.

Effect of the Invention

According to the present invention, it is possible to authenticate whether or not a person who is wearing a wearable article is the owner of that wearable article.

EMBODIMENTS FOR CARRYING OUT THE INVENTION

First Exemplary Embodiment

Herebelow, an authentication device according to a first exemplary embodiment of the present invention will be explained with reference to FIGS. 1 to 9.

Figure 1:
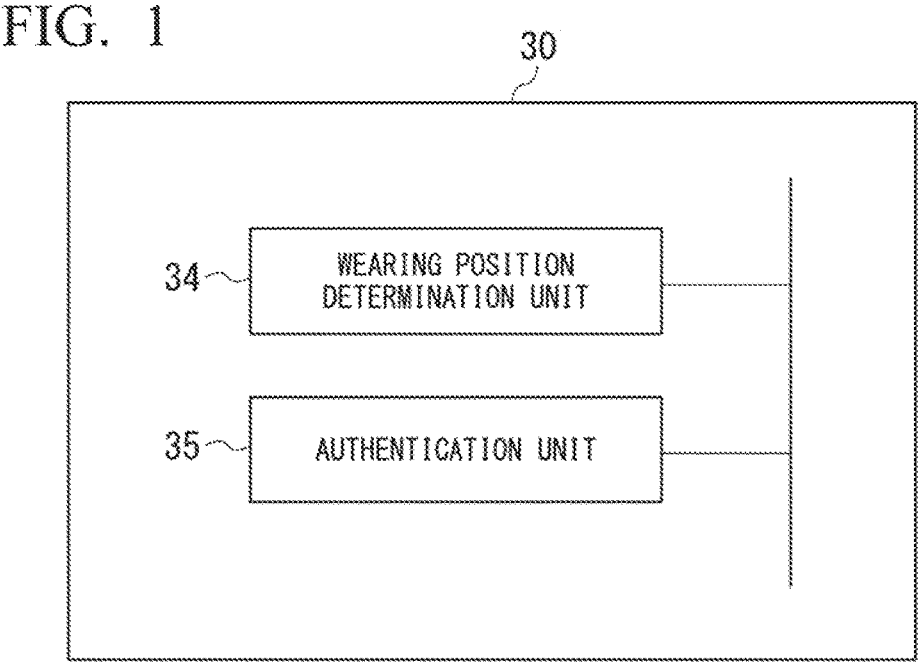
FIG. 1 is a diagram illustrating the structure of an authentication device according to a first exemplary embodiment of the present invention

FIG. 1 is a diagram illustrating the structure of an authentication device according to a first exemplary embodiment of the present invention.

As shown in FIG. 1, the authentication device 30 includes at least a wearing position determination unit 34 and an authentication unit 35.

The wearing position determination unit 34 determines the wearing position at which a wearable article, including an image sensor or the like, is worn on the body.

The authentication unit 35 performs authentication using biometric information from the body, detected by the sensor at the wearing position. The biometric information may, for example, be a vein pattern, an iris, a fingerprint, a skin wrinkle pattern or a facial image.

Figure 2:
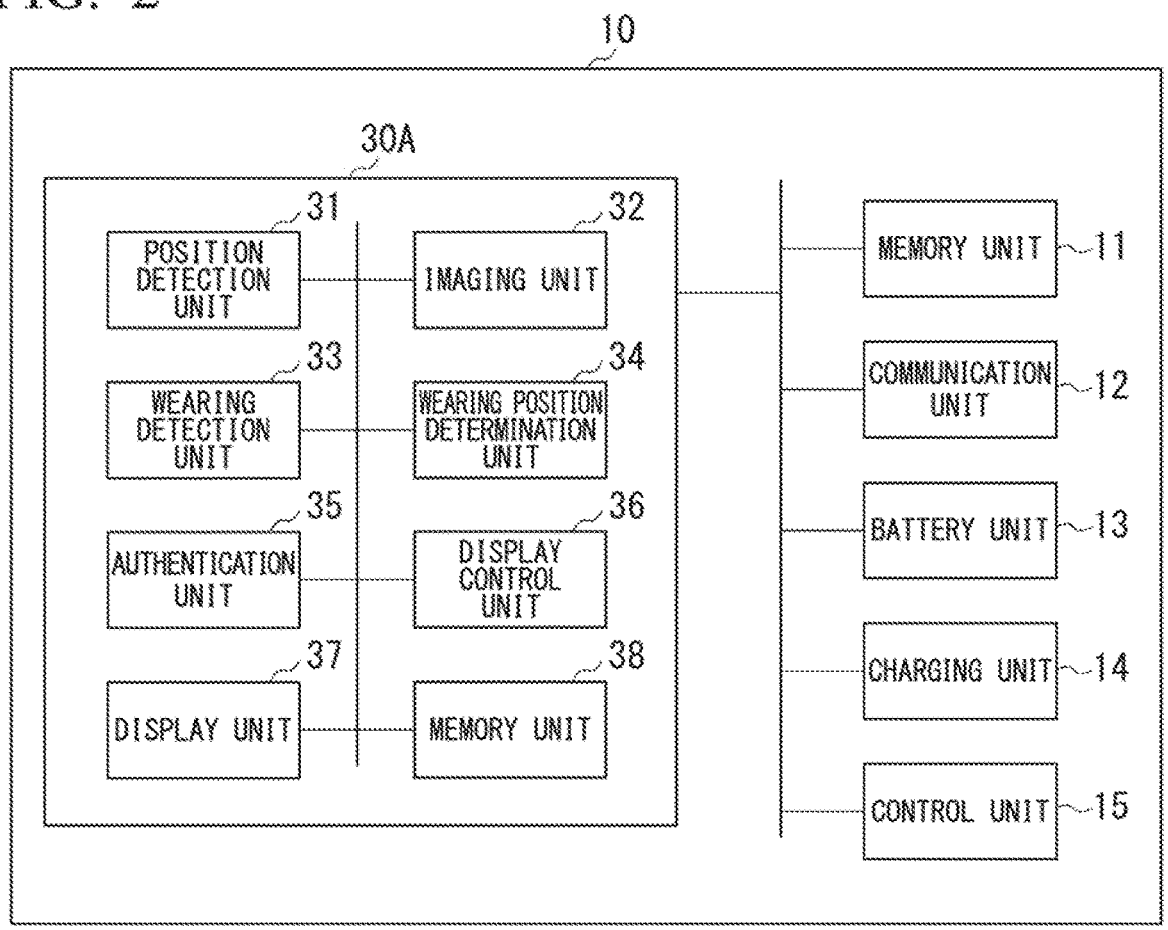
FIG. 2 is a diagram illustrating the authentication device according to the first exemplary embodiment of the present invention.

FIG. 2 is a diagram illustrating an authentication device according to a first exemplary embodiment of the present invention.

In FIG. 2, the wearable article 10 includes a memory unit 11, a communication unit 12, a battery unit 13, a charging unit 14, a control unit 15 and an authentication device 30A. The authentication device 30A includes a position detection unit 31, an imaging unit 32, a wearing detection unit 33, a wearing position determination unit 34, an authentication unit 35, a display control unit 36, a display unit 37 and a memory unit 38.

The wearable article 10 may, for example, be a wristwatch, a wristband, a finger ring (ring), eyeglasses, a contact lens, a necklace, clothing, shoes or socks. Personal information regarding the user owning the wearable article 10 is recorded in the wearable article 10. The user can make use of various services by using the wearable article 10, which is worn on the body instead of an IC (Integrated Circuit) card. For example, the user can use the wearable article 10 for personal identification when making use of payment services, riding on public transit systems, entering and exiting secured rooms and buildings, and participating in events or the like. Therefore, if the wearable article 10 were to be worn and used by another person, the privacy of a legitimate user could be violated, or the legitimate user could suffer economic and/or social harm. Therefore, an authentication device 30A is provided in the wearable article 10 to determine whether or not the person wearing the wearable article 10 is a legitimate user. If, as a result of authentication by the authentication device 30A, the person wearing the wearable article is found not to be a legitimate user, then the wearable article 10 suspends the functions that are used in payment services or the like. In the first exemplary embodiment, an example in which the wearable article 10 is a ring-type wearable terminal will be explained. Additionally, in the first exemplary embodiment, the authentication device 30A authenticates a legitimate user by means of vein authentication.

The memory unit 11 stores encrypted personal information for a legitimate user. The personal information may, for example, be identification information that is associated with the legitimate user. The identification information mentioned here may, for example, be information that is used to identify a user in various types of payment services, similar to the information that is recorded, for example, on an IC card.

The communication unit 12 communicates by means of short-range wireless communications such as NFC (Near Field Communications), for example, with an NFC card reader.

The battery unit 13 is a secondary battery that supplies electric power to the wearable article 10 and the authentication device 30A.

The charging unit 14 includes a power-receiving coil or the like. The charging unit 14 receives electric power transmitted, for example, from a power-transmitting coil of a non-contact charger, and stores the electric power in the battery unit 13.

The control unit 15 controls the actions of the wearable article 10. For example, when the user places the wearable article 10 near an NFC card reader, the authentication device 30A determines whether or not the user wearing the wearable article 10 is a legitimate user. If the authentication unit 30A determines that the user wearing the wearable article 10 is a legitimate user, the control unit 15 permits the personal information of the legitimate user, which is stored in the memory unit 11, to be transmitted by the communication unit 12, thereby enabling the use of payment services or the like.

The position detection unit 31 detects the wearing position at which the wearable article 10 is worn on the body. The position detection unit 31 may, for example, be an electrostatic capacitive sensor, a pressure sensor, a temperature sensor, an acceleration sensor, an image sensor or an ultrasonic sensor.

The imaging unit 32 captures an image including biometric information of the user relating to the wearing position at which the wearable article 10 is worn. The imaging unit 32 captures an image on the basis of the determination by the wearing position determination unit 34.

The wearing detection unit 33 detects the starting of a wearing action by which the user wears the wearable article 10.

When the wearing detection unit 33 detects that a wearing action has been started, the wearing position determination unit 34 determines whether or not the wearing position of the wearable article 10 is a position that is appropriate for capturing an image including biometric information for performing an authentication as to whether or not the user wearing the wearable article 10 is a legitimate user.

The authentication unit 35 collates an image captured by the imaging unit 32 at a position that is appropriate for capturing an image, as determined by the wearing position determination unit 34, with an image including biometric information of the legitimate user, which has been encrypted and registered beforehand. The authentication unit 35 authenticates whether or not the user wearing the wearable article 10 is a legitimate user based on the collation results.

The display control unit 36 controls information that is displayed on the display unit 37 based on the determination results of the wearing position determination unit 34 and the authentication results of the authentication unit 35.

The display unit 37 displays information that is presented to the user. The display unit 37 may, for example, be an LED (light emitting diode).

The memory unit 38 stores an image including the encrypted biometric information of the legitimate user and various types of information necessary for the authentication process.

Figure 3:
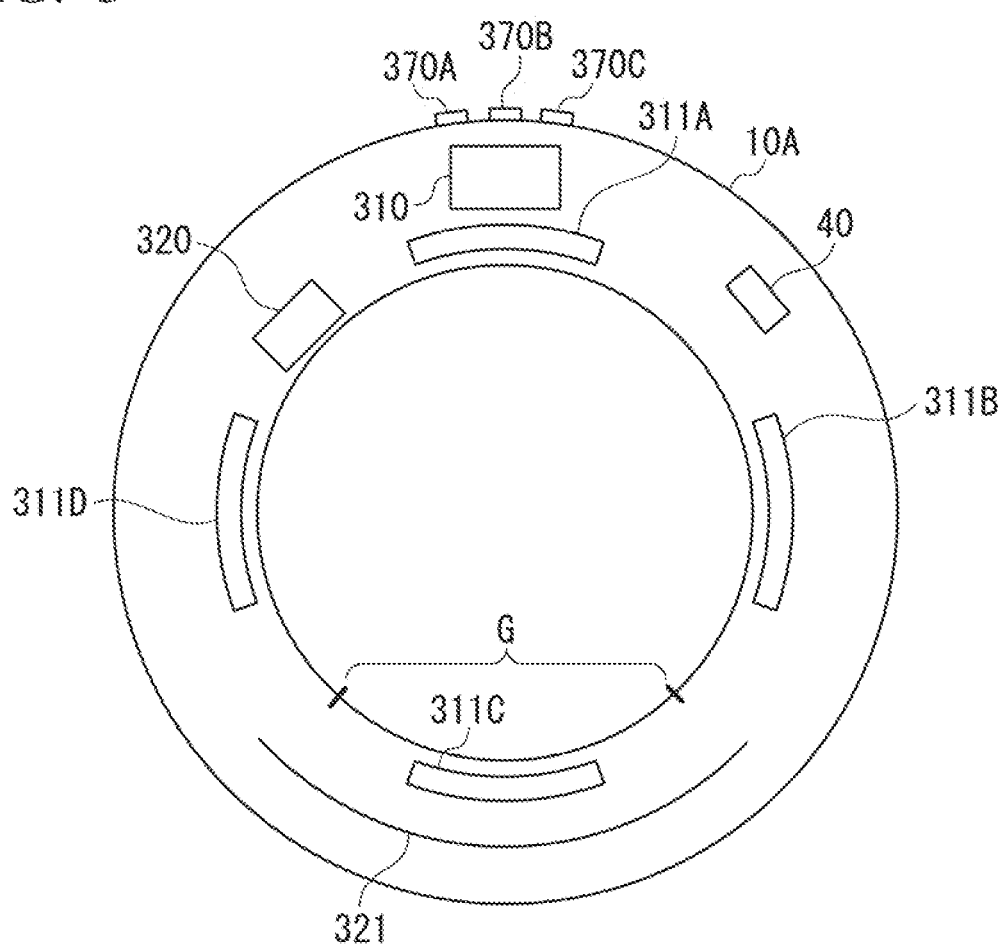
FIG. 3 is an example illustrating the specific structure of a wearable article according to the first exemplary embodiment of the present invention.

FIG. 3 illustrates an example of the specific structure of the wearable article 10A according to the first exemplary embodiment of the present invention.

FIG. 3 is a section view of a wearable article 10A (hereinafter referred to as ring 10A), which is a ring-type wearable terminal. The ring 10A includes an acceleration sensor 310, electrostatic capacitive sensors 311A to 311D, a light source 320, a TFT (Thin-Film Transistor) sensor (imaging element) 321, LED lamps 370A to 370C and a computation device 40. In addition thereto, the ring 10A includes features corresponding to the communication unit 12, the battery unit 13 and the like, which are omitted in the figure. As shown in FIG. 3, the electrostatic capacitive sensors 311A to 311D are provided at equidistant intervals on the cross-sectional circumference of the ring 10A. The electrostatic capacitive sensors 311A and 311C are disposed at positions that face each other in the vertical direction. The electrostatic capacitive sensors 311B and 311D are disposed at positions that face each other in the horizontal direction. The inner circumferential surface G of the ring 10A at the portion where the TFT sensor 321 is provided is covered with cover glass that transmits infrared light. The electrostatic capacitive sensor 311C is disposed at a position that is further towards the front side or towards the reverse side of the page surface, in the central axis direction, than the position at which the TFT sensor 321 is provided on the ring 10A, so as not to cross the propagation path of the infrared light received by the TFT sensor 321. The other electrostatic capacitive sensors 311A, 311B and 311D are also disposed at the same position as the electrostatic capacitive sensor 311C in the central axis direction. The inner circumference of the ring 10A is in the form of a perfect circle.

The acceleration sensor 310 detects the acceleration acting on the ring 10A. The acceleration sensor 310 may, for example, be a triaxial acceleration sensor. The electrostatic capacitive sensor 311A detects the distance between the electrostatic capacitive sensor 311A and the surface of the skin of the finger. The electrostatic capacitive sensors 311B to 311D are the same as the electrostatic capacitive sensor 311A. The acceleration sensor 310 and the electrostatic capacitive sensors 311A to 311D are an example of the position detection unit 31. The light source 320 emits infrared light. The TFT sensor 321 receives transmitted light after the infrared light has been scattered and transmitted through the finger. The TFT sensor 321 converts the received transmitted light to an electric signal and generates an image. The vein pattern at the position at which the ring 10A is worn appears in the image generated by the TFT sensor 321. The light source 320 and the TFT sensor 321 are an example of the imaging unit 32. The LED lamps 370A to 370C indicate, to the user, the wearing position determination results and the authentication results from vein authentication. For example, the LED lamps 370A to 370C emit light based on an instruction signal from the display control unit 36. The LED lamps 370A to 370C may, for example, turn on when the authentication succeeds and blink when the authentication fails. As a separate method, the LED lamps 370A to 370C may, for example, be LEDs that emit both red light and green light, and may turn green when the authentication succeeds and turn red when the authentication fails. The LED lamps 370A to 370C are an example of the display unit 37. The computation device 40 may, for example, be a computer device including a CPU (Central Processing Unit). The computation device 40 includes a memory unit, and by reading out and executing programs stored in the memory unit, performs the functions of the wearing detection unit 33, the wearing position determination unit 34, the authentication unit 35 and the display control unit 36.

Figure 4:
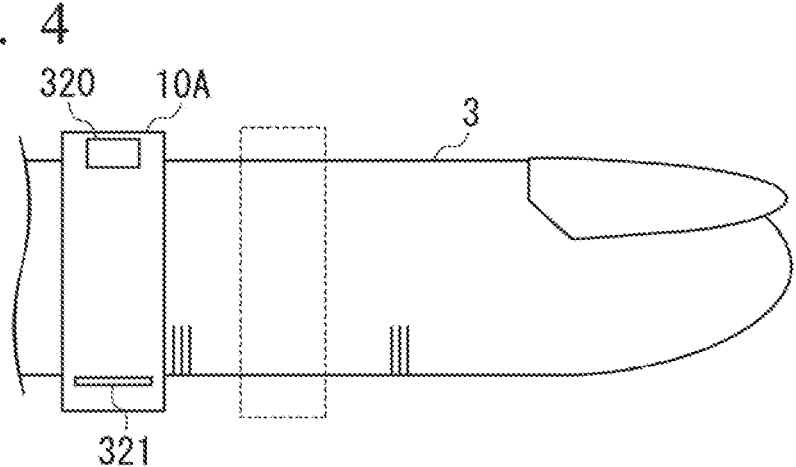
FIG. 4 is a first diagram for explaining the authentication method according to the first exemplary embodiment of the present invention.

FIG. 4 is a first diagram for explaining the authentication method according to the first exemplary embodiment of the present invention.

FIG. 4 shows the ring 10A as worn on the finger 3 of a user. In the present exemplary embodiment, vein authentication is performed by using an image including a vein pattern that can be detected while the ring 10A is worn at a predetermined position. The predetermined position may, for example, be a position at which the ring 10A is always worn. Therefore, there is a possibility that the authentication will not succeed if authentication is performed, for example, while the ring 10A is at the position indicated by the dashed lines.

Thus, in the present exemplary embodiment, by using, for example, detection results from the acceleration sensor 31, the wearing position determination unit 34 determines whether or not the ring 10A is being worn at the position where authentication is to be performed. Specifically, the wearing position determination unit 34 computes the distance from the position at which the starting of the wearing action of the ring 10A was detected to the position at which the completion of the wearing action of the ring 10A was detected, and the determination is made by using this distance. The position of the ring 10A in the insertion direction will be referred to as the lateral position. Next, the computation of the lateral position will be explained by referring to FIG. 5.

Figure 5:
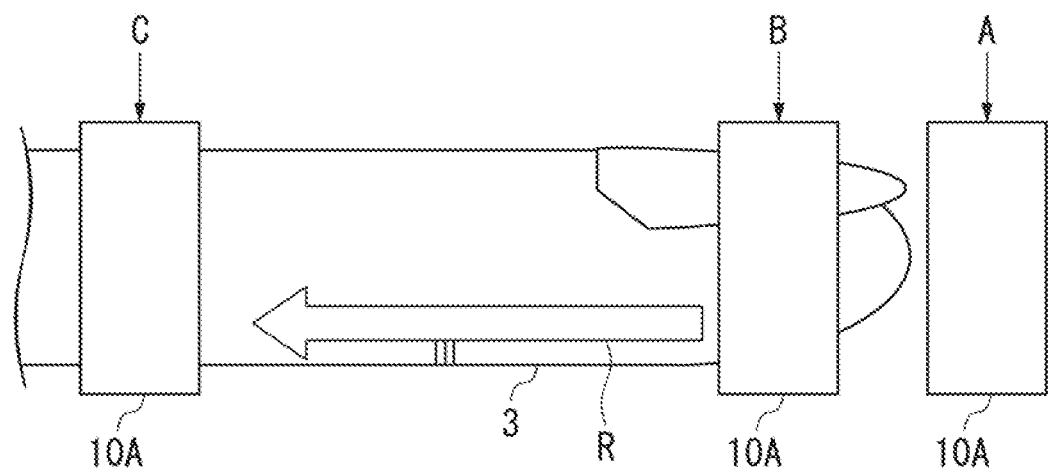
FIG. 5 is a second diagram for explaining the authentication method according to the first exemplary embodiment of the present invention.

FIG. 5 is a second diagram for explaining the authentication method in the first exemplary embodiment of the present invention.

A user puts the ring 10A on the finger 3 by moving it in the direction of the arrow R. The case in which, at this time, the ring 10A is to be worn with the side provided with the LED lamps 370A to 370C facing upwards and the back of the hand facing upwards will be explained. Each of the electrostatic capacitive sensors 311A to 311D outputs, to the wearing detection unit 33, information indicating the detected distance between itself and a target. For example, when the ring 10A is at position A, the electrostatic capacitive sensors 311A to 311D do not detect any significant values indicating that the ring 10A is being worn on the finger 3. Next, when the ring 10A moves to position B, the electrostatic capacitive sensor 311A detects the distance between the electrostatic capacitive sensor 311A and the surface of the finger 3. The electrostatic capacitive sensor 311A outputs the detected distance information to the wearing detection unit 33. Similarly, each of the electrostatic capacitive sensors 311B to 311D outputs, to the wearing detection unit 33, information regarding the detected distance between itself and the surface of the finger. Based on information obtained from the electrostatic capacitive sensors 311A to 311D, the wearing detection unit 33 determines whether or not the ring 10A has reached a predetermined position on the finger 3 (for example, near the tip of the finger 3). For example, when the distance information obtained by all of the electrostatic capacitive sensors 311A to 311D indicates a value that is within a predetermined range indicating that the ring 10A is being worn on the finger 3, the wearing detection unit 33 outputs, to the wearing position determination unit 34, a detection signal indicating that the insertion of the ring 10A has started.

Upon obtaining the detection signal, the wearing position determination unit 34 starts measuring the distance of movement of the ring 10A by means of the acceleration sensor 310. Specifically, the wearing position determination unit 34 obtains acceleration information from the acceleration sensor 310 at predetermined intervals in time, and thereby computes the movement distance.

When the wearing action by the user stops and the acceleration detected by the acceleration sensor 310 becomes a predetermined value (e.g., zero), the wearing position determination unit 34 determines whether or not the lateral position of the ring 10A is a predetermined lateral position. Specifically, the wearing position determination unit 34 reads, from the memory unit 38, predetermined distance information (determination criteria values) corresponding to the values when the user is wearing the ring 10A at the authentication position. The wearing position determination unit 34 compares the computed movement distance with the predetermined distance that has been read out. If the computed movement distance is equal to the predetermined distance that has been read out (or if the computed movement distance is a value that is within a certain range including the predetermined distance), the wearing position determination unit 34 determines that the ring 10A is at the predetermined lateral position. If the computed movement distance is not equal to the predetermined distance that has been read out (or if the computed movement distance is not a value that is within a certain range including the predetermined distance), the wearing position determination unit 34 determines that the ring 10A is not at the predetermined lateral position. Additionally, the wearing position determination unit 34 calculates the difference between the computed movement distance and the predetermined distance that has been read out. The wearing position determination unit 34 outputs, to the display control unit 36, the determination result and information regarding the calculated difference in the distance.

The display control unit 36 generates a display corresponding to the obtained determination result, using the LED lamps 370A to 370C. When, for example, the ring 10A is at a predetermined lateral position, the display control unit 36 blinks the LED lamp 370B once in order to indicate that the lateral position is appropriate. When, for example, the ring 10A is not at the predetermined lateral position and the computed movement distance is less than the predetermined distance that has been read out, the display control unit 36 blinks the LED lamp 370A once. When, for example, the computed movement distance exceeds the predetermined distance that has been read out, the display control unit 36 blinks the LED lamp 370C once. As a result thereof, the user can understand whether or not the movement distance of the ring 10A is appropriate. Furthermore, when the movement distance of the ring 10A is not appropriate, the user is able to understand whether the movement amount is too little or too much. The user refers to this display to adjust the lateral position of the ring 10A to a position that is appropriate for authentication. When the user adjusts the lateral position of the ring 10A, and for example, the acceleration detected by the acceleration sensor 310 is indicated to be a predetermined value (e.g., zero), the wearing position determination unit 34 performs lateral position determination once again. By repeatedly making such adjustments, it is possible to correct the misalignment of the lateral position of the ring 10A so as to be at a position that is appropriate for authentication.

Figure 6A:
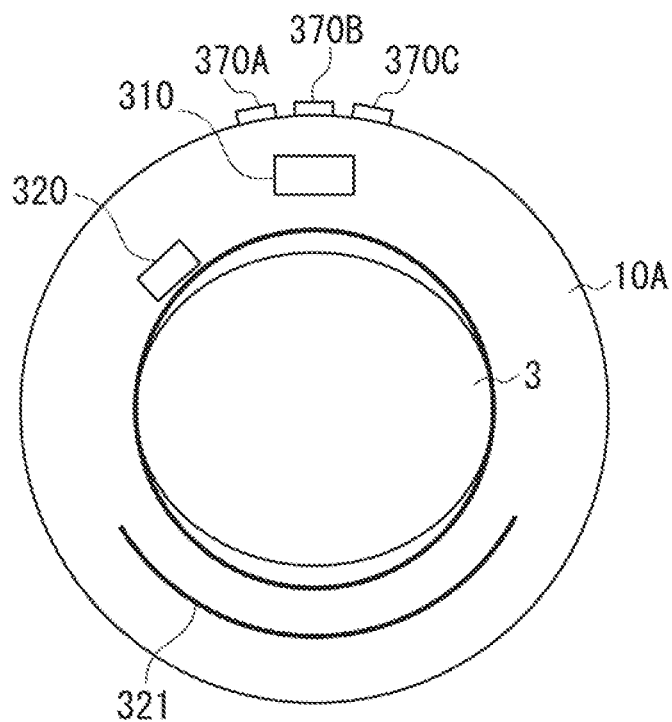
FIG. 6A is a third diagram for explaining the authentication method according to the first exemplary embodiment of the present invention.
Figure 6B:
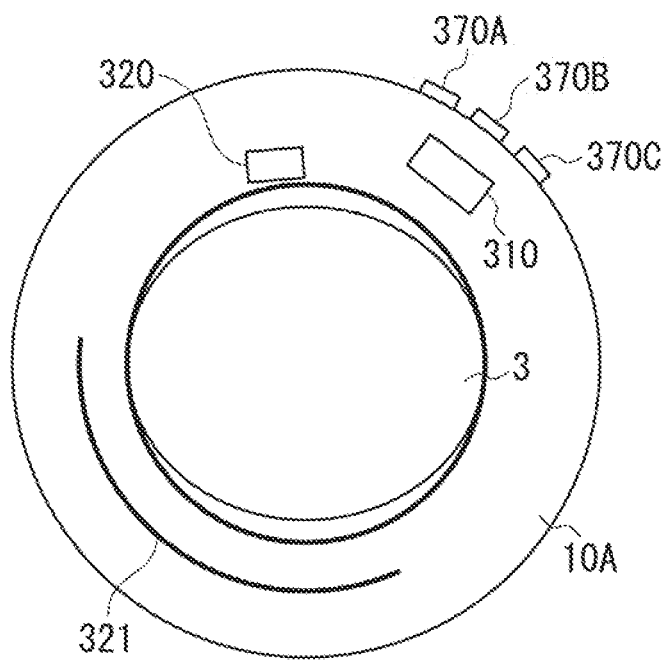
FIG. 6B is a third diagram for explaining the authentication method according to the first exemplary embodiment of the present invention.

FIGS. 6A and 6B are third diagrams for explaining the authentication method according to the first exemplary embodiment of the present invention.

FIGS. 6A and 6B are section views of the ring 10A being worn by a user, as seen from the fingertip direction. In the example in FIG. 6A, the user is wearing the ring 10A so that the side on which the LED lamps 370A to 370C are provided faces upwards and the back of the hand faces upwards. In the example in FIG. 6B, the user is wearing the ring 10A with the LED lamps 370A to 370C facing diagonally upwards and the back of the hand facing upwards. When performing vein authentication using an authentication image (an image including the vein pattern of a legitimate user, pre-registered in the memory unit 38) captured with the finger 3 and the ring 10A in the positional relationship shown in FIG. 6A, there is a possibility that the authentication will not succeed even when vein authentication is performed by collation with an image captured by the imaging unit 32 when, for example, the finger 3 and the ring 10A are in the positional relationship shown in FIG. 6B.

Therefore, in the present exemplary embodiment, in addition to the lateral position of the ring 10A, the wearing position determination unit 34 also detects the direction in which the image including the vein pattern is captured. The wearing position determination unit 34 determines whether or not the position of the ring 10A, in the direction of rotation about the central axis, when the ring 10A is worn, is a position in which authentication is to be performed. Next, the computation of the rotation direction position will be explained by using FIGS. 7A, 7B, 8A and 8B.

Figure 7A:
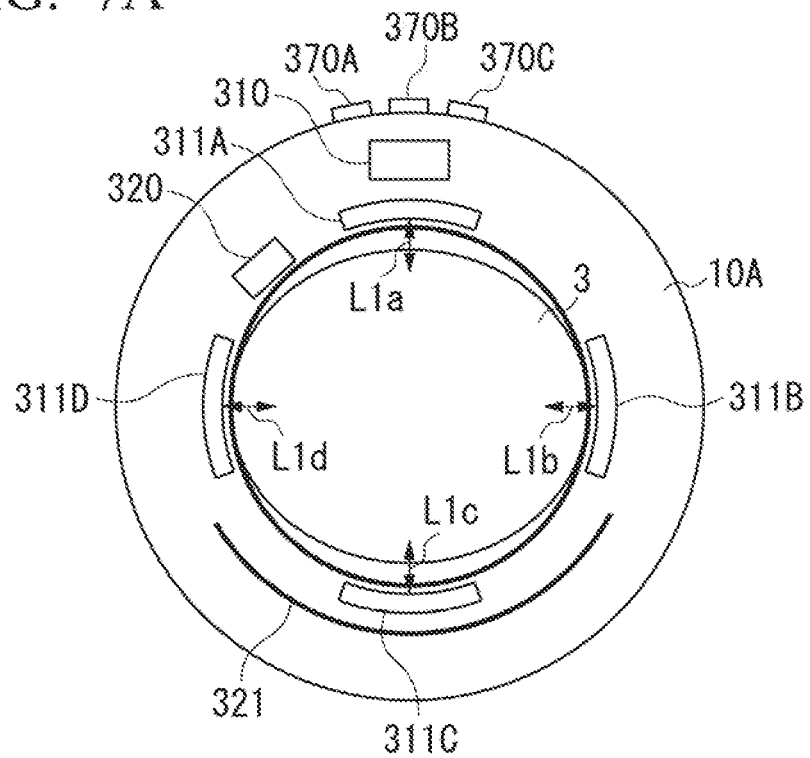
FIG. 7A is a fourth diagram for explaining the authentication method according to the first exemplary embodiment of the present invention.
Figure 7B:
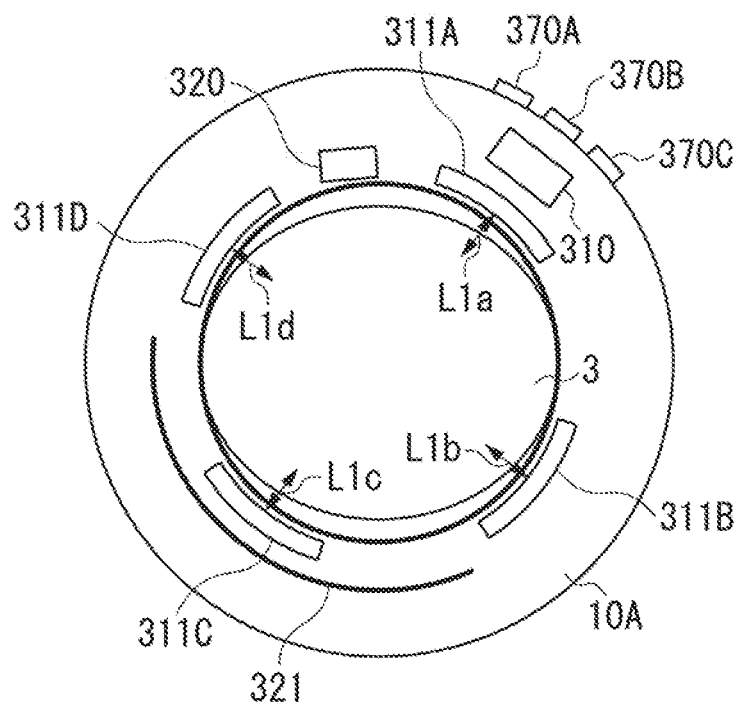
FIG. 7B is a fourth diagram for explaining the authentication method according to the first exemplary embodiment of the present invention.

FIGS. 7A and 7B are fourth diagrams for explaining the authentication method according to the first exemplary embodiment of the present invention.

FIGS. 7A and 7B are section views of the ring 10A being worn by a user, when viewed from the fingertip direction. In the examples in FIGS. 7A and 7B, the back of the user's hand is facing upwards. In the example in FIG. 7A, the user is wearing the ring 10A so that the side provided with the LED lamps 370A etc. is facing upwards. In the example in FIG. 7B, the user is wearing the ring 10A on the finger 3 so that the LED lamps 370A etc. are facing diagonally upwards (e.g., diagonally 45°).

In general, the cross-section of a user's finger 3 will often form an approximate ellipse. Accordingly, when the ring 10A is worn, the side portions of the finger make contact with the inner circumferential surface of the ring 10A, and gaps are formed between the upper and lower surface of the finger and the inner circumferential surface of the ring 10A, as shown in FIG. 7A. The distance between the electrostatic capacitive sensor 311A and the finger is indicated as L1$a$, and the distance between the electrostatic capacitive sensor 311B and the finger is indicated as L1$b$. Additionally, the distance between the electrostatic capacitive sensor 311C and the finger is indicated as L1$c$, and the distance between the electrostatic capacitive sensor 311D and the finger is indicated as L1$d$. In this case, in the situation shown in FIG. 7A, L1$a$ and L1$c$ are greater than L1$b$ and L1$d$. On the other hand, in the situation shown in FIG. 7B, L1$a$, L1$b$, L1$c$ and L1$d$ are each about the same. Thus, it is possible to detect the rotation direction position of the ring 10A by making use of the fact that, between the finger 3, which has an elliptical cross-section, and the ring 10A, which has a perfectly circular inner circumference, there are portions in which gaps are formed and portions in which there is close contact. The wearing position determination unit 34 determines whether or not the rotation direction position of the ring 10A is a position that is appropriate for authentication, based on the distances between the finger 3 and the electrostatic capacitive sensors 311A to 311D provided in the ring 10A.

Figure 8A:
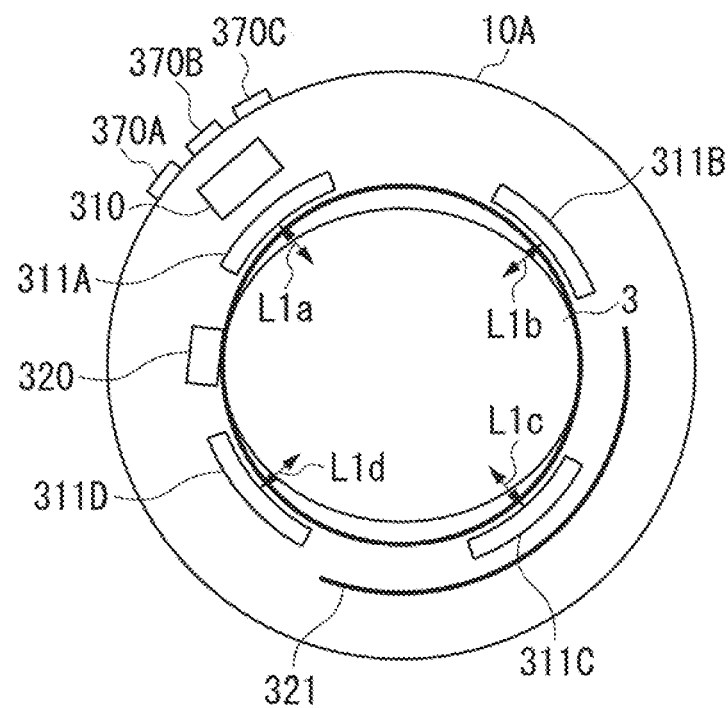
FIG. 8A is a fifth diagram for explaining the authentication method according to the first exemplary embodiment of the present invention.
Figure 8B:
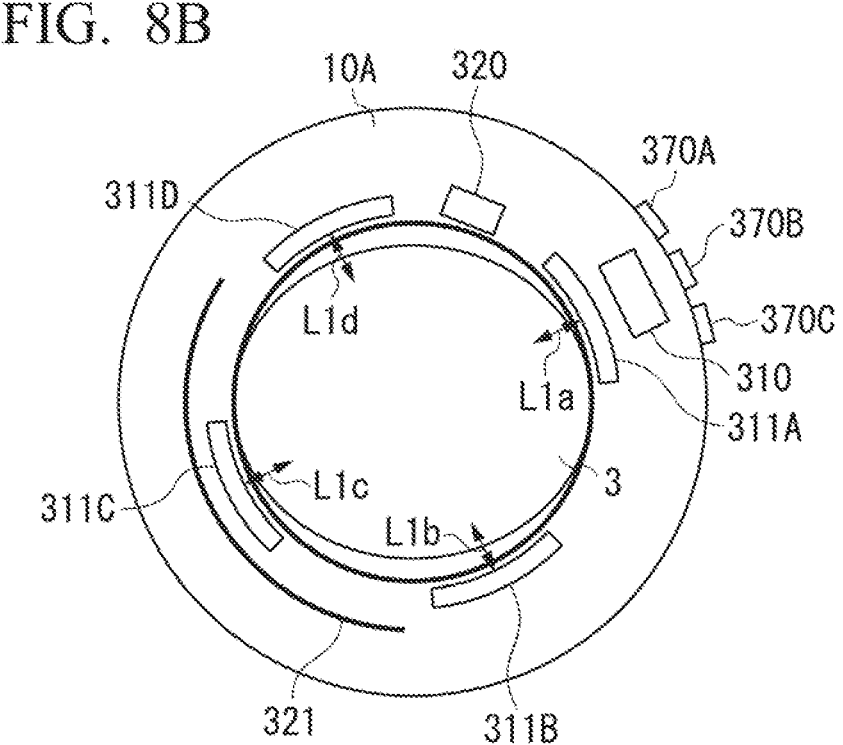
FIG. 8B is a fifth diagram for explaining the authentication method according to the first exemplary embodiment of the present invention.

FIGS. 8A and 8B are fifth diagrams for explaining the authentication method according to the first exemplary embodiment of the present invention.

FIG. 8A is a diagram illustrating the case in which the ring 10A is worn so as to be tilted (rotated) by 45° in the direction opposite to that in FIG. 7B, using the case illustrated in FIG. 7A as the standard.

In the case of FIG. 8A, L1$a$, L1$b$, L1$c$ and L1$d$ are all about the same, as in the case shown in FIG. 7B. Additionally, L1$a$ and L1$b$ in FIG. 8A are about the same as L1$a$ and L1$b$ in FIG. 7B. Therefore, when considering only the distances from the finger 3 detected by the electrostatic capacitive sensors 311A to 311D, there is a possibility that the wearing position determination unit 34 will not be able to determine whether the rotation direction position of the ring 10A is tilted to the right (FIG. 7B) or tilted to the left (FIG. 8A). Therefore, the wearing position determination unit 34 determines the tilt direction of the ring 10A based on the direction of acceleration detected by the acceleration sensor 310 at the rotation direction position at which authentication is to be performed (the state shown in FIG. 7A), as stored in the memory unit 38. For example, the memory unit 38 may record coordinate information (coordinate information 1) for the acceleration direction detected by the acceleration sensor 310 in the state shown in FIG. 7A. The wearing position determination unit 34 obtains, from the acceleration sensor 310, coordinate information (coordinate information 2) for the acceleration direction detected by the acceleration sensor 310, for example, in the state shown in FIG. 8A. The wearing position determination unit 34 uses the coordinate information 1 and the coordinate information 2 to calculate the angle between the vector indicated by coordinate information 1 and the vector indicated by coordinate information 2. As a result thereof, the wearing position determination unit 34 can determine in which direction and by how much the ring 10A, in the state shown in FIG. 8A, is tilted from the rotation direction position at which authentication is to be performed. The tilt of the ring 10A can also be detected by using a gyrosensor.

The rotation direction position at which vein authentication is to be performed is set to be the position when the side of the ring 10A on which the LED lamps 370A etc. are provided is facing upwards and the back of the hand is facing upwards. In this case, the situation in which the user puts on the ring 10A in a tilted state will be explained. In this case, first, the wearing position determination unit 34 reads, from the memory unit 38, the distances (determination criteria values) between the electrostatic capacitive sensors 311A to 311D and the finger 3 when the ring 10A is at the rotation direction position at which vein authentication is to be performed. Regarding these values stored by the memory unit 38, for example, the distance between the electrostatic capacitive sensor 311A and the finger 3 and the distance between the electrostatic capacitive sensor 311C and the finger 3 are set to be Ly, and the distance between the electrostatic capacitive sensor 311B and the finger 3 and the distance between the electrostatic capacitive sensor 311D and the finger 3 are set to be Lx (e.g., Lx=0). The wearing position determination unit 34 compares these values that have been read out with L1a, L1b, L1c and L1d as detected by the electrostatic capacitive sensors 311A to 311D. If, for example, L1a and L1c are not values within a predetermined range that can be considered to be approximately Ly, then the wearing position determination unit 34 determines that the rotation direction position of the ring 10A is not the position at which authentication is to be performed. Next, by using a value detected by the acceleration sensor 310, the wearing position determination unit 34 determines the side to which the ring 10A is tilted with respect to the rotation direction position at which authentication is to be performed. The wearing position determination unit 34 outputs the determination results to the display control unit 36.

The display control unit 36 uses the LED lamps 370A to 370C to generate a display corresponding to the obtained determination results. If, for example, the ring 10A is at the position at which authentication is to be performed, the display control unit 36 blinks the LED lamp 370B twice. If, for example, the ring 10A is tilted to the right when facing the page surface, the display control unit 36 blinks the LED lamp 370A twice to indicate the direction in which the tilt should be corrected. Conversely, if the ring 10A is tilted to the left when facing the page surface, the display control unit 36 blinks the LED lamp 370C twice. The user adjusts the rotation direction position of the ring 10A to a position appropriate for authentication in response to these displays.

FIG. 8B is a diagram illustrating the situation when the ring 10A is tilted further to the right, when facing the page surface, from the state shown in FIG. 7B. In this case, due to the above-mentioned process, the display control unit 36 blinks the LED lamp 370A twice. The user adjusts the rotation direction position by rotating the ring 10A to the left, when facing the page surface, in response to the display. For example, comparing the value of L1a in the state shown in FIG. 7B with the value of L1a in the state shown in FIG. 8B, the value of L1a in FIG. 7B is larger than the value of L1a in FIG. 8B. In other words, when the user rotates the ring 10A to the left, when facing the page surface, from the state shown in FIG. 8B, the value of L1a becomes gradually larger until the electrostatic capacitive sensor 311A reaches the position at which authentication is to be performed. Similarly, regarding the value of L1d, the value of L1d becomes gradually smaller until the electrostatic capacitive sensor 311D reaches the position at which authentication is to be performed. In this way, by monitoring the change in the distance between the electrostatic capacitive sensors 311A to 311D within the range of a rotational angle of 90° with respect to the rotation direction position at which authentication is to be performed, the wearing position determination unit 34 is able to determine the direction of rotation of the ring 10A by the user.

After determining that the ring 10A is tilted to the right when facing the page surface, the wearing position determination unit 34 may, for example, continue to monitor the value of L1a as the value of L1a gradually increases. As long as the value is less than Ly, it is determined that the ring 10A is still tilted to the right. In this case, the display control unit 36 blinks the LED lamp 370A twice. Additionally, if the value of L1a gradually increases, reaches Ly, then becomes gradually smaller, then the wearing position determination unit 34 determines that the user has rotated the ring 10A past the position at which authentication is to be performed. In this case, the display control unit 36 blinks the LED lamp 370C twice. In this way, the wearing position determination unit 34 determines the rotation direction position of the ring 10A, and the display unit displays the result thereof, thereby allowing the user to correct misalignment of the rotation direction position of the ring 10A so as to be at a position that is appropriate for authentication.

Figure 9:
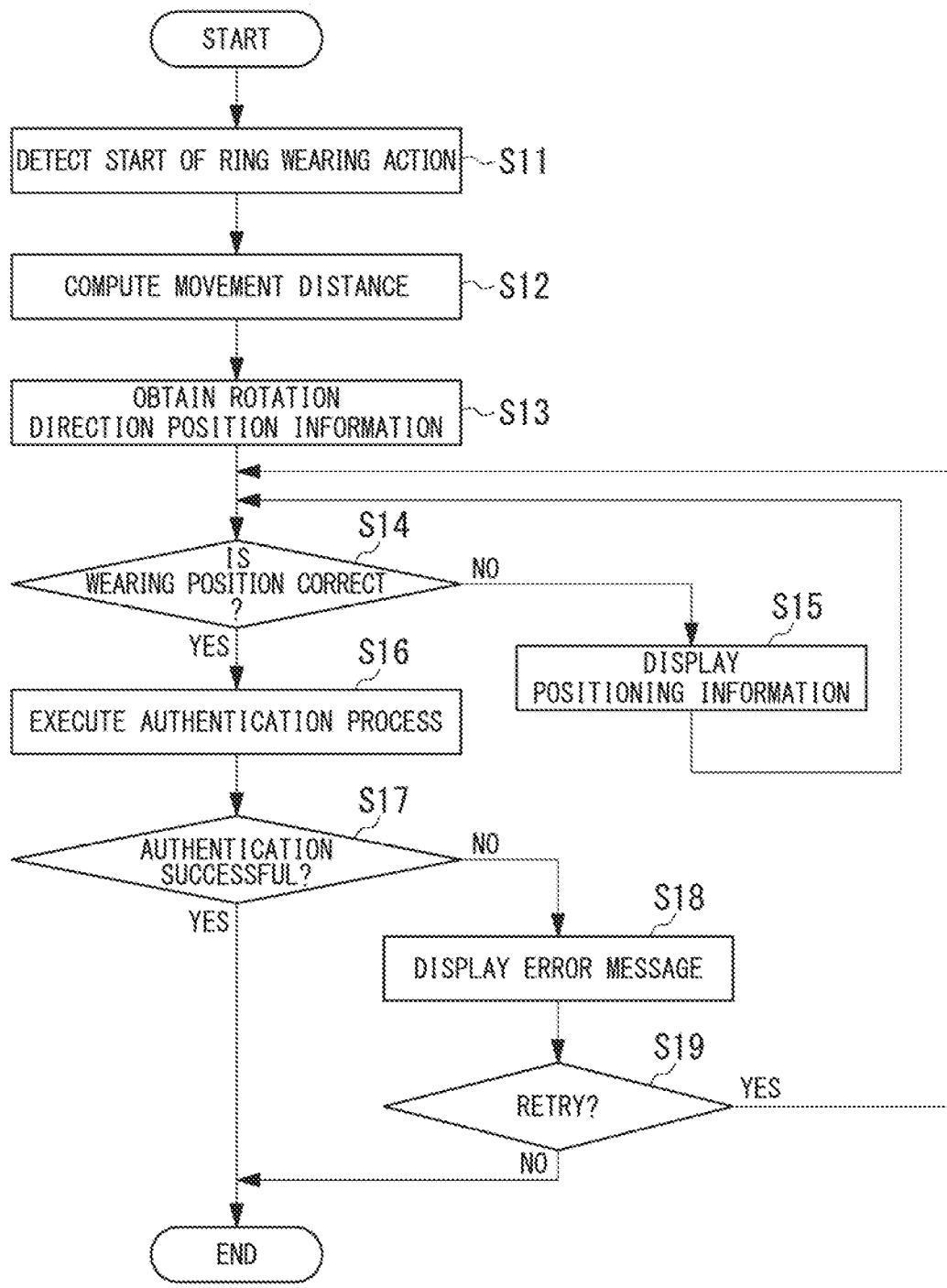
FIG. 9 is a flow chart illustrating an example of the authentication method according to the first exemplary embodiment of the present invention.

FIG. 9 is a flow chart showing an example of the authentication method according to the first exemplary embodiment of the present invention.

The explanation will center on the processing flow for aligning the ring 10A with a position appropriate for vein authentication, by referring to FIG. 9.

It is assumed that the method for putting on the ring 10A is described in a manual or the like for the ring 10A, and that the user is to put on the ring 10A in accordance with said method. The manual for the ring 10A may, for example, include instructions to put on the ring 10A by keeping the movement direction horizontal, with the side provided with the LED lamps 370A etc. facing upwards. Additionally, the manual of the ring 10A may provide instructions that the user should put on the ring 10A with the back of the hand facing upwards.

First, the user starts to put the ring 10A on the finger 3. When the ring 10A starts to be put on the finger 3, each of the electrostatic capacitive sensors 311A to 311D detects the distance to the finger 3 and outputs the distance information to the wearing detection unit 33. The wearing detection unit 33 detects the starting of a wearing action for wearing the ring 10A on the finger 3 based on the distance information obtained from the electrostatic capacitive sensors 311A to 311D (step S11). For example, the wearing detection unit 33 detects the starting of a wearing action when all of the obtained distance information becomes a value that is within a predetermined range. Then, the wearing detection unit 33 outputs, to the wearing position determination unit 34, a signal indicating that the wearing action has started. The horizontal position of the ring 10A when the wearing detection unit 33 detects that the wearing action has started is the above-mentioned "predetermined position on the finger 3". Upon obtaining the signal indicating that the wearing action has started, the wearing position determination unit 34 starts to obtain acceleration information from the acceleration sensor 310. The user moves the ring 10A to the predetermined wearing position and temporarily halts the wearing action.

When the movement of the ring 10A stops, the wearing position determination unit 34 uses acceleration information, which has been obtained at predetermined intervals in time, to calculate the movement distance in the horizontal direction (step S12).

Additionally, the wearing position determination unit 34 obtains rotation direction position information (step S13). Specifically, the wearing position determination unit 34 obtains, from each of the electrostatic capacitive sensors 311A to 311D, information regarding the distance between the electrostatic capacitive sensors 311A to 311D and the finger 3. Additionally, the wearing position determination unit 34 obtains information indicating the tilt of the ring 10A from the acceleration sensor 310.

Next, the wearing position determination unit 34 determines whether or not the wearing position of the ring 10A is correct (step S14). The wearing position determination unit 34 reads, from the memory unit 38, a determination criterion value for the movement distance of the ring 10A, and compares the determination criterion value that has been read out with the horizontal movement distance computed in step S12. Additionally, the wearing position determination unit 34 reads, from the memory unit 38, determination criteria values for the distances between each electrostatic capacitive sensor 311A to 311D and the finger 3, and compares the determination criteria values that have been read out with the distance information obtained from the electrostatic capacitive sensors 311A to 311D in step S13. If the horizontal movement distance and the distances between each of the electrostatic capacitive sensors 311A to 311D and the finger 3 are all equal to the determination criteria values that are set therefor (or if the distances are within the range that can be considered to be equivalent), then the wearing position determination unit 34 determines that the wearing position of the ring 10A is correct (at the position at which authentication is to be performed). If that is not the case, then the wearing position determination unit 34 determines that the wearing position of ring 10A is not correct. In other words, if at least one of the horizontal movement distance and the distances between each of the electrostatic capacitive sensors 311A to 311D and the finger 3 is not equal to the set determination criterion value, then the wearing position determination unit 34 determines that the wearing position of the ring 10A is not correct. If the wearing position determination unit 34 determines that the wearing position of the ring 10A is not correct (step S14: No), then the wearing position determination unit 34 outputs, to the display control unit 36, information regarding the differences between the determination criteria values and the values indicating the wearing position of the ring 10A. The display control unit 36 displays, on the display unit 37, positioning information for improving the wearing position (step S15). For example, if the horizontal movement distance is misaligned, the wearing position determination unit 34 outputs, to the display control unit 36, a value obtained by subtracting the computed movement distance from the determination criterion value of the movement distance.

If the obtained value is a positive value, then the display control unit 36 blinks the LED lamp 370A once. The process is similar when the rotational position is misaligned. The user adjusts the position of the ring 10A by referring to this positioning information. The wearing position determination unit 34 repeats the process, starting at step S14, for determining whether or not the ring 10A, after the positional adjustment, is at the correct position that is appropriate for authentication.

If the wearing position determination unit 34 determines that the wearing position is correct (step S14: Yes), the wearing position determination unit 34 outputs, to the authentication unit 35, a signal providing instructions to perform an authentication process. Next, the authentication unit 35 executes the authentication process (step S16). The authentication unit 35 instructs the imaging unit 32 (light source 320 and TFT sensor 321) to capture an image. The authentication unit 35 obtains the image captured by the imaging unit 32. The authentication unit 35 reads, from the memory unit 38, an image (authentication image) including the vein pattern of a legitimate user. The authentication unit 35 collates the image that has been read out with the image currently captured by the imaging unit 32. If the similarity between the two images is higher than a predetermined threshold value, then the authentication unit 35 determines that the authentication has succeeded. If the authentication succeeds (step S17: Yes), then the processing flow ends. Furthermore, the authentication unit 35 outputs the authentication result to the control unit 15. Based on the authentication result, the control unit 15 enables functions using various services making use of personal information stored in the memory unit 11. The user is then able to make use of payment services and the like using the ring 10A.

If the authentication fails (step S17: No), the control unit 15 outputs the authentication result to the display control unit 36. The display control unit 36 displays an error message on the display unit 37. Specifically, the display control unit 36 lights the LED lamps 370A etc. by using a predetermined method indicating that the authentication has failed. Next, the authentication unit 35 determines whether or not to retry the authentication process. For example, the authentication unit 35 reads out, from the memory unit 38, a preset number of retries, and compares the number of retries that has been read out with the number of times the authentication process has been performed after the user put on the ring 10A. If the number of times the authentication process has been performed is equal to or more than the predetermined number of retries, then the authentication unit 35 determines that no further retries will be allowed (step S19: No), and the processing flow ends. The authentication unit 35 outputs the authentication result to the control unit 15. Based on the authentication result, the control unit 15 performs control so as to disable the functions using various services making use of personal information stored in the memory unit 11. The user is then not able to make use of payment services and the like using the ring 10A.

As long as the number of times the authentication process has been performed is equal to or less than the predetermined number of retries, the authentication unit 35 determines that a retry will be performed (step S19: Yes) and instructs the wearing position determination unit 34 to retry authentication. The wearing position determination unit 34 repeats the process beginning at step S14. When determining whether or not the wearing position of the ring 10A is correct during a retry, the wearing position determination unit 34 may more strictly determine the wearing position than during the first determination. For example, the tolerance range for the misalignment in the movement distance and the rotational position from the determination criteria values used during the second determination may be made narrower than the tolerance range used during the first determination, and the determination may be performed using an even narrower tolerance range on the third retry. As a result thereof, it is possible to capture an image including the vein pattern of the user at a more precise position, and to perform authentication by means of said image.

Up to this point, the case in which vein authentication is performed by aligning the wearing position of the ring 10A with a predetermined lateral position and a predetermined rotation direction position (authentication method 1) has been explained. In the present exemplary embodiment, an authentication image of the vein pattern captured from one direction is encrypted and pre-registered, and authentication is performed by collation with that authentication image. In the case of this method, when the user starts using the ring 10A, an authentication image, captured by the imaging unit 32 with the ring 10A worn at a position at which the user normally wears the ring 10A, is registered in the memory unit 38. Additionally, when capturing the authentication image for the first time, the ring 10A is worn with the back of the hand facing upwards and a predetermined surface of the ring 10A facing upwards, and the wearing position determination unit 34 records, in the memory unit 38, the distances between the electrostatic capacitive sensors 311A to 311D and the finger 3 at that wearing position. Additionally, the wearing position determination unit 34 uses the detection results from the acceleration sensor 310 to compute the distance from the position at which the wearing detection unit 33 detects the start of the wearing action to the wearing position at which the ring 10A is normally worn, and records the distance in the memory unit 38.

Additionally, the following method may also be employed as another authentication method (authentication method 2). In other words, during an initial setup for registering an authentication image and authentication position information in the memory unit 38, the imaging unit 32 continuously captures an authentication image as the ring 10A is turned by one full circuit, while wearing the ring 10A at the lateral position at which it is normally worn by the user. This is not limited to cases in which an authentication image captured from all circumferential directions over 360° is registered and, for example, it is possible to capture authentication images from multiple angles by turning the ring 10A, for example, 10° at a time. The memory unit 38 stores an encrypted authentication image covering one full circuit (or captured from multiple angles) at the predetermined lateral position. Additionally, the wearing position determination unit 34 uses the detection results from the acceleration sensor 310 to compute the distance to the predetermined lateral position at which the user normally wears the ring 10A, and records the information in the memory unit 38. If an authentication image of one full circuit has been obtained, in step S14 in FIG. 9, the wearing position determination unit 34 only uses the lateral position to determine whether or not the wearing position is correct. Additionally, the authentication unit 35 performs the authentication process by collating the image captured by the imaging unit 32 with each of the full-circuit authentication images stored in the memory unit 38. The image captured by the imaging unit 32 during the initial setup may be recorded in the memory unit 38 in association with the detection result of the acceleration sensor 310 and the distances between the respective electrostatic capacitive sensors 311A to 311D and the finger 3 at the time the image was captured. In this case, in step S14 in FIG. 9, the wearing position determination unit 34 determines whether or not the wearing position is correct by determining only the lateral position. Additionally, in step S16, the authentication unit 35 uses the detection result of the acceleration sensor 310 and the detection results of the electrostatic capacitive sensors 311A to 311D to read out, from the memory unit 38, the authentication image registered in association with those values or the authentication image associated with detection results that are within a predetermined range from those detection results, and collates that authentication image with the captured image of the user's finger 3. As a result thereof, it is possible to reduce the processing load for the collation process. Additionally, the authentication process can also be performed in the case where authentication images are registered for multiple angles instead of one full circuit. By using this authentication method 2, the authentication unit 35 can perform the authentication process regardless of the rotation direction position, or at multiple positions of the ring 10A when worn by the user.

As another authentication method (authentication method 3), it is possible to employ the following method. In this method, at the time of the initial setup, an encrypted authentication image obtained by capturing the finger 3 omnidirectionally over a predetermined lateral range including the lateral position at which the ring 10A is normally worn is registered in the memory unit 38. In the case of this method, in step S14 in FIG. 9, the wearing position determination unit 34 determines whether or not the wearing position is correct by determining whether or not the lateral position is included within the predetermined lateral range over which the authentication image was captured. Additionally, the authentication unit 35 performs the authentication process by collating the image captured by the imaging unit 32 with each of the authentication images stored in the memory unit 38. The authentication image that was captured at the time of the initial setup may be registered in the memory unit 38 in association with information regarding the lateral position and the rotation direction position at the time the ring 10A was worn, which corresponds to the authentication image. In this case, in step S16 in FIG. 9, the authentication unit 35 uses the detection result of the acceleration sensor 310 and the detection results of the electrostatic capacitive sensors 311A to 311D to compute the lateral position and the rotation direction position, reads out, from the memory unit 38, the authentication image registered in association with those lateral and rotation direction positions or the authentication image registered in association with detection results that are within a predetermined range from those lateral and rotation direction positions, and collates those authentication images with the captured image of the user's finger 3. As a result thereof, it is possible to reduce the processing load for the collation process. By using this authentication method 3, the authentication unit 35 can perform the authentication process without being limited as to the wearing position of the ring 10A. This authentication method 3 is also not limited to obtaining an authentication image of one full circuit captured omnidirectionally, and it is possible to register authentication images captured from multiple angles.

<Other Examples of Wearing Position Determination>

Up to this point, examples wherein the wearing position of the ring 10A is determined by means of the lateral position measured by the acceleration sensor 310, the distances between the electrostatic capacitive sensors 311A to 311D and the finger 3, and the tilt of the ring 10A measured by the acceleration sensor 310 have been explained. As other methods, the wearing position may be determined by the following methods.

<Position Determination by Finger Surface Image>

In position determination by using a finger surface image, the vein authentication position is determined by making use of the pattern of wrinkles (skin patterns) on the skin of the finger. In the case of this method, a visible light source is provided on a surface facing the TFT sensor 321 in FIG. 3, and the TFT sensor 321 captures an image of the surface of the finger 3 while the ring 10A is being worn. The memory unit 38 pre-stores a position determination image obtained by capturing an image of the surface of the finger 3 when the ring 10A is being worn. The wearing position determination unit 34 collates the position determination image with an image of the skin pattern captured by the imaging unit 32 to determine whether or not the ring 10A is being worn at a position that is appropriate for performing authentication.

<Position Determination Using Pulse Sensor>

In position determination using a pulse sensor, a pulse sensor is provided on the inner circumference of the ring 10A, and the pulse is detected. The memory unit 38 stores an authentication image captured at a position at which the pulse sensor is able to detect a pulse. The wearing position determination unit 34 determines that the ring 10A is worn at a position that is appropriate for performing authentication when the pulse sensor is able to detect a pulse. As a different method, the pulse sensor may detect the pulse intensity, and the wearing position determination unit 34 may determine that the ring 10A is being worn at an appropriate position when the pulse intensity is a predetermined value. The position at which the pulse sensor is able to detect a pulse and the position at which the user normally wears the ring 10A may be different. As an example in which authentication is performed irrespective of the position at which the ring 10A is normally worn, the following method may be employed. The position of the root of a fingernail does not change. Therefore, an authentication image including a vein pattern that can be captured when either end surface of the ring 10A is aligned with the position of the root of a fingernail may be registered in the memory unit 38, and when performing authentication, vein authentication may be performed by aligning the ring 10A with the position of the root of the fingernail.

<Position Determination Using Pressure Sensor>

In position determination using a pressure sensor, a pressure sensor is provided on the inner circumference of the ring 10A. The memory unit 38 stores a pressure value (determination criterion value) detected by the pressure sensor when the ring 10A is being worn at the position at which authentication is to be performed. The wearing position determination unit 34 determines that the ring 10A is being worn at a position that is appropriate for performing authentication when the pressure value detected by the pressure sensor is within a predetermined range with respect to the determination criterion value.

<Position Determination Using Temperature Sensor>

Similarly, it is possible to provide a temperature sensor on the inner circumference of the ring 10A and to determine the position by means of the temperature. The memory unit 38 stores, as a determination criterion temperature, the surface temperature of the finger 3 when the user is wearing the ring 10A. The wearing position determination unit 34 determines that the ring 10A is being worn at a position that is appropriate for performing authentication when the temperature detected by the temperature sensor is within a predetermined range of the determination criterion temperature.

<Position Determination Using Ultrasonic Sensor>

In position determination using an ultrasonic sensor, an ultrasonic sensor is provided on the ring 10A. By using an ultrasonic sensor, for example, the distance between the surface of the finger 3 and a bone can be detected by means of an echo when the finger 3 is irradiated with ultrasonic waves. The wearing position determination unit 34 determines the rotation direction position of the ring 10A based on the distance between the surface and the bone in the finger 3 detected by the ultrasonic sensor.

Other Examples

Infrared rays easily pass through at the positions of the finger joints. By making use of this property, the wearing position determination unit 34 detects a finger joint position in accordance with the amount of light received by the TFT sensor 321 while the user is moving the ring 10A in the lateral direction. Additionally, the wearing position determination unit 34 may determine the lateral position of the ring 10A by computing the movement distance from the finger joint position by using the detection results from the acceleration sensor 310.

The detection results by the various sensors used for position determination mentioned here may also be used for authentication. For example, skin pattern authentication may be used instead of vein authentication, or a combination thereof may be used.

According to the present exemplary embodiment, it is possible to use a ring-type wearable terminal (ring 10A) that is compact enough that it does not get in the way even when worn on the body all of the time. Additionally, according to the authentication device of the present exemplary embodiment, it is possible to authenticate whether or not a user who is wearing the ring 10A is a legitimate user by means of vein authentication. Additionally, when performing vein authentication, the ring 10A need to be worn at the position at which authentication is to be performed. According to the authentication device 30A in the present exemplary embodiment, it is possible to determine whether or not the wearing position of the ring 10A is the position at which authentication is to be performed, and to provide support for the user to wear the ring 10A at the appropriate position by providing guide displays indicating the appropriate wearing position.

Second Exemplary Embodiment

Herebelow, an authentication system according to a second exemplary embodiment of the present invention will be explained with reference to FIGS. 10 and 11.

Figure 10:
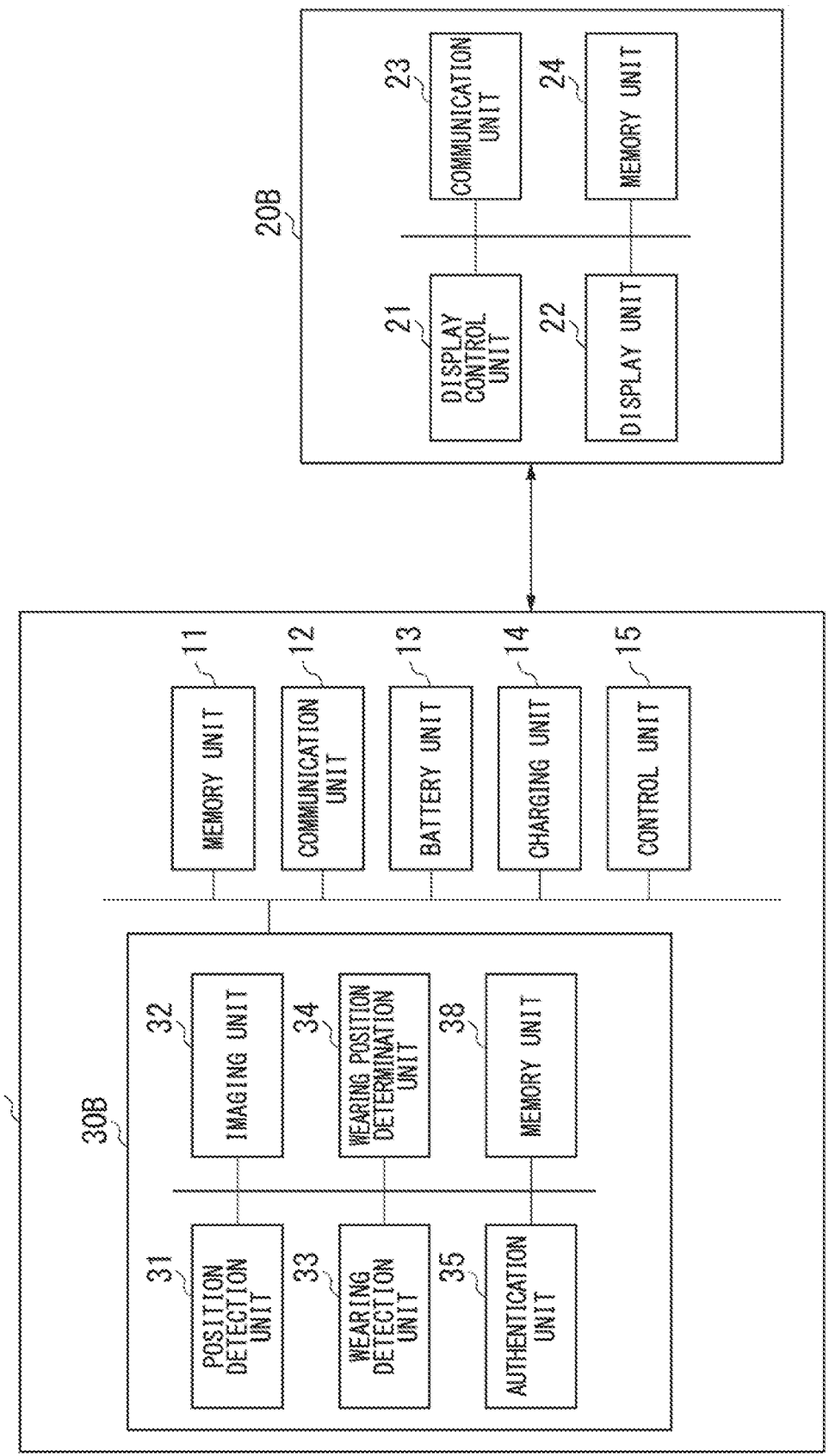
FIG. 10 is a diagram illustrating an example of the authentication system according to a second exemplary embodiment of the present invention.

FIG. 10 is a diagram illustrating an example of the authentication system according to the second exemplary embodiment of the present invention.

As illustrated in FIG. 10, the authentication system according to the present exemplary embodiment includes a wearable article 10B and a display device 20B. The wearable article 10B and the display device 20B may be connected so as to be able to communicate with each other. In the example illustrated in FIG. 10, the wearable article 10B includes a memory unit 11, a communication unit 12, a battery unit 13, a charging unit 14, a control unit 15 and an authentication device 30B. The authentication device 30B includes a position detection unit 31, an imaging unit 32, a wearing detection unit 33, a wearing position determination unit 34, an authentication unit 35 and a memory unit 38. The functional units of the authentication system according to the second exemplary embodiment will be explained by appending the same reference symbols for parts that are the same as those in the first exemplary embodiment. The wearable article 10B is, for example, a ring-type wearable terminal. The specific structure of the wearable article 10B is the same as that of the wearable article 10A illustrated in FIG. 3.

The display device 20B includes a display control unit 21, a display unit 22, a communication unit 23 and a memory unit 24. The display control unit 21 displays, on the display unit 22, information that is to be presented to the user, based on information received by the communication unit 23. The display unit 22 is a display that is combined integrally with an element having an input function, such as a touch panel. The communication unit 23 communicates with the wearable article 10B. The memory unit 24 stores various types of information. The display device 20B is, for example, an electronic terminal such as a smartphone or a tablet terminal. In the second exemplary embodiment, the display device 20B displays authentication results and position determination results from the wearable article 10B. The user can adjust the wearing position of the wearable article 10B by referring to the information displayed by the display device 20B.

The operations of the second exemplary embodiment will be explained. When the user puts on the wearable article 10B, the authentication device 30B determines whether or not the user wearing the wearable article 10B is a legitimate user. The processing in the authentication device 30B is the same as that in the first exemplary embodiment. Specifically, the position detection unit 31 detects information relating to the wearing position, and the wearing position detection unit 34 determines whether or not the wearing position of the wearable article 10B is the position at which authentication is to be performed. When the wearing position is determined to be the position at which authentication is to be performed, the authentication unit 35 uses an image captured by the imaging unit 32 to perform vein authentication in order to perform authentication as to whether the user wearing the wearable article 10B is a legitimate user.

In the present exemplary embodiment, the wearing position determination unit 34 outputs the wearing position determination result to the communication unit 12. Additionally, the authentication unit 35 outputs the authentication result to the communication unit 12. The communication unit 12 transmits this information to the display device 20B. In the display device 20B, the communication unit 23 receives this information from the wearable article 10B and outputs the information to the display control unit 21. The display control unit 21 uses the information received from the wearable article 10B to generate a display image that is to be displayed on the display unit 22.

Additionally, using the case in which the wearable article 10B is a ring as the example, during the initial setup, the communication unit 12 obtains an authentication image and information regarding the position at which authentication is to be performed (such as information regarding the predetermined lateral position and rotation direction position) from the wearing position determination unit 34, and transmits the same to the display device 20B. In the display device 20B, the communication unit 23 receives this information relating to the authentication position and writes the information into the memory unit 24 for storage.

Figure 11:
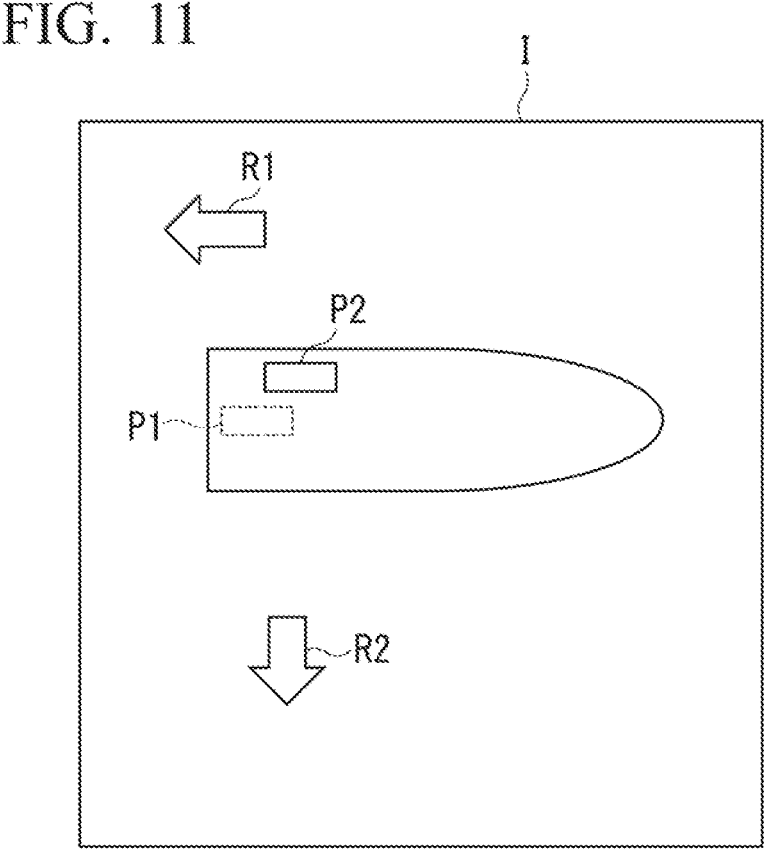
FIG. 11 is a diagram illustrating an example of a display in the authentication system according to the second exemplary embodiment of the present invention.

FIG. 11 is a diagram illustrating display examples in the authentication system according to the second exemplary embodiment of the present invention.

Upon determining, in step S14 in FIG. 9, that the wearing position is incorrect, the wearing position determination unit 34 transmits computed lateral position and rotation direction position information, and information indicating that the determination of the wearing position has failed, to the display device 20B via the communication unit 12. In the display device 20B, the display control unit 21 generates an image I, as illustrated in FIG. 11, on the basis of the lateral and rotation direction position information received from the wearable article 10B, and the lateral and rotation direction position information of the authentication position stored by the memory unit 24, and displays the image I on the display unit 22. The position P1 indicated by the dashed lines in FIG. 11 indicates the authentication position stored in the memory unit 24. The position P2 indicated by the solid lines shows the authentication position at the current wearing position based on the information received from the wearable article 10B. The display control unit 21 displays information for improving the wearing position of the wearable article 10B so as to be the position at which authentication is to be performed (FIG. 11, arrows R1 and R2). The user can adjust the wearing position of the wearable article 10B by referring to this display.

If the authentication by the authentication unit 35 fails, the display control unit 21 makes the display unit 22 display a message such as: "Authentication failed". During the authentication process by the authentication unit 35, the display control unit 21 makes the display unit 22 display a message such as: "Authenticating". When retrying the authentication process, the display control unit 21 makes the display unit 22 display a message such as: "Retrying". When the wearing detection unit 33 detects that the wearing action has started, the display control unit 21 makes the display unit 22 display a message such as: "Wearing start detected". Thus, in the present exemplary embodiment, the processing conditions in the authentication device 30B are coordinated with the information displayed by the display device 20B. As a result, it is possible to improve the convenience from when the user puts on the wearable article 10B until authentication is performed.

Next, the process for registering the authentication image of the vein pattern will be explained.

Figure 12:
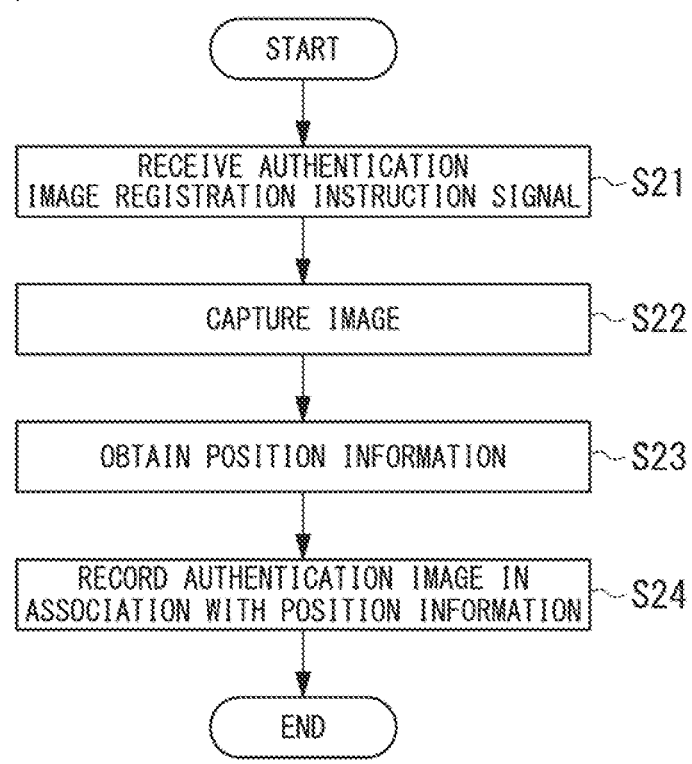
FIG. 12 is a flow chart illustrating an example of an authentication image registration method according to the second exemplary embodiment of the present invention.

FIG. 12 is a flow chart showing an example of the method for registering the authentication image according to the second exemplary embodiment of the present invention.

First, the user performs a predetermined operation on the display unit 22 so that a screen for accepting an authentication image registration instruction is displayed on the display unit 22. Additionally, the user wears the wearable article 10B at the position at which it is normally worn. Next, the user performs an operation instructing the display unit 22 to start authentication image registration. Then, the display unit 22 accepts the operation instructing that the registration of the authentication image should be started, and transmits, via the communication unit 23, a signal instructing the wearable article 10B to register an authentication image. In the wearable article 10B, the communication unit 12 receives the authentication image registration instruction signal (step S21).

The communication unit 12 outputs a registration instruction signal to the imaging unit 32. Next, the imaging unit 32 captures the authentication image (step S22). Specifically, the authentication image is an image including a vein pattern taken at a position at which the wearable article 10B is worn by the user. Next, the wearing position determination unit 34 obtains position information for the wearing position of the wearable article 10B (step S23). For example, the wearing position determination unit 34 uses the detection results from the acceleration sensor 310 to compute the distance from the position at which the wearing position detection unit 33 detected the start of the wearing action to the wearing position at which the wearable article 10B is normally worn. Additionally, the wearing position determination unit 34 obtains the distances to the finger 3 detected by the electrostatic capacitive sensors 311A to 311D. Additionally, the wearing position determination unit 34 obtains coordinate information for the detection results from the acceleration sensor 310. In this way, the wearing position determination unit 34 obtains the lateral position and the rotation direction position of the wearable article 10B. The wearing position determination unit 34 records the obtained position information in the memory unit 38. Next, the imaging unit 32 encrypts the captured authentication image and records the encrypted image in the memory unit 38, in association with the already recorded position information (step S24). As a result thereof, it is possible to register an authentication image captured from one direction, and to perform an authentication process for a user wearing the wearable article 10B.

Third Exemplary Embodiment

Herebelow, an authentication system according to a third exemplary embodiment of the present invention will be explained with reference to FIG. 13.

Figure 13:
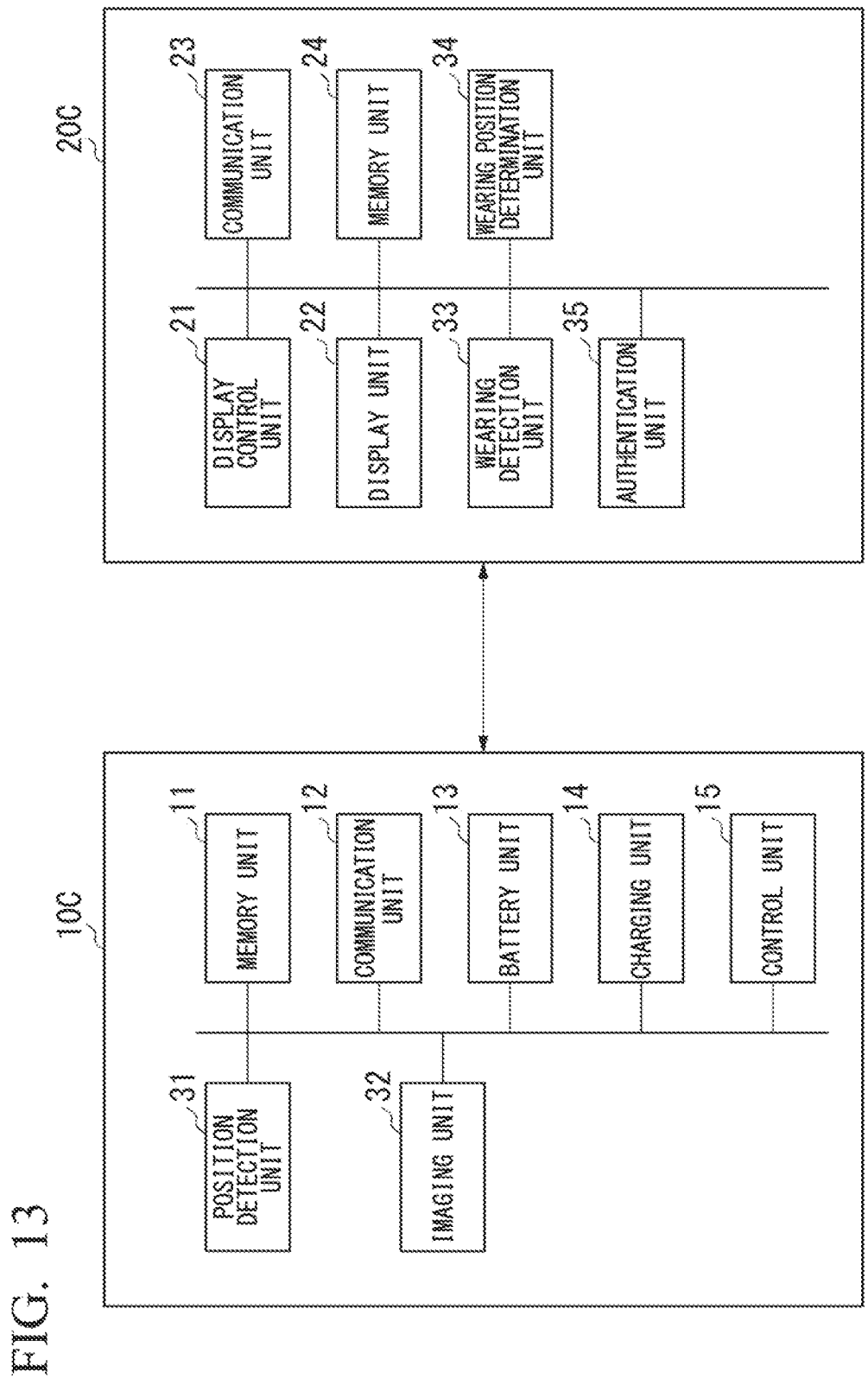
FIG. 13 is a diagram illustrating an example of the authentication system according to a third exemplary embodiment of the present invention.

FIG. 13 is a diagram illustrating an example of an authentication system according to a third exemplary embodiment of the present invention.

As shown in FIG. 13, the authentication system according to the present exemplary embodiment includes a wearable article 10C and an information processing device 20C. The wearable article 10C and the information processing device 20C are connected so as to be able to communicate with each other. The functional units of the authentication system according to the third exemplary embodiment will be explained by appending the same reference symbols for parts that are the same as those in the first exemplary embodiment. In FIG. 13, the wearable article 10C includes a memory unit 11, a communication unit 12, a battery unit 13, a charging unit 14, a control unit 15, a position detection unit 31 and an imaging unit 32.

The information processing device 20C includes a display control unit 21, a display unit 22, a communication unit 23, a memory unit 24, a wearing detection unit 33, a wearing position determination unit 34 and an authentication unit 35. The information processing device 20C is, for example, an electronic terminal such as a smartphone or a tablet terminal. In the third exemplary embodiment, the information processing device 20C receives, from the wearable article 10C, an image used in the authentication process and information relating to the wearing position used for position determination. The information processing device 20C uses the received information to perform processes for determining the wearing position of the wearable article 10C and performing authentication as to whether or not the user is a legitimate user. Additionally, in the third exemplary embodiment, the memory unit 24 of the information processing device 20C stores an encrypted image including biometric information of the user and various types of information necessary for the authentication process The operations of the third exemplary embodiment will be explained. When the user puts on the wearable article 10C, the position detection unit 31 detects information relating to the wearing position and transmits the information relating to the wearing position, via the communication unit 12, to the information processing device 20C. At the information processing device 20C, the communication unit 23 receives the information relating to the wearing position and outputs the information to the wearing detection unit 33. The wearing detection unit 33 detects that the user has started a wearing action of the wearable article 10C. When the wearing detection unit 33 detects the start of the wearing action, the communication unit 23 outputs, to the wearing position determination unit 34, information relating to the wearing position, received from the wearable article 10C. Based on the information relating to the wearing position detected by the position detection unit 31, the wearing position determination unit 34 determines whether or not the wearing position of the wearable article 10C is the position at which authentication is to be performed. If it is determined that the wearing position of the wearable article 10C is not the position at which authentication is to be performed, the wearing position determination unit 34 outputs the wearing position determination results to the display control unit 21. The display control unit 21 generates an image indicating that the wearing position should be adjusted, and makes the display unit 22 display the image. If it is determined that the wearing position is the position at which authentication is to be performed, the wearing position determination unit 34 notifies the wearable article 10C, via the communication unit 23, that the authentication position is correct. In the wearable article 10C, this notification is received and the imaging unit 32 captures an image including a vein pattern. The communication unit 12 transmits the image captured by the imaging unit 32 to the information processing device 20C. At the information processing device 20C, the communication unit 23 obtains the image and outputs the image to the authentication unit 35. The authentication unit 35 performs an authentication process. The authentication unit 35 outputs the result of the authentication process to the display control unit 21. The display control unit 21 makes the display unit 22 display the authentication result.

According to the present exemplary embodiment, it is possible to reduce the functions that are installed in the wearable article 10C and to reduce the processing load in the wearable article 10C. Additionally, it is possible to perform processes having a high load, such as wearing position determination and authentication processes, by using the information processing device 20C, so the present exemplary embodiment is also appropriate for use, for example, with the above-mentioned authentication method 2 and authentication method 3, which involve a high processing load.

The third exemplary embodiment may also be combined with the first exemplary embodiment or the second exemplary embodiment. For example, an example in which the ring 10A of the first exemplary embodiment is combined with the information processing device 20C of the third exemplary embodiment will be explained. First, an authentication process is performed with the ring 10A, using authentication method 1. If authentication fails even when the authentication is retried a predetermined number of times, the imaging unit 32 transmits the captured image to the information processing device 20C, and in the information processing device 20C, an authentication process is performed by collating the image captured by the imaging unit 32, at the position at which the ring 10A is being worn, with respective images including the vein patterns detected from multiple directions at predetermined positions of the finger wearing the ring 10A, as in authentication method 2 or authentication method 3.

Fourth Exemplary Embodiment

Herebelow, an authentication system according to a fourth exemplary embodiment of the present invention will be explained with reference to FIGS. 14 and 15.

The structure of the authentication system according to the fourth exemplary embodiment is the same structure as that of the second exemplary embodiment or the third exemplary embodiment. Herebelow, the explanation will be made by using the structure in the second exemplary embodiment. Additionally, as the specific structure, it will be assumed that the wearable article 10B has the same structure as that in FIG. 3.

The authentication system according to the fourth exemplary embodiment reduces the burden of the user to align the position when putting on the wearable article 10B. According to this fourth exemplary embodiment, if the wearable article 10B is a ring-type wearable terminal, the user is able to perform authentication by aligning just the lateral position of the wearable article 10B. First, the authentication image registration method in the present exemplary embodiment will be explained.

Figure 14:
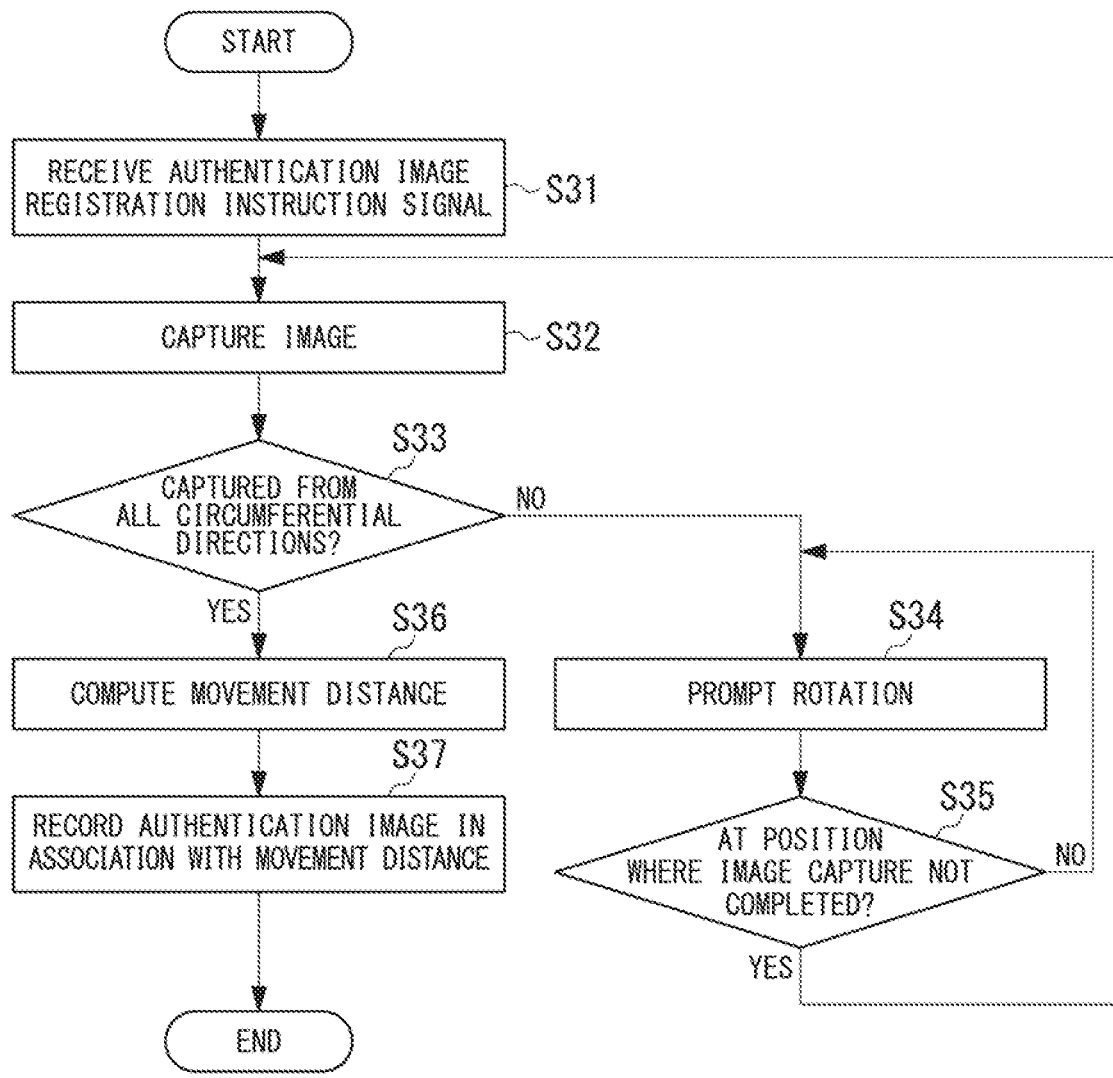
FIG. 14 is a flow chart illustrating an example of an authentication image registration method according to a fourth exemplary embodiment of the present invention.

FIG. 14 is a flow chart showing an example of the authentication image registration method in the fourth exemplary embodiment of the present invention.

First, the user performs a predetermined operation on the display unit 22 and causes the display unit 22 to display a screen for accepting instructions to register an authentication image. Additionally, the user wears the wearable article 10B at the position at which it is normally worn. Next, the user performs an operation on the display unit 22 providing instructions to start the registration of the authentication image. Then, the display unit 22 accepts the operation providing instructions to start the registration of the authentication image, and transmits a signal to the wearable article 10B, via the communication unit 23, providing instructions to register the authentication image. Additionally, the display unit 22 generates a display prompting the user to rotate the wearable article 10B. In the wearable article 10B, the communication unit 12 receives the authentication image registration instruction signal (step S31). The communication unit 12 outputs a registration instruction signal to the imaging unit 32. Next, the imaging unit 32 captures an authentication image (step S32). Specifically, the authentication image is an image including a vein pattern at the position at which the user is wearing the wearable article 10B. Additionally, the user rotates the wearable article 10B in the circumferential direction of the finger while the imaging unit 32 captures the authentication image. Next, the wearing position determination unit 34 determines whether or not the imaging unit 32 has captured images from all circumferential directions at the wearing position of the wearable article 10B (step S33). For example, the wearing position determination unit 34 determines whether or not the wearable article 10B has completed one full turn based on detection values from the acceleration sensor 310. The images captured from all circumferential directions are not limited to being images taken omnidirectionally over 360°, and may be, for example, be images captured from multiple angles turned 10° at a time. If the capturing of images from all circumferential directions is not completed (step S33: No), then the wearing position determination unit 34 notifies the display device 20B, via the communication unit 12, that images have not been captured from all circumferential directions. In the display device 20B, the display control unit 21 displays, on the display unit 22, a message prompting the user to rotate the wearable article 10B in the circumferential direction of the finger, based on the notification (step S34). Next, on the basis of the output of the acceleration sensor 310, the wearing position determination unit 34 determines whether or not the rotation direction position of the wearable article 10B is a position at which the capturing of the authentication image has not been completed (step S35). If the rotational position of the wearable article 10B is not a position at which the capturing of the image has not been completed (step S35: No), then the process returns to step S34 and the user is again prompted to rotate the wearable article 10B. On the other hand, if the rotational position of the wearable article 10B is a position at which the capturing of the image has not been completed (step S35: Yes), then the process is repeated from step S32. Specifically, the wearing position determination unit 34 instructs the imaging unit 32 to capture images. The imaging unit 32 captures an authentication image.

On the other hand, if it is determined, in step S33, that the capturing of the authentication images from all circumferential directions has been completed (step S33: Yes), then the wearing position determination unit 34 uses the detection results from the acceleration sensor 310 to compute the movement distance from the position at which the wearing detection unit 33 detected the start of the wearing action to the wearing position of the wearable article 10 (step S36). The wearing position determination unit 34 records the computed position information in the memory unit 38. Next, the imaging unit 32 encrypts the captured authentication image and records the encrypted image in the memory unit 38 in association with the computed movement distance (step S37). At this time, the imaging unit 32 may record an authentication image captured from each direction. As a different method, the imaging unit 32 may record a three-dimensional image reconstructed from authentication images captured from all directions. In the above-mentioned explanation, the case in which authentication images are captured from all circumferential directions has been explained, but the present exemplary embodiment is not limited to such an example. For example, the arrangement may be such that images are captured over a rotational angle range of 180° (a range of rotational angles from 0° to 180°), from the inner side of the finger to the back of the finger. As a result thereof, it is possible to register a row of authentication images captured from all circumferential directions of the finger at the position at which the wearable article 10B is worn.

Next, by referring to FIG. 15, the authentication process in the fourth exemplary embodiment will be explained while focusing on the processing flow for aligning the wearable article 10B at a position that is appropriate for vein authentication.

Figure 15:
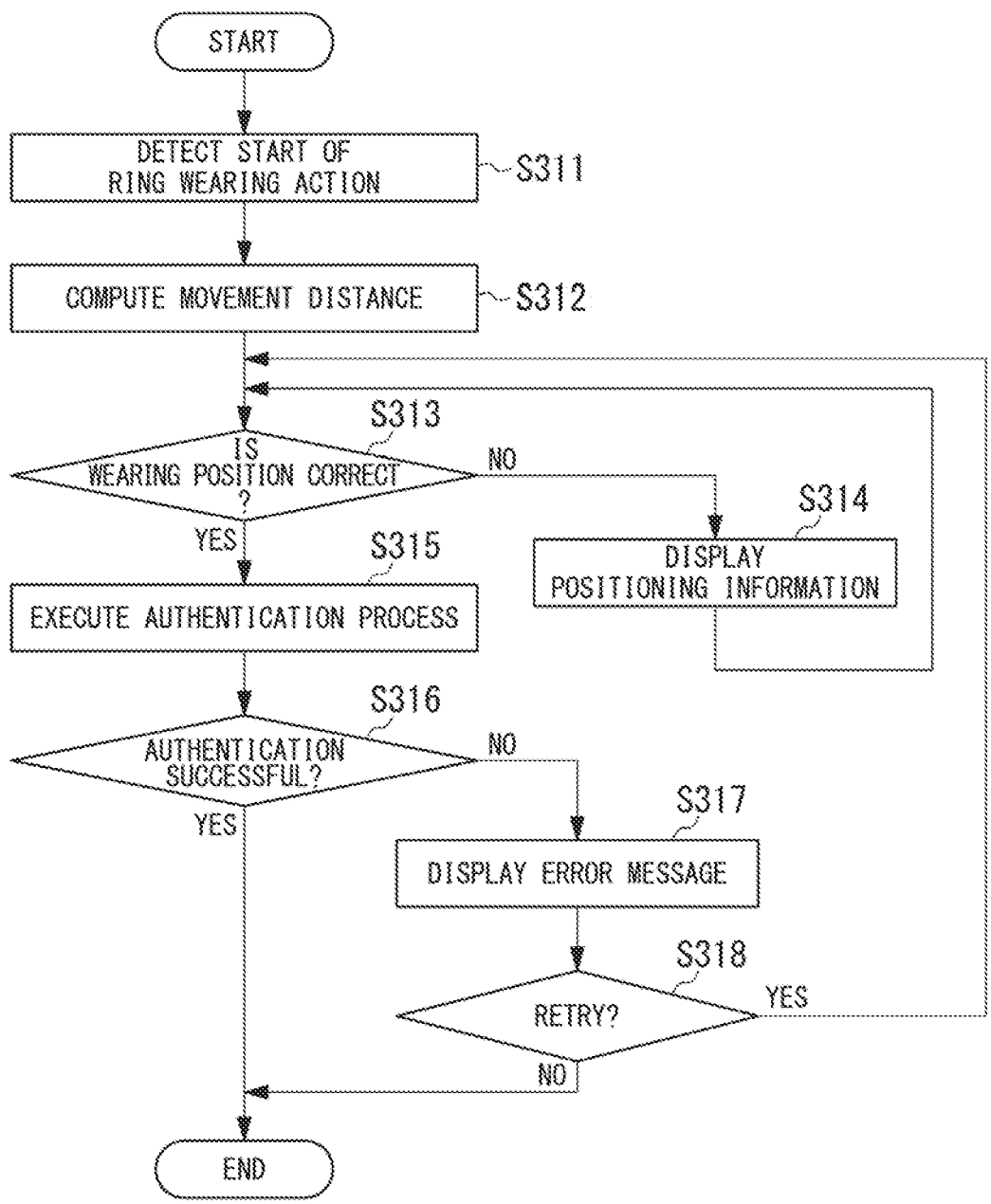
FIG. 15 is a flow chart illustrating an example of the authentication method according to the fourth exemplary embodiment of the present invention.

FIG. 15 is a flow chart showing an example of the authentication method according to the fourth exemplary embodiment of the present invention.

It is assumed that the user is putting on the wearable article 10B with the back of the hand facing upwards, while keeping the movement direction of the wearable article 10B horizontal.

First, the user starts putting the wearable article 10B on the finger. When the wearable article 10B starts being put on the finger, each of the electrostatic capacitive sensors 311A to 311D detect the distance to the finger and output the distance information to the wearing detection unit 33. The wearing detection unit 33 detects the start of the wearing action of the wearable article 10B on the finger 3 based on the distance information obtained from the electrostatic capacitive sensors 311A to 311D (step S311). For example, the wearing detection unit 33 detects the start of the wearing action when all of the obtained values of the distance information are within a predetermined range. Then, the wearing detection unit 33 outputs, to the wearing position determination unit 34, a signal indicating that the wearing action has started. Upon obtaining the signal indicating that the wearing action has started, the wearing position determination unit 34 starts obtaining acceleration information from the acceleration sensor 310. The user moves the wearable article 10B to the predetermined wearing position and temporarily halts the wearing action.

When the movement of the wearable article 10B stops, the wearing position determination unit 34 uses acceleration information obtained at predetermined time intervals to compute the horizontal movement distance (step S312).

Next, the wearing position determination unit 34 determines whether or not the wearing position of the wearable article 10B is correct (step S313). The wearing position determination unit 34 reads out, from the memory unit 38, the movement distance (determination criterion value) of the wearable article 10B recorded in association with the authentication image at the time of registration of the authentication image. The wearing position determination unit 34 compares the movement distance that has been read out with the horizontal movement distance computed in step S312. If the horizontal movement distance is equal to the determination criterion value or if it is within a range that can be considered to be equivalent, then the wearing position determination unit 34 determines that the wearing position of the wearable article 10B is correct (at the position at which authentication is to be performed). If that is not the case, then the wearing position determination unit 34 determines that the wearing position of the wearable article 10B is not correct. If it is determined that the wearing position of the wearable article 10B is not correct (step S313: No), then the wearing position determination unit 34 outputs, to the display control unit 36, information regarding the difference between the determination criterion value and a value indicating the wearing position of the wearable article 10B. The display control unit 36 displays, on the display unit 37, positioning information for improving the wearing position (step S314). Specifically, the wearing position determination unit 34 transmits the computed horizontal movement distance information to the display unit 20B via the communication unit 12. In the display device 20B, the display control unit 21 generates an image (positioning information) indicating the amount of misalignment in the wearing position of the wearable article 10B and displays the image on the display unit 22. The user adjusts the position of the wearable article 10B by referring to this positioning information. After the positional adjustment, the wearing position determination unit 34 repeats the process from step S313 to determine whether or not the wearing position of the wearable article 10B is the correct position which is appropriate for authentication.

On the other hand, if it is determined that the wearing position is correct (step S313: Yes), the wearing position determination unit 34 outputs, to the authentication unit 35, a signal providing instructions to carry out the authentication process. Next, the authentication unit 35 performs the authentication process (step S315). The authentication unit 35 instructs the imaging unit 32 (light source 320 and TFT sensor 321) to capture an image. The authentication unit 35 obtains the authentication image captured by the imaging unit 32. The authentication unit 35 reads out, from the memory unit 38, multiple authentication images obtained by capturing the vein pattern of a legitimate user from all circumferential directions, and collates the respective authentication images with the image currently captured by the imaging unit 32. If the similarity between the currently captured image and any of the images among the authentication images is higher than a predetermined threshold value, then the authentication unit 35 determines that the authentication has succeeded. If the authentication succeeds (step S316: Yes), the processing flow ends. The authentication unit 35 outputs the authentication results to the control unit 15. Based on the authentication results, the control unit 15 enables the functions using various services making use of personal information stored in the memory unit 11. The user is then able to make use of payment services and the like using the wearable article 10B.

If the authentication fails (step S316: No), the authentication unit 35 transmits to the display device 20B, via the communication unit 12, information indicating that the authentication has failed. In the display device 20B, the display control unit 21 displays, on the display unit 22, an error message such as: "Authentication failed. Will retry." (step S317). Next, the authentication unit 35 determines whether or not to retry the authentication process. For example, the authentication unit 35 reads out a preset number of retries from the memory unit 38, and compares the number of retries that has been read out with the number of times the authentication process has been performed since the user put on the wearable article 10B on the current occasion. If the number of times the authentication process has been performed is equal to or greater than the predetermined number of retries, then the authentication unit 35 determines that no further retries will be allowed (step S318: No), and the processing flow ends. The authentication unit 35 outputs the authentication results to the control unit 15. Based on the authentication results, the control unit 15 performs control to disable the functions using various services making use of personal information stored in the memory unit 11.

The user then becomes unable to make use of payment services and the like using the wearable article 10B. Additionally, the authentication unit 35 transmits the authentication results to the display device 20B via the communication unit 12. In the display device 20B, the display control unit 21 displays, on the display unit 22, an error message such as: "Authentication failed."

If the number of times that the authentication process was performed is within the predetermined number of retries, then the authentication unit 35 determines that authentication will be retried (step S318: Yes), and the authentication unit 35 instructs the wearing position determination unit 34 to retry the authentication. Then, the wearing position determination unit 34 repeats the process from step S313.

Thus, according to the fourth exemplary embodiment, the imaging unit 32 stores authentication images corresponding to all circumferential directions at the position at which the user is wearing the wearable article 10. As a result thereof, the authentication unit 35 can perform vein authentication without requiring the position of the wearable article 10 to be aligned in the rotational direction. For example, according to the present exemplary embodiment, there is no need to align the rotation direction position of the wearable article 10B, so there is no need to provide any marks for aligning the wearable article 10B in the rotational direction.

Fifth Exemplary Embodiment

Herebelow, an authentication system according to a fifth exemplary embodiment of the present invention will be explained with reference to FIGS. 16 and 17.

The structure of the authentication system according to the fifth exemplary embodiment is the same structure as that of the second exemplary embodiment or the third exemplary embodiment. Herebelow, the explanation will be made by using the structure in the second exemplary embodiment. Additionally, as the specific structure, it will be assumed that the wearable article 10B has the same structure as that in FIG. 3.

The authentication system according to the fifth exemplary embodiment reduces the burden of the user to align the position when putting on the wearable article 10B. According to this fifth exemplary embodiment, if the wearable article 10B is a ring-type wearable terminal, the user is able to perform authentication by aligning just the rotation direction position of the wearable article 10B. First, the authentication image registration method in the present exemplary embodiment will be explained.

Figure 16:
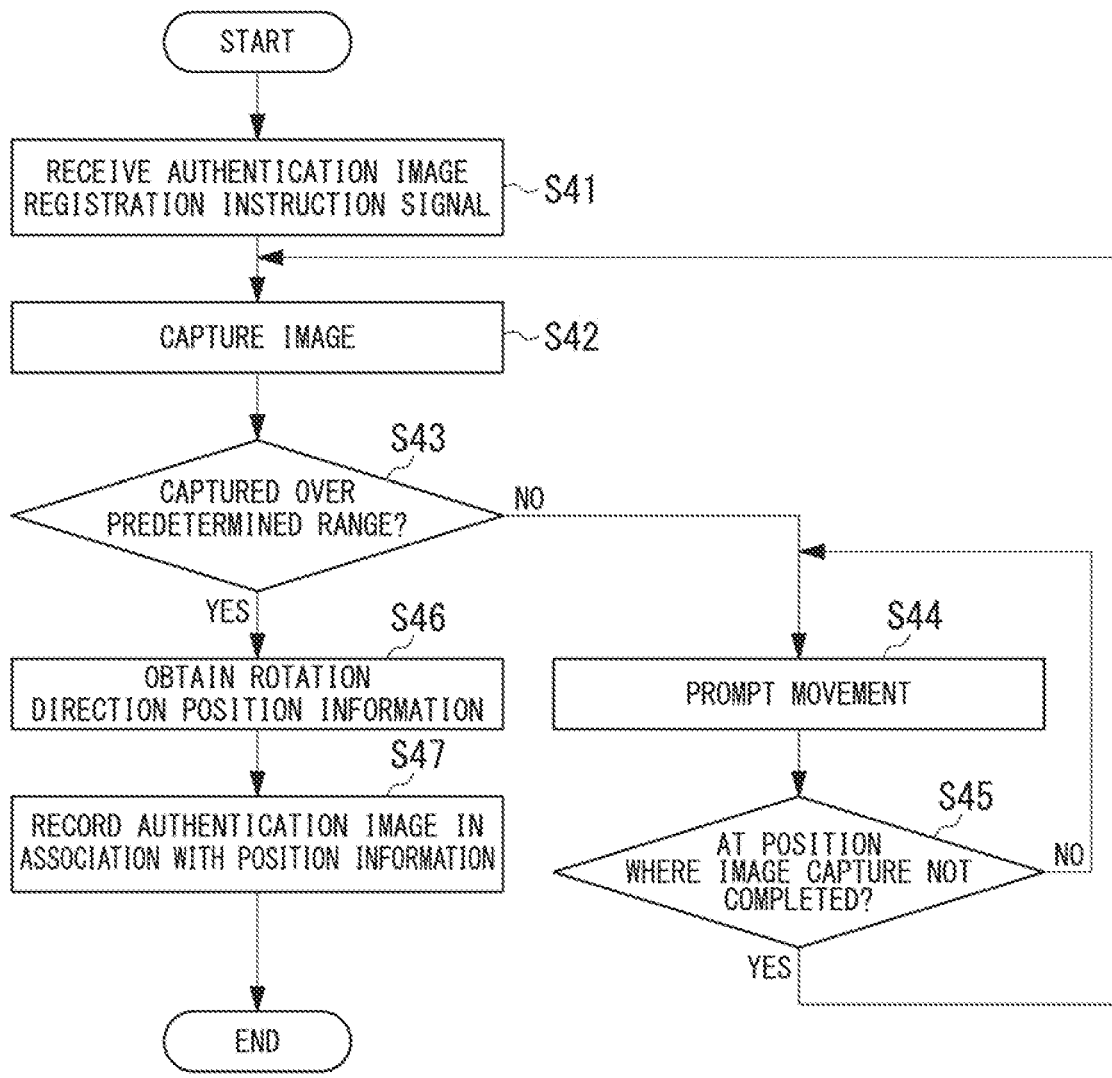
FIG. 16 is a flow chart illustrating an example of an authentication image registration method according to a fifth exemplary embodiment of the present invention.

FIG. 16 is a flow chart showing an example of the authentication image registration method in the fifth exemplary embodiment of the present invention.

First, the user performs a predetermined operation on the display unit 22 and causes the display unit 22 to display a screen for accepting instructions to register an authentication image. Additionally, the user puts on the wearable article 10B further towards the fingertip than the position at which the wearable article 10B is normally worn. Next, the user performs an operation on the display unit (reception unit) 22 providing instructions to start the registration of the authentication image. Then, the display unit 22 accepts the operation providing instructions to start the registration of the authentication image, and transmits a signal to the wearable article 10B, via the communication unit 23, providing instructions to register the authentication image. Additionally, the display unit 22 provides a display prompting the user to move the wearable article 10B in the direction of the original wearing position. In the wearable article 10B, the communication unit 12 receives the authentication image registration instruction signal (step S41). The communication unit 12 outputs the registration instruction signal to the imaging unit 32. Next, the imaging unit 32 captures the authentication image (step S42). Specifically, the authentication image is an image including a vein pattern at the position at which the user is wearing the wearable article 10B. Additionally, the user slowly moves the wearable article 10B in the direction of the base of the finger while the imaging unit 32 captures the authentication image. Next, the wearing position determination unit 34 determines whether or not the imaging unit 32 has captured images covering a predetermined range at the wearing position of the wearable article 10B (step S43). For example, the wearing position determination unit 34 uses the detection results of the acceleration sensor 310 to compute the distance from the wearing position of the wearable article 10B when the capturing of the authentication image was started to the current wearing position of the wearable article 10B. Then, the wearing position determination unit 34 compares the computed distance with a value (for example, 1.5 cm) indicating a predetermined range recorded in the memory unit 38. If the capturing of images over the predetermined range is not completed (step S43: No), then the wearing position determination unit 34 notifies the display device 20B, via the communication unit 12, that images have not been captured for the predetermined range. In the display device 20B, the display control unit 21 displays, on the display unit 22, a message prompting the user to move the wearable article 10B towards the base of the finger, based on the notification (step S44). Next, on the basis of the detection value of the acceleration sensor 310, the wearing position determination unit 34 determines whether or not the lateral position of the wearable article 10B is a position at which the capturing of the authentication image has not been completed (step S45). If the lateral position of the wearable article 10B is not a position at which the capturing of the authentication image has not been completed (step S45: No), then the process returns to step S44 and the wearing position determination unit 34 again prompts the user to move the wearable article 10B. On the other hand, if the lateral position of the wearable article 10B is a position at which the capturing of the image has not been completed (step S45: Yes), then the process is repeated from step S42. Specifically, the wearing position determination unit 34 instructs the imaging unit 32 to capture images. The imaging unit 32 then captures authentication images.

On the other hand, if it is determined, in step S43, that the capturing of images over the predetermined range has been completed (step S43: Yes), then the wearing position determination unit 34 obtains the distances from the finger detected by the electrostatic capacitive sensors 311A to 311D. Additionally, the wearing position determination unit 34 obtains coordinate information for the detection results from the acceleration sensor 310. The wearing position determination unit 34 records rotation direction position information thereof in the memory unit 38. Next, the imaging unit 32 encrypts the captured authentication image and records the encrypted authentication image in the memory unit 38, in association with the already recorded rotation direction position information (step S47). As a result thereof, it is possible to register an authentication image for one row, in the insertion direction, of the wearable article 10B, captured from one direction.

Next, by referring to FIG. 17, the authentication process in the fifth exemplary embodiment will be explained while focusing on the processing flow for aligning the wearable article 10B at a position that is appropriate for vein authentication.

Figure 17:
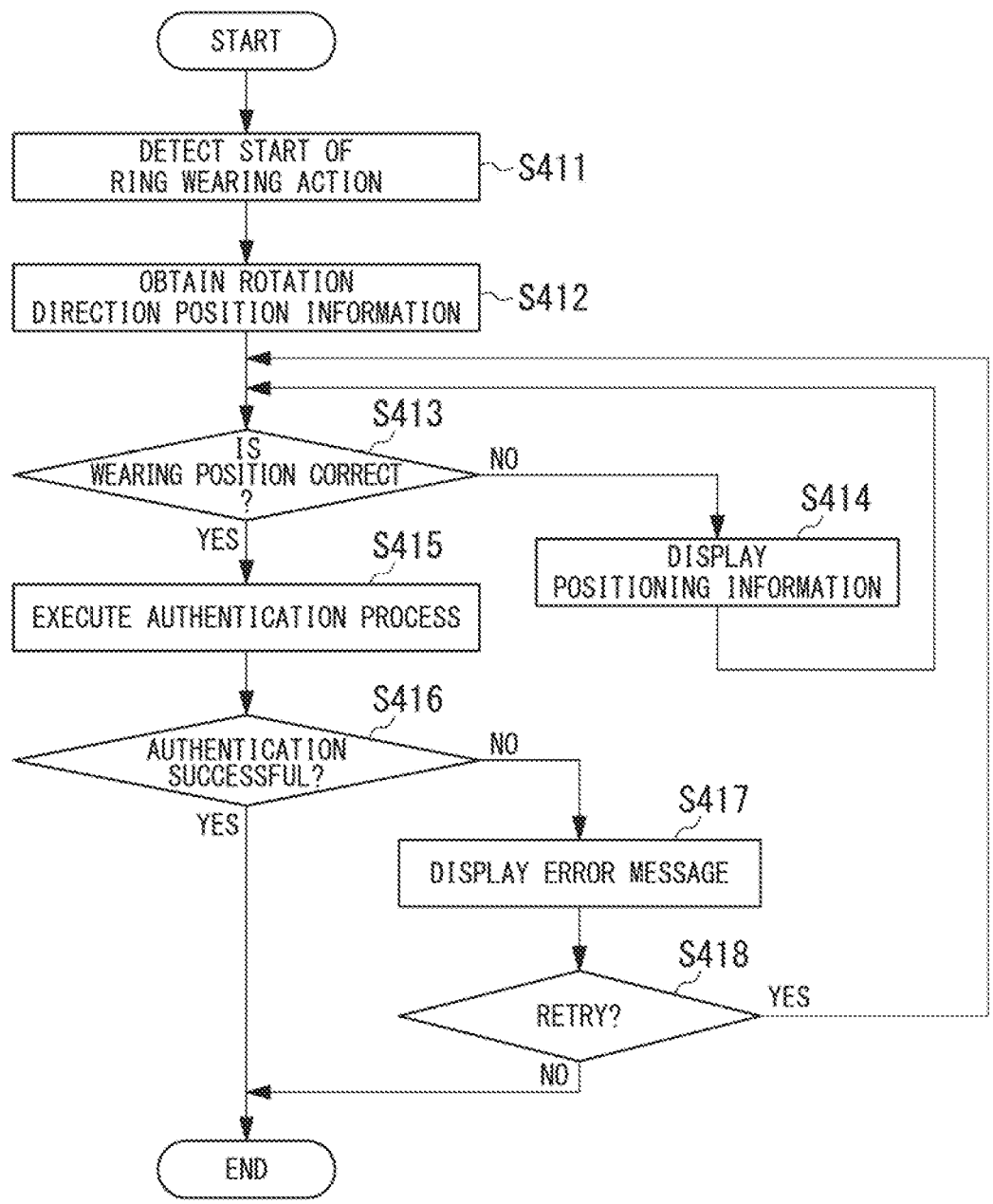
FIG. 17 is a flow chart illustrating an example of the authentication method according to the fifth exemplary embodiment of the present invention.

FIG. 17 is a flow chart showing an example of the authentication method according to the fifth exemplary embodiment of the present invention.

It is assumed that the user is putting on the wearable article 10B with the back of the hand facing upwards, while keeping the movement direction of the wearable article 10B horizontal. Additionally, the wearable article 10B has a mark appended thereto, and the user puts on the wearable article 10B, for example, with the mark facing upwards.

First, the user starts putting the wearable article 10B on the finger. When the wearable article 10B starts being put on the finger, each of the electrostatic capacitive sensors 311A to 311D detect the distance to the finger and output the distance information to the wearing detection unit 33. The wearing detection unit 33 detects the start of the wearing action of the wearable article 10B on the finger based on the distance information obtained from the electrostatic capacitive sensors 311A to 311D (step S411). For example, the wearing detection unit 33 detects the start of the wearing action when all of the values of the obtained distance information are within a predetermined range. Then, the wearing detection unit 33 outputs, to the wearing position determination unit 34, a signal indicating that the wearing action has started. When the signal indicating that the wearing action has started is obtained, the wearing position determination unit 34 starts obtaining acceleration information from the acceleration sensor 310. The user moves the wearable article 10B to the wearing position and temporarily halts the wearing action.

When the movement of the wearable article 10B stops, the wearing position determination unit 34 obtains rotation direction position information (step S412). For example, the distances to the finger 3 detected by the electrostatic capacitive sensors 311A to 311D are obtained. Additionally, the wearing position determination unit 34 obtains coordinate information of the detection results from the acceleration sensor 310.

Next, the wearing position determination unit 34 determines whether or not the wearing position of the wearable article 10B is correct (step S413). The wearing position determination unit 34 reads out, from the memory unit 38, rotation direction position information (determination criteria values) of the wearable article 10B recorded in association with the authentication image at the time of registration of the authentication image. The wearing position determination unit 34 compares the determination criteria values that have been read out with the rotation direction position information obtained in step S412. For example, the wearing position determination unit 34 reads out, from the memory unit 38, the determination criteria values for the distances between the respective electrostatic capacitive sensors 311A to 311D and the finger 3, and compares the determination criteria values that have been read out with the distance information obtained from the respective electrostatic capacitive sensors 311A to 311D in step S412. If the horizontal movement distance and the distances between the respective electrostatic capacitive sensors 311A to 311D and the finger are all equal to the determination criteria values that are set respectively therefor, or are within the ranges that can be considered to be equivalent thereto, then the wearing position determination unit 34 determines that the wearing position of the wearable article 10B is correct. If that is not the case, then the wearing position determination unit 34 determines that the wearing position of the wearable article 10B is not correct. If it is determined that the wearing position of the wearable article 10B is not correct (step S413: No), then the wearing position determination unit 34 outputs, to the display control unit 36, information regarding the difference between the determination criteria values and values indicating the wearing position of the wearable article 10B. The display control unit 36 displays, on the display unit 37, positioning information for improving the wearing position (step S414). Specifically, the wearing position determination unit 34 transmits the rotation direction position information to the display unit 20B via the communication unit 12. In the display device 20B, the display control unit 21 generates an image (positioning information) indicating the amount of misalignment of the wearing position of the wearable article 10B and displays the image on the display unit 22. The user adjusts the wearing position of the wearable article 10B by referring to this positioning information. After the positional adjustment, the wearing position determination unit 34 repeats the process from step S413 to determine whether or not the wearing position of the wearable article 10B is the correct position that is appropriate for authentication.

On the other hand, if it is determined that the wearing position is correct (step S413: Yes), the wearing position determination unit 34 outputs, to the authentication unit 35, a signal providing instructions to carry out the authentication process. Next, the authentication unit 35 performs the authentication process (step S415). The authentication unit 35 instructs the imaging unit 32 (light source 320 and TFT sensor 321) to capture an image. The authentication unit 35 obtains the authentication image captured by the imaging unit 32. The authentication unit 35 reads out, from the memory unit 38, each of a row of authentication images, in the insertion direction, including a vein pattern obtained by capturing images over a predetermined range on a legitimate user. The authentication unit 35 collates the respective authentication images with the image currently captured by the imaging unit 32. If the similarity between the currently captured image and any of the images among the authentication images is higher than a predetermined threshold value, then the authentication unit 35 determines that the authentication has succeeded. If the authentication succeeds (step S416: Yes), the processing flow ends. The authentication unit 35 outputs the authentication results to the control unit 15. Based on the authentication results, the control unit 15 enables the functions using various services making use of personal information stored in the memory unit 11. The user is then able to make use of payment services and the like using the wearable article 10B.

If the authentication fails (step S416: No), the authentication unit 35 transmits, to the display device 20B, via the communication unit 12, information indicating that the authentication has failed. In the display device 20B, the display control unit 21 displays, on the display unit 22, an error message such as: "Authentication failed. Will retry." (step S417). Next, the authentication unit 35 determines whether or not to retry the authentication process. For example, the authentication unit 35 reads out a preset number of retries from the memory unit 38, and compares the number of retries that has been read out with the number of times the authentication process has been performed since the user put on the wearable article 10B on the current occasion. If the number of times the authentication process has been performed is equal to or greater than the predetermined number of retries, then the authentication unit 35 determines that no further retries will be allowed (step S418: No) and the processing flow ends. The authentication unit 35 outputs the authentication results to the control unit 15. Based on the authentication results, the control unit 15 performs control to disable the functions using various services making use of personal information stored in the memory unit 11. The user then becomes unable to make use of payment services and the like using the wearable article 10B. Additionally, the authentication unit 35 transmits the authentication results to the display device 20B via the communication unit 12. In the display device 20B, the display control unit 21 displays, on the display unit 22, an error message such as: "Authentication failed."

If the number of times that the authentication process was performed is within the predetermined number of retries, then the authentication unit 35 determines that authentication will be retried (step S418: Yes), and instructs the wearing position determination unit 34 to retry the authentication. The wearing position determination unit 34 repeats the process from step S413.

Thus, according to the fifth exemplary embodiment, the imaging unit 32 stores authentication images corresponding to all circumferential directions at the position at which the user wears the wearable article 10. As a result thereof, the authentication unit 35 can perform vein authentication without requiring the rotation direction position of the wearable article 10 to be aligned.

Sixth Exemplary Embodiment

Herebelow, an authentication system according to a sixth exemplary embodiment of the present invention will be explained with reference to FIGS. 18 to 20.

Figure 18:
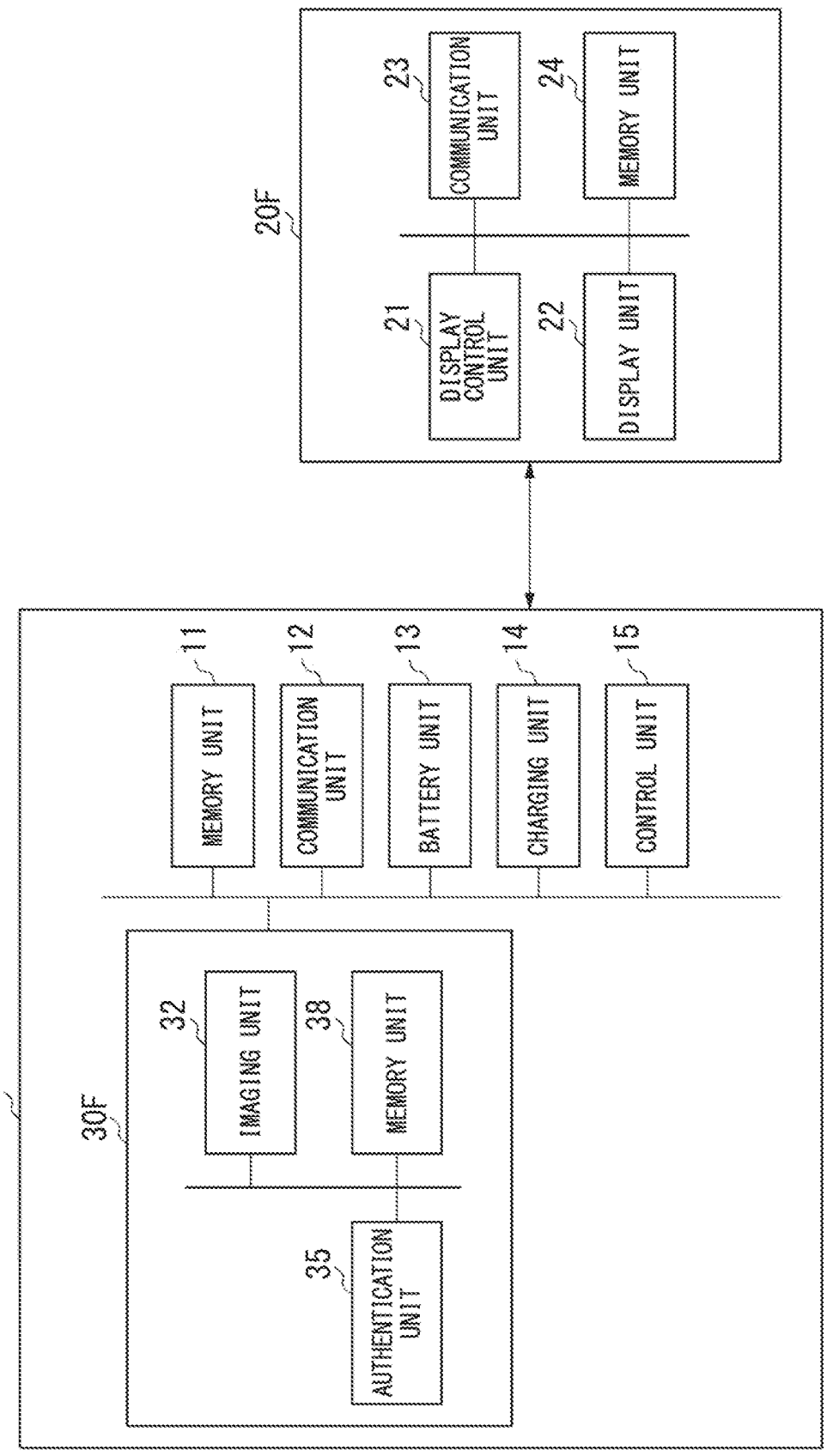
FIG. 18 is a diagram illustrating an example of an authentication system according to a sixth exemplary embodiment of the present invention.

FIG. 18 is a diagram illustrating an example of the authentication system according to the sixth exemplary embodiment of the present invention.

The authentication system according to the sixth exemplary embodiment of the present invention, as illustrated in FIG. 18, includes a wearable article 10F and a display device 20F. The wearable article 10F and the display device 20F are connected so as to be able to communicate with each other.

In the example illustrated in FIG. 18, the wearable article 10F includes a memory unit 11, a communication unit 12, a battery unit 13, a charging unit 14, a control unit 15 and an authentication device 30F. The authentication device 30F includes an imaging unit 32, an authentication unit 35 and a memory unit 38. The functional units of the authentication system according to the sixth exemplary embodiment will be explained by appending the same reference symbols for parts that are the same as those in the first exemplary embodiment. The wearable article 10F is, for example, a ring-type wearable terminal. The authentication device 30F of the sixth exemplary embodiment, unlike those of the first to fifth exemplary embodiments, has a structure in which a sensor or the like that is used to detect the wearing position is not provided.

The display device 20F includes a display control unit 21, a display unit 22, a communication unit 23 and a memory unit 24. The display control unit 21 displays, on the display unit 22, information to be presented to the user, based on information received by the communication unit 23. The display unit 22 is a display that is integrally combined with an element provided with an input function, such as a touch panel. The communication unit 23 communicates with the wearable article 10F. The memory unit 24 stores various types of information. The display device 20F is, for example, an electronic terminal such as a smartphone or a tablet terminal. The display device 20F displays authentication results or position determination results for the wearable article 10F. The user can adjust the wearing position of the wearable article 10F by referring to the information displayed by the display device 20F.

Figure 19:
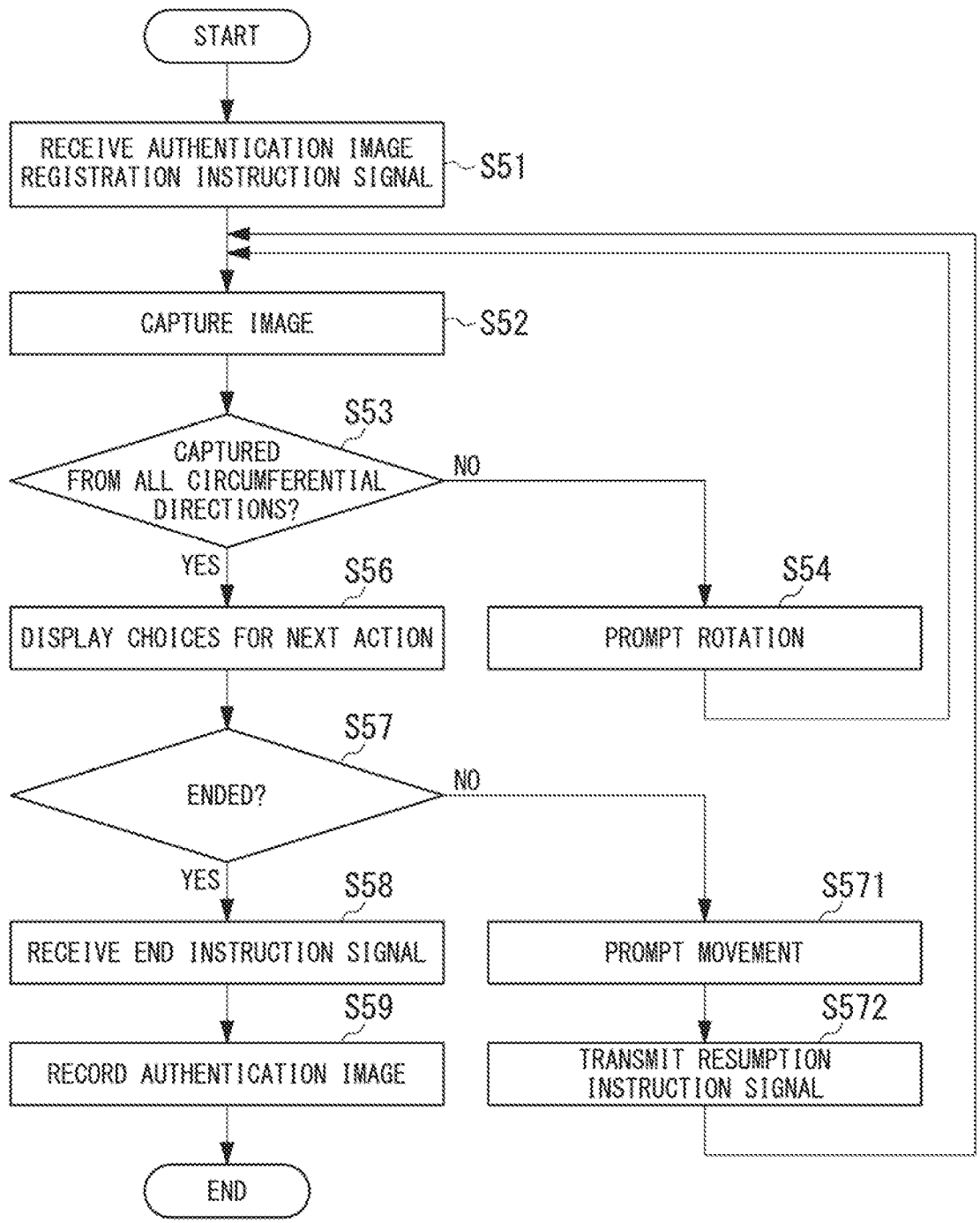
FIG. 19 is a flow chart illustrating an example of an authentication image registration method according to the sixth exemplary embodiment of the present invention.

FIG. 19 is a flow chart showing an example of the authentication image registration method in the sixth exemplary embodiment of the present invention.

First, the user performs a predetermined operation on the display unit 22 and causes the display unit 22 to display a screen for accepting instructions to register an authentication image. Additionally, the user wears the wearable article 10F at the position at which it is normally worn. Next, the user performs an operation on the display unit 22 providing instructions to start the registration of the authentication image. Then, the display unit 22 accepts the operation providing instructions to start the registration of the authentication image, and transmits a signal to the wearable article 10F, via the communication unit 23, providing instructions to register the authentication image. Additionally, the display unit 22 provides a display prompting the user to rotate the wearable article 10F. In the wearable article 10F, the communication unit 12 receives the authentication image registration instruction signal (step S51). The communication unit 12 outputs a registration instruction signal to the imaging unit 32. Next, the imaging unit 32 captures an authentication image (step S52). The authentication image is an image including a vein pattern at the position at which the user is wearing the wearable article 10F. Additionally, the user rotates the wearable article 10F in the circumferential direction of the finger while the imaging unit 32 captures the authentication image. Next, the imaging unit 32 determines whether or not images have been captured from all circumferential directions at the wearing position of the wearable article 10F (step S53). For example, the imaging unit 32 determines that the images have been captured from all circumferential directions upon capturing an image that is similar enough to be considered to be the same as an image captured immediately after the capturing of images was started. The images captured from all circumferential directions are not limited to being images taken omnidirectionally over 360°, and may, for example, be images captured from multiple angles turned 10° at a time. If the capturing of images from all circumferential directions is not completed (step S53: No), then the imaging unit 32 notifies the display device 20F, via the communication unit 12, that images have not been captured from all circumferential directions. In the display device 20F, the display control unit 21 displays, on the display unit 22, a message prompting the user to rotate the wearable article 10F in the circumferential direction of the finger, based on the notification (step S54). Then, the process from step S52 is repeated.

On the other hand, if it is determined, in step S53, that the capturing of the authentication images from all circumferential directions has been completed (step S53: Yes), then the imaging unit 32 notifies the display device 20F, via the communication unit 12, that the capturing of images from all circumferential directions has been completed. In the display device 20F, the display control unit 21 displays, on the display unit 22, choices for the next action to be taken, based on the notification (step S56). Specifically, the display unit 22 generates a display prompting the user to select whether to continue or to end the authentication image registration process. If the display unit 22 accepts an action, from the user, indicating that the registration process is to be continued (step S57: No), the display control unit 21 displays, on the display unit 22, a message prompting the user to move the wearable article 10F in the lateral direction (towards the base of the finger) (step S571). Additionally, the display control unit 21 also displays, on the display unit 22, an image for accepting an input operation of instructions to resume imaging. Seeing this display, the user moves the wearable article 10F towards the base of the finger. Next, after moving the wearable article 10F laterally, the user performs the input operation providing instructions to resume imaging. The display unit 22 accepts the input operation providing instructions to resume imaging, and transmits an imaging resumption instruction signal to the wearable article 10F, via the communication unit 23 (step S572). In the wearable article 10F, the communication unit 12 receives the resumption instruction signal and outputs the signal to the imaging unit 32. Then, the authentication system repeats the process from step S52.

If the display unit 22 accepts an input operation providing instructions to end the registration process, that is, if the display unit 22 accepts, from the user, an action choosing to end the registration process (step S57: Yes), the display unit 22 transmits an imaging end instruction signal to the wearable article 10F, via the communication unit 23 (step S58). In the wearable article 10F, the communication unit 12 receives the end instruction signal and outputs the signal to the imaging unit 32. The imaging unit 32 encrypts the captured authentication image and records the encrypted image in the memory unit 38 (step S59). At this time, the imaging unit 32 may record an authentication image captured from each direction. As a different method, the imaging unit 32 may record a three-dimensional image reconstructed from authentication images captured from all directions.

In the above-described explanation, the case in which the imaging unit 32 captures authentication images from all circumferential directions has been explained, but the present exemplary embodiment is not limited to such an example. For example, the imaging unit 32 may capture images over a rotational angle range of 180°, from the inside of the finger to the back of the finger.

As a result thereof, the imaging unit 32 stores authentication images covering the range over which the user can wear the wearable article 10.

Next, the authentication process in the sixth exemplary embodiment will be explained with reference to FIG. 20.

Figure 20:
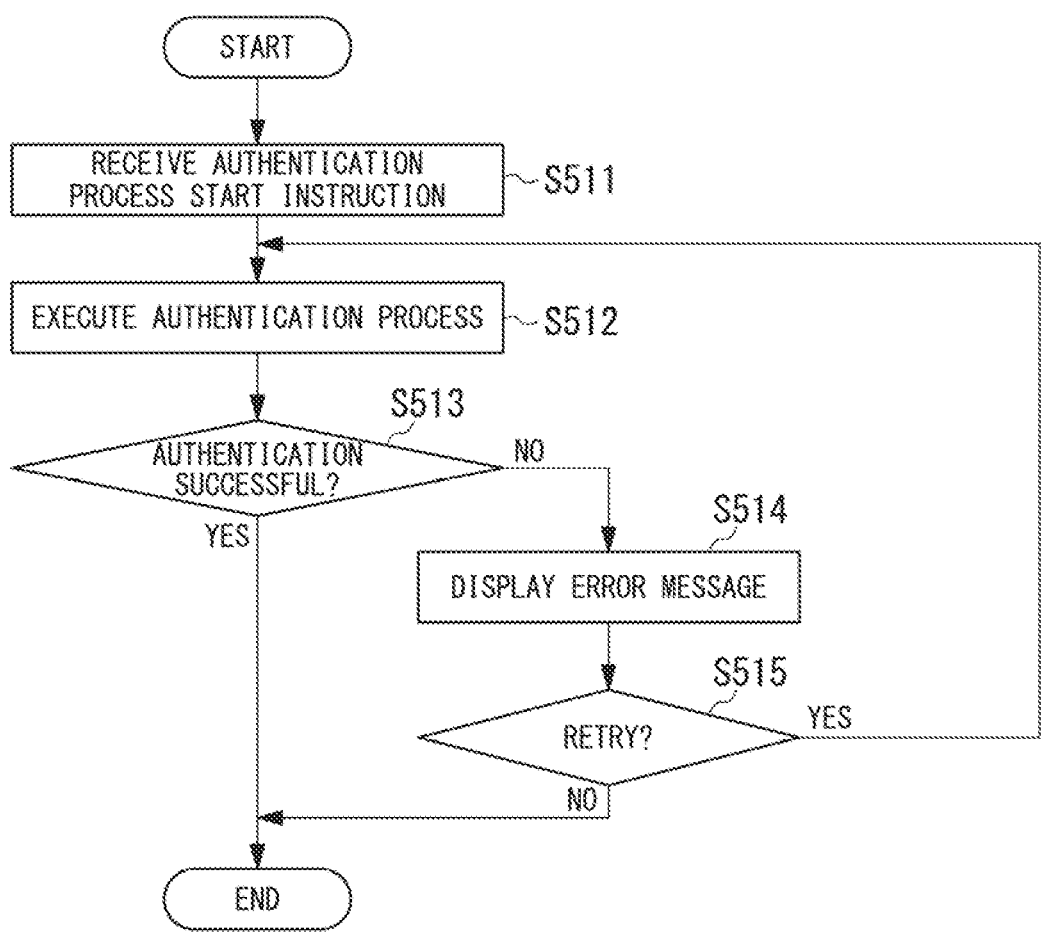
FIG. 20 is a flow chart illustrating an example of the authentication method according to the sixth exemplary embodiment of the present invention.

FIG. 20 is a flow chart illustrating an example of the authentication method according to the sixth exemplary embodiment of the present invention.

First, the user puts the wearable article 10F on the finger. Additionally, the user performs a predetermined operation on the display unit 22 and makes the display unit display a screen for accepting an authentication process start instruction. Next, the user performs an operation instructing the display unit 22 to start the authentication process. Then, the display unit 22 accepts the operation providing instructions to start the authentication process, and transmits to the wearable article 10F, via the communication unit 23, a signal providing instructions to start the authentication process. In the wearable article 10F, the communication unit 12 receives the signal providing instructions to start the authentication process. The communication unit 12 outputs the received signal to the authentication unit 35. Next, the authentication unit 35 performs the authentication process (step S512). The authentication unit 35 instructs the imaging unit 32 (light source 320 and TFT sensor 321) to capture an image. The authentication unit 35 obtains the authentication image captured by the imaging unit 32. The authentication unit 35 reads out, from the memory unit 38, authentication images covering the range over which the user can wear the wearable article 10, and collates the respective authentication images with the image currently captured by the imaging unit 32. If the similarity between the currently captured image and any of the images among the authentication images is higher than a predetermined threshold value, then the authentication unit 35 determines that the authentication has succeeded. If the authentication succeeds (step S513: Yes), the processing flow ends. The authentication unit 35 outputs the authentication results to the control unit 15. Based on the authentication results, the control unit 15 enables the functions using various services making use of personal information stored in the memory unit 11. The user is then able to make use of payment services and the like using the wearable article 10F.

If the authentication fails (step S513: No), the authentication unit 35 transmits, to the display device 20F, via the communication unit 12, information indicating that the authentication has failed. In the display device 20F, the display control unit 21 displays, on the display unit 22, an error message such as: "Authentication failed. Will retry." (step S514). Next, the authentication unit 35 determines whether or not to retry the authentication process. For example, the authentication unit 35 reads out a preset number of retries from the memory unit 38, and compares the number of retries that has been read out with the number of times the authentication process has been performed since the user put on the wearable article 10F on the current occasion. If the number of times the authentication process has been performed is equal to or greater than the predetermined number of retries, then the authentication unit 35 determines that no further retries will be allowed (step S515: No) and the processing flow ends. The authentication unit 35 outputs the authentication results to the control unit 15. Based on the authentication results, the control unit 15 performs control to disable the functions using various services making use of personal information stored in the memory unit 11. The user then becomes unable to make use of payment services and the like using the wearable article 10F. Additionally, the authentication unit 35 transmits the authentication results to the display device 20F via the communication unit 12. In the display device 20F, the display control unit 21 displays, on the display unit 22, an error message such as: "Authentication failed."

If the number of times the authentication process has been performed is within the predetermined number of retries, then the authentication unit 35 determines that the authentication should be retried (step S515: Yes), and the process from step S512 is repeated.

Thus, according to the sixth exemplary embodiment, the authentication unit 35 can perform the authentication without positioning the wearable article 10F.

Seventh Exemplary Embodiment

Herebelow, an authentication system according to a seventh exemplary embodiment of the present invention will be explained with reference to FIGS. 21 to 24.

Figure 21:
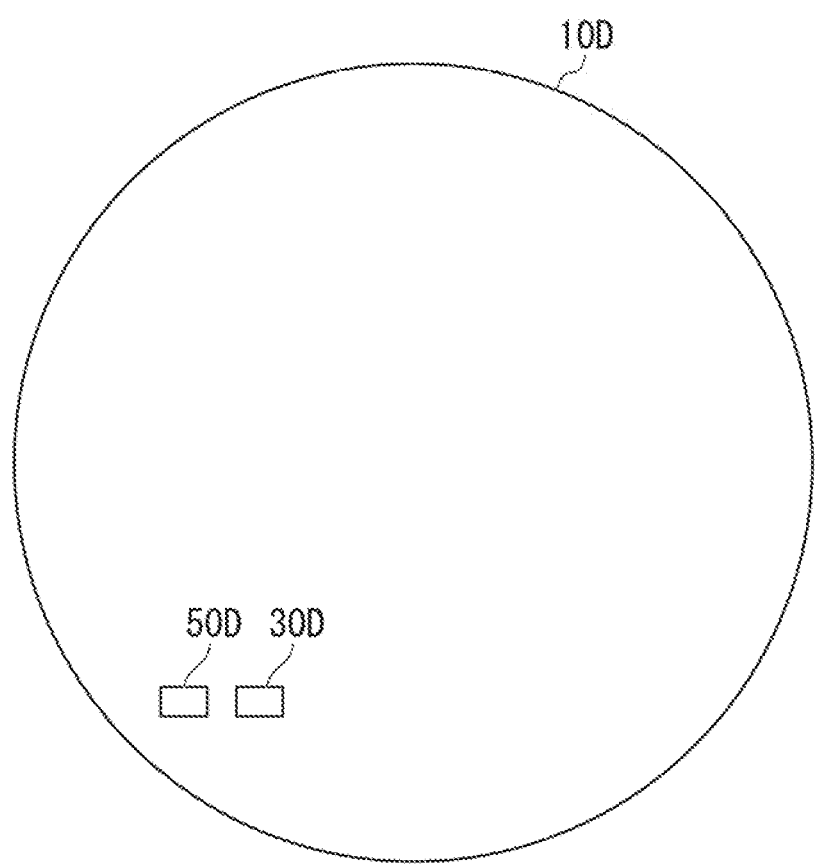
FIG. 21 is a diagram illustrating an example of a wearable article according to a seventh exemplary embodiment of the present invention.

FIG. 21 is a diagram illustrating an example of a wearable article according to the seventh exemplary embodiment of the present invention.

FIG. 21 shows a wearable article 10D (hereinafter referred to as contact lens 10D) which is a contact lens type wearable terminal. The contact lens 10D includes an authentication device 30D and a health state determination device 50D. When a user wears the contact lens 10D, the health state determination device 50D detects the components in the user's tears to determine the heath state or disease state of the user. The health state determination unit 50D includes a communication unit and transmits the determination results to an information processing device (not illustrated) that records the health state or disease state of the user, and the information processing device receives the determination results and records the results in a memory unit. The user is made aware of changes in the health state or the disease state on the basis of the recording of the determination results stored in the information processing device, and can make use of the results in health management. In this case, if a person other than a legitimate user wears the contact lens 10D, there is a possibility that information indicating a different person's health state will be mixed into the records in the information processing device. Therefore, the authentication device 30D determines whether or not a person who has worn the contact lens 10D is a legitimate user, by means of iris authentication.

The authentication device 30D, as in the case of the first exemplary embodiment, includes a position detection unit 31, an imaging unit 32, a wearing detection unit 33, a wearing position determination unit 34, an authentication unit 35, a display control unit 36, a display unit 37 and a memory unit 38. The imaging unit 32 includes a light source. A marker diagram is formed at a predetermined position on the surface of the contact lens 10D. This marker diagram emits light upon being struck by light from a light source. The marker diagram is formed, for example, from a fluorescent dye, a light guide, an LCD (liquid crystal display), an LED or the like. When the marker diagram is formed from a light guide, the entire marker diagram can be made to emit light when light from a light source strikes at least a portion of the marker diagram. When the marker diagram is formed from an LED, the marker diagram can be made to emit light even when not struck by light from a light source.

Figure 22:
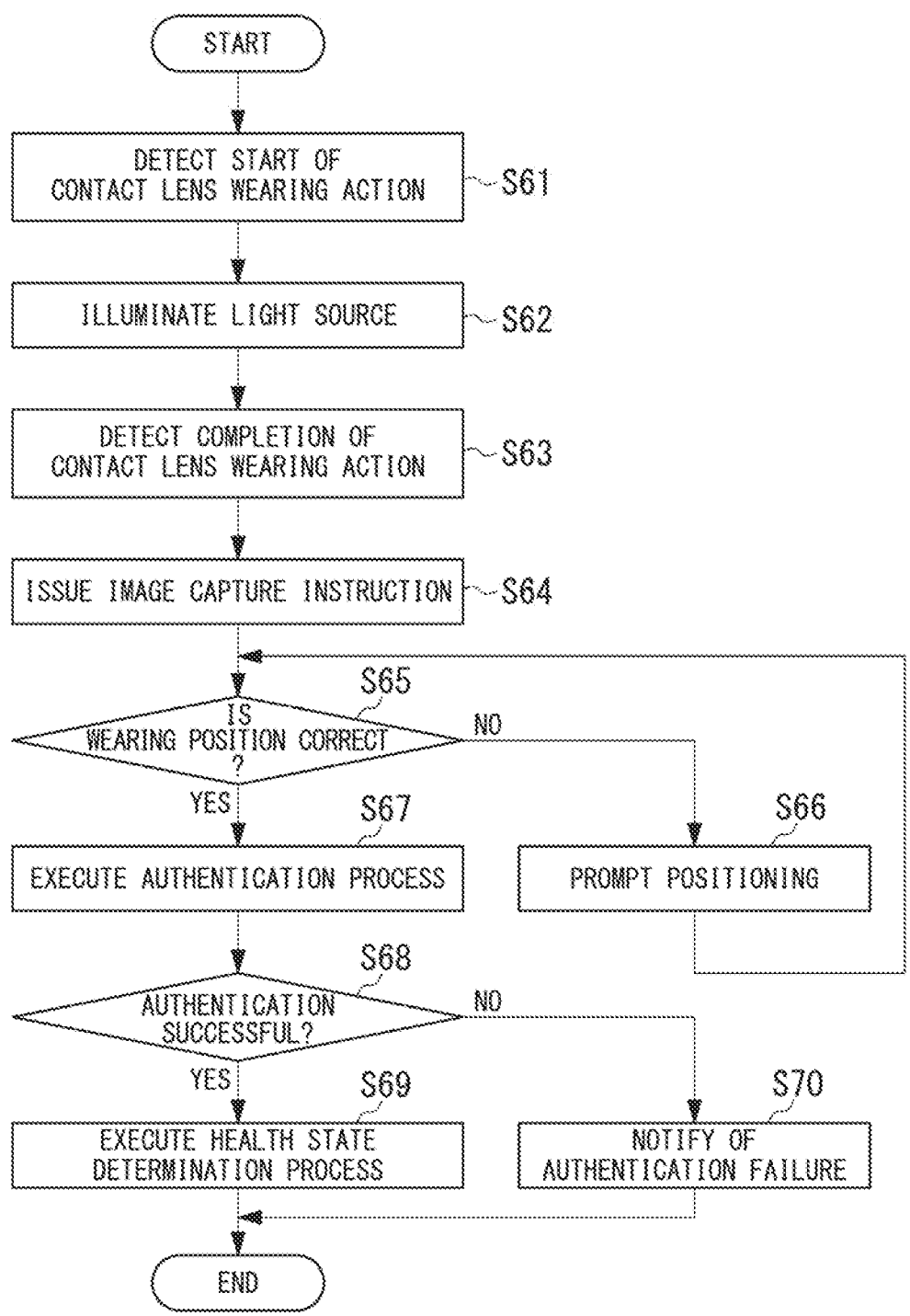
FIG. 22 is a flow chart illustrating an example of the authentication method according to the seventh exemplary embodiment of the present invention.

The functions of the seventh exemplary embodiment will be explained. FIG. 22 is a flow chart indicating an example of the authentication method according to the seventh exemplary embodiment of the present invention. When the user puts the contact lens 10D in the eye, the position detection unit 31 detects the starting of the contact lens 10D wearing action by receiving a signal from the health state determination device 50D detecting that the contact lens 10D has worn (step S61). The health state determination device 50D is able to detect that the wearing action has started, for example, by receiving signals indicating that the wearing action has started from an information processing device by means of an operation by a user (for example, pressing a wearing start button, not illustrated). The position detection unit 31, upon detecting the start of the wearing action, lights a light source provided in the imaging unit 32 for a predetermined period of time (e.g., a few seconds) (step S62). As a result thereof, the marker diagram applied to the surface of the contact lens 10D emits light, and the user is able to confirm the marker diagram by seeing the position of the emitted light. The user uses the position of the emitted light as a guide to position the contact lens 10D. When the positioning is completed, the information processing device transmits a signal indicating that the wearing action has been completed to the health state determination device 50D, by means of an operation by the user (for example, pushing a wearing completion button, not illustrated). As a result thereof, the health state determination device 50D is able to detect the completion of the wearing action. The wearing position determination unit 34 detects the completion of the contact lens 10D wearing action by receiving, from the health state determination device 50D, a signal indicating that the wearing of the contact lens 10D has been completed (step S63). The wearing position determination unit 34, upon detecting the completion of the wearing action, instructs the imaging unit 32 to capture an image of the user's eye (step S64). The imaging unit 32 then captures an image of the user's eye. The wearing position determination unit 34 uses this image to determine the wearing position of the contact lens 10D (step S65). For example, if the iris appears in the entirety of the captured image, then the wearing position determination unit 34 determines that the contact lens 10D is being worn at the position at which authentication is to be performed. If, for example, a portion other than the iris appears in the image, then the wearing position determination unit 34 determines that the wearing position of the contact lens is not the position at which authentication is to be performed. If it is determined that the position is not the position at which authentication is to be performed (step S65: No), then the wearing position determination unit 34 lights a light source provided in the imaging unit 32 for a predetermined period of time, and prompts the user to align the position (step S66). This process is repeated until the wearing position determination unit 34 determines that the wearing position is the position at which authentication is to be performed.

If it is determined that the wearing position is the position at which authentication is to be performed (step S65: Yes), then the wearing position determination unit 34 instructs the authentication unit 35 to start the authentication process. The authentication unit 35 performs iris authentication by collating the image captured by the imaging unit 32 with an iris image of a legitimate user that is prestored in the memory unit 38 (step S67). The authentication unit 35 outputs the results of the authentication to the health state determination device 50D. The health state determination device 50D determines whether or not the authentication has succeeded (step S68). If the authentication has succeeded (step S68: Yes), then the health state determination device 50D performs a user health state determination process (step S69). If the authentication has failed (step S68: No), then the health state determination device 50D notifies the above-mentioned information processing device that the authentication has failed (step S70). The information processing device displays that the authentication failed on the display unit and the user is made aware that the authentication failed.

Figure 23A:
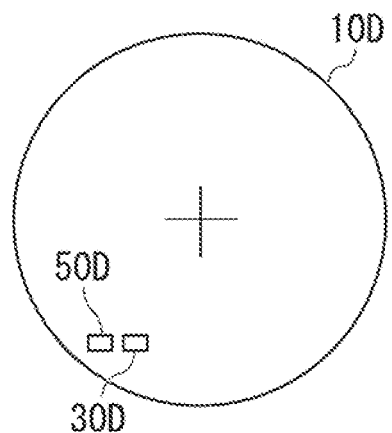
FIG. 23A is a diagram illustrating an example of a marker diagram for positioning according to the seventh exemplary embodiment of the present invention.
Figure 23B:
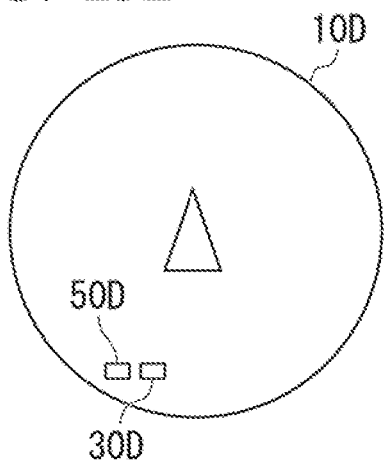
FIG. 23B is a diagram illustrating an example of a marker diagram for positioning according to the seventh exemplary embodiment of the present invention.
Figure 23C:
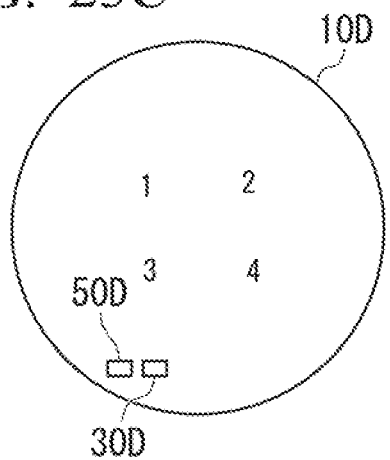
FIG. 23C is a diagram illustrating an example of a marker diagram for positioning according to the seventh exemplary embodiment of the present invention.

FIG. 23A to 23C are diagrams indicating examples of marker diagrams for positioning according to the seventh exemplary embodiment of the present invention.

FIG. 23A is an example of a case in which a cross-shaped marker diagram is provided near the center of the contact lens 10D. FIG. 23B is an example of a case in which an isosceles triangle marker diagram is provided near the center of the contact lens 10D. FIG. 23C is an example of a case in which numbers are arranged as marker diagrams at quartered sections of the contact lens 10D. The marker diagrams having the shapes and numbers indicated in the examples are formed by means of a fluorescent dye, a light guide, an LCD (liquid crystal display), an LED or the like, on the surface of the contact lens 10D. The marker diagrams receive light from a light source and emit light, thereby allowing them to be seen by a user. The user positions the contact lens 10D by using these marker diagrams as markers.

Figure 24:
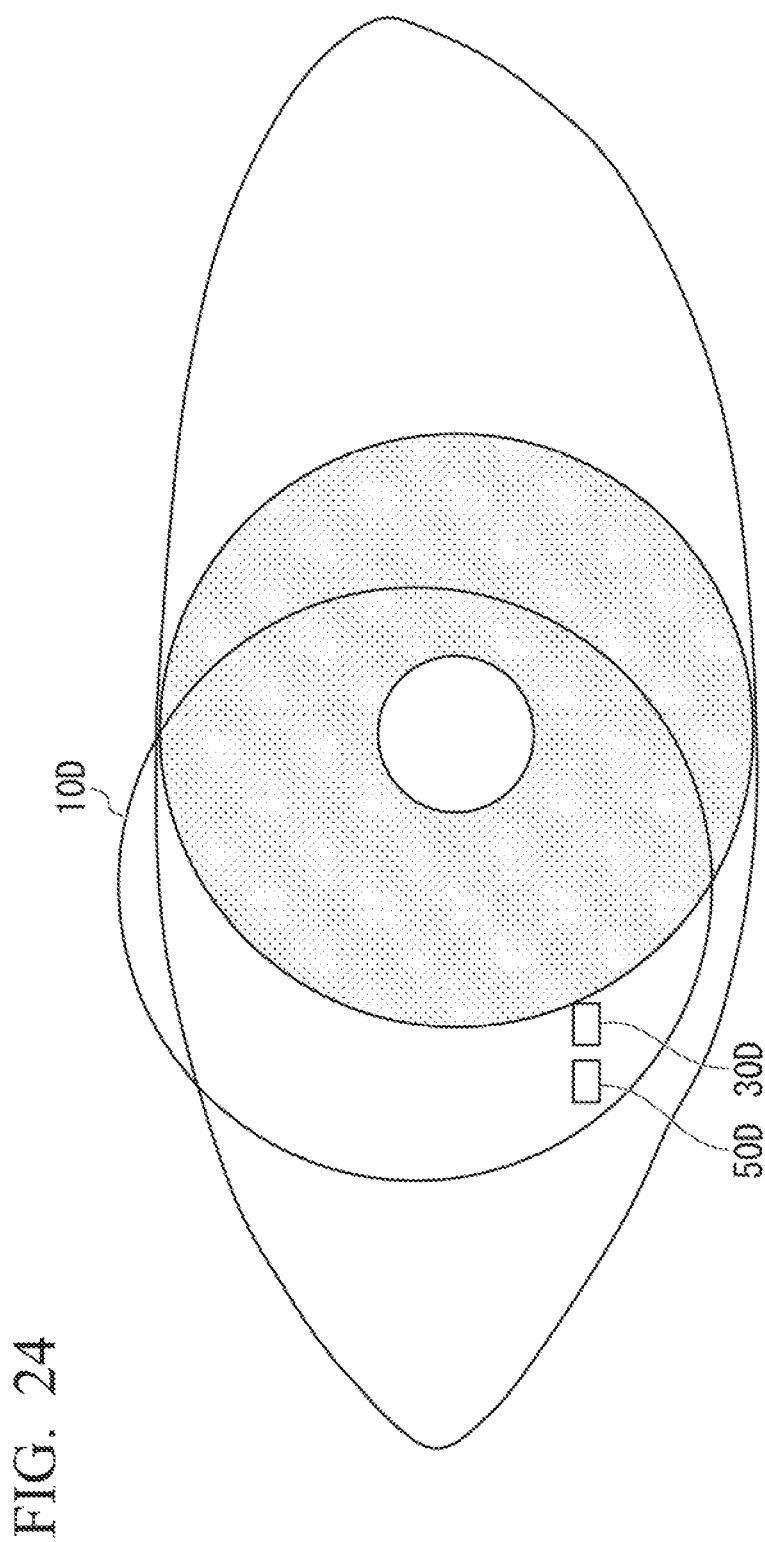
FIG. 24 is a diagram for explaining position determination according to the seventh exemplary embodiment of the present invention.

FIG. 24 is a diagram for explaining position determination according to the seventh exemplary embodiment of the present invention.

FIG. 24 is an example of a state in which the user is wearing the contact lens 10D. The case in which the imaging unit 32 captures an image of a portion of the user's eye corresponding to a positional range at which the authentication device 30D is arranged will be explained. In this case, when the contact lens 10D is worn at the position illustrated in FIG. 24, many portions other than the iris will appear in the image captured by the imaging unit 32. By comparing an image captured in this positional relationship with, for example, a pre-registered authentication image of the iris of a legitimate user, the wearing position determination unit 34 detects that the captured image includes portions that are not part of the iris. The wearing position determination unit 34 determines that the position of the contact lens 10D is not the position at which authentication is to be performed on the basis of this detection result.

According to the present exemplary embodiment, the authentication device 30D is able to determine whether or not the wearing position of the contact lens 10D is the position at which iris authentication is to be performed. Additionally, the authentication device 30D is able to prompt the user to align the wearing position of the contact lens 10D with the position of the user's iris (position at which authentication is to be performed). As a result thereof, the authentication device 30D is able to use iris authentication to authenticate whether a user who is wearing the contact lens 10D is a legitimate user.

Eighth Exemplary Embodiment

Herebelow, an authentication system according to an eighth exemplary embodiment of the present invention will be explained.

The structure of the authentication system according to the eighth exemplary embodiment is similar to the structure of the seventh exemplary embodiment.

The authentication system according to the eighth exemplary embodiment performs iris authentication without requiring the contact lens 10D to be positioned. Specifically, the memory unit 38 according to the eighth exemplary embodiment stores an image over the range that can be captured by the imaging unit 32 (e.g. an image of the iris around the entire circumference of the eyeball). The authentication unit 35 according to the eighth exemplary embodiment performs iris authentication by calculating the similarity between the image captured by the imaging unit 32 and a portion of the image stored in the memory unit 38.

Figure 25:
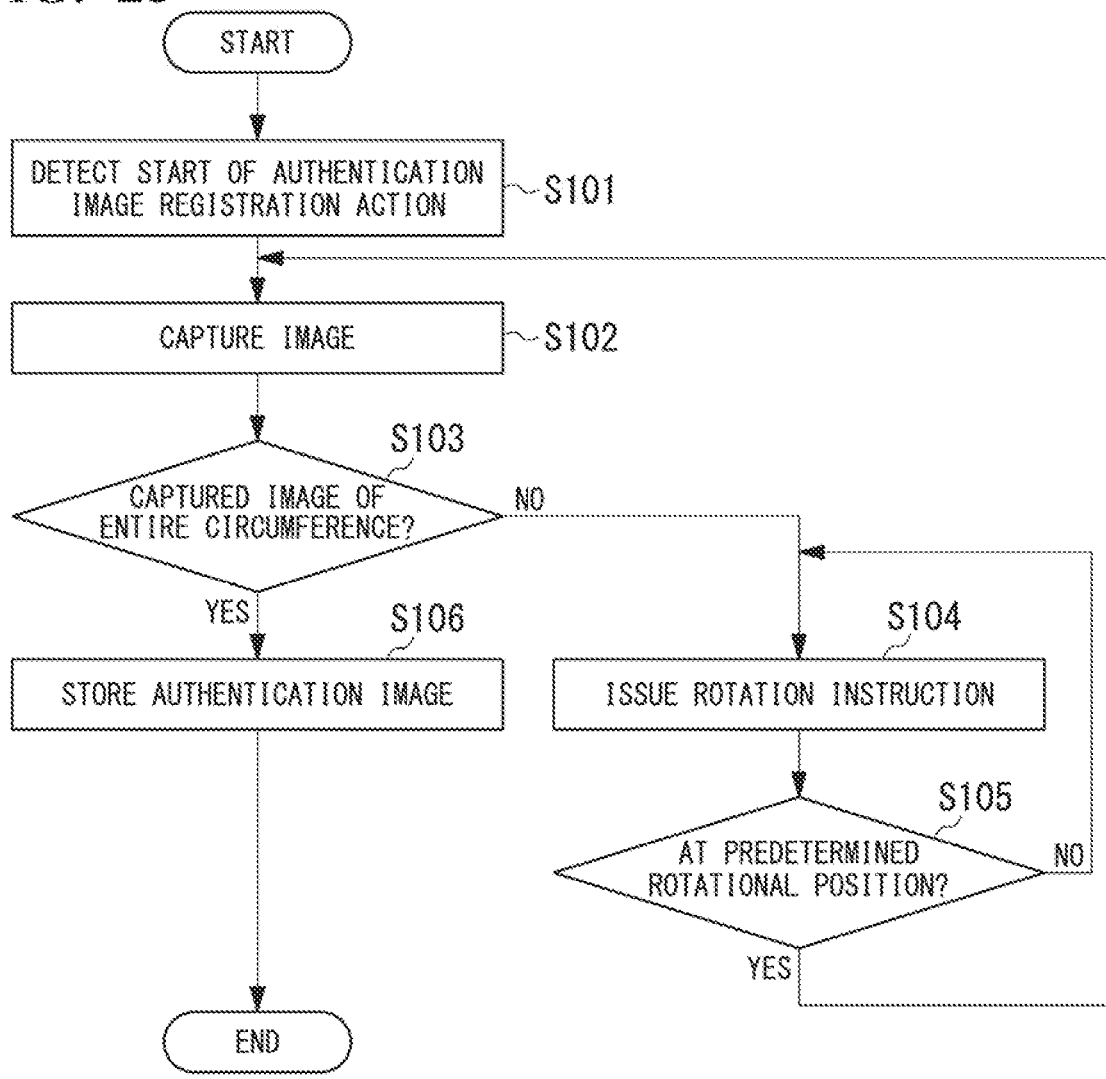
FIG. 25 is a flow chart illustrating an example of an iris image registration method according to an eighth exemplary embodiment of the present invention.

FIG. 25 is a flow chart showing an example of the registration method of the iris image in the seventh exemplary embodiment of the present invention. In this method, during the initial setup, an authentication image obtained by capturing images of the eyeball from all circumferential directions over a range, in the circumferential direction, centered about the pupil, is registered in the memory unit 38.

When the user wears the contact lens 10D, the position detection unit 31 receives a signal, from the health state determination device 50D, indicating that the wearing of the contact lens 10D has been detected, and thereby detects that the wearing action of the contact lens 10D has started (step S101). Upon detecting the starting of the wearing action, the position detection unit 31 instructs the imaging unit 32 to capture an image (step S102). The imaging unit 32 captures an image in which a portion of the user's eye appears. Next, the wearing position determination unit 34 determines whether or not the imaging unit 32 has completed the capturing of an image of the entire circumference centered on the user's pupil (step S103). The image of the entire circumference is not limited to being an image obtained by capturing images from all circumferential directions over 360° and, for example, may be images that are captured from multiple angles that are turned, for example, 10° at a time. If the capture of images over the entire circumference is not completed (step S103: No), the wearing position determination unit 34 lights the light source provided in the imaging unit 32 for a predetermined period of time and prompts the user to rotate the contact lens 10D (step S104). Next, based on an output from an acceleration sensor or a gyrosensor, not illustrated, the wearing position determination unit 34 determines whether or not the rotational position of the contact lens 10D is a position at which the capturing of images has not been completed (step S105). If the rotational position of the contact lens 10D is not a position at which the capturing of images has not been completed (step S105: No), the process returns to step S104, and the wearing position determination unit 34 prompts the user to rotate the contact lens 10D again. On the other hand, if the rotational position of the contact lens 10D is a position at which the capturing of images has not been completed (step S105: Yes), the process returns to step S102 and the imaging unit 32 is instructed to capture images.

On the other hand, if the capturing of images over the entire circumference has been completed in step S103 (step S103: Yes), then the memory unit 38 stores an authentication image obtained by combining the images captured in step S103 (step S106).

Thus, according to the eighth exemplary embodiment, the imaging unit 32 stores an authentication image over the range for which images can be captured. As a result thereof, the authentication unit 35 can perform iris authentication without positioning the contact lens 10D.

In another exemplary embodiment, instead of combining the images over the entire circumference, the memory unit 38 may store the images captured in step S103 directly as authentication images.

Ninth Exemplary Embodiment

Herebelow, an authentication system according to a ninth exemplary embodiment of the present invention will be explained.

The structure of the authentication system according to the ninth exemplary embodiment is the same as that in the eighth exemplary embodiment.

As with the eighth exemplary embodiment, the authentication system according to the ninth exemplary embodiment performs iris authentication without requiring the contact lens 10D to be positioned. Specifically, the memory unit 38 according to the ninth exemplary embodiment stores an image over the range that can be captured by the imaging unit 32 (e.g. an image of the iris around the entire circumference of the eyeball). The authentication unit 35 according to the eighth exemplary embodiment performs iris authentication by calculating the similarity between the image captured by the imaging unit 32 and a portion of the image stored in the memory unit 38.

Figure 26:
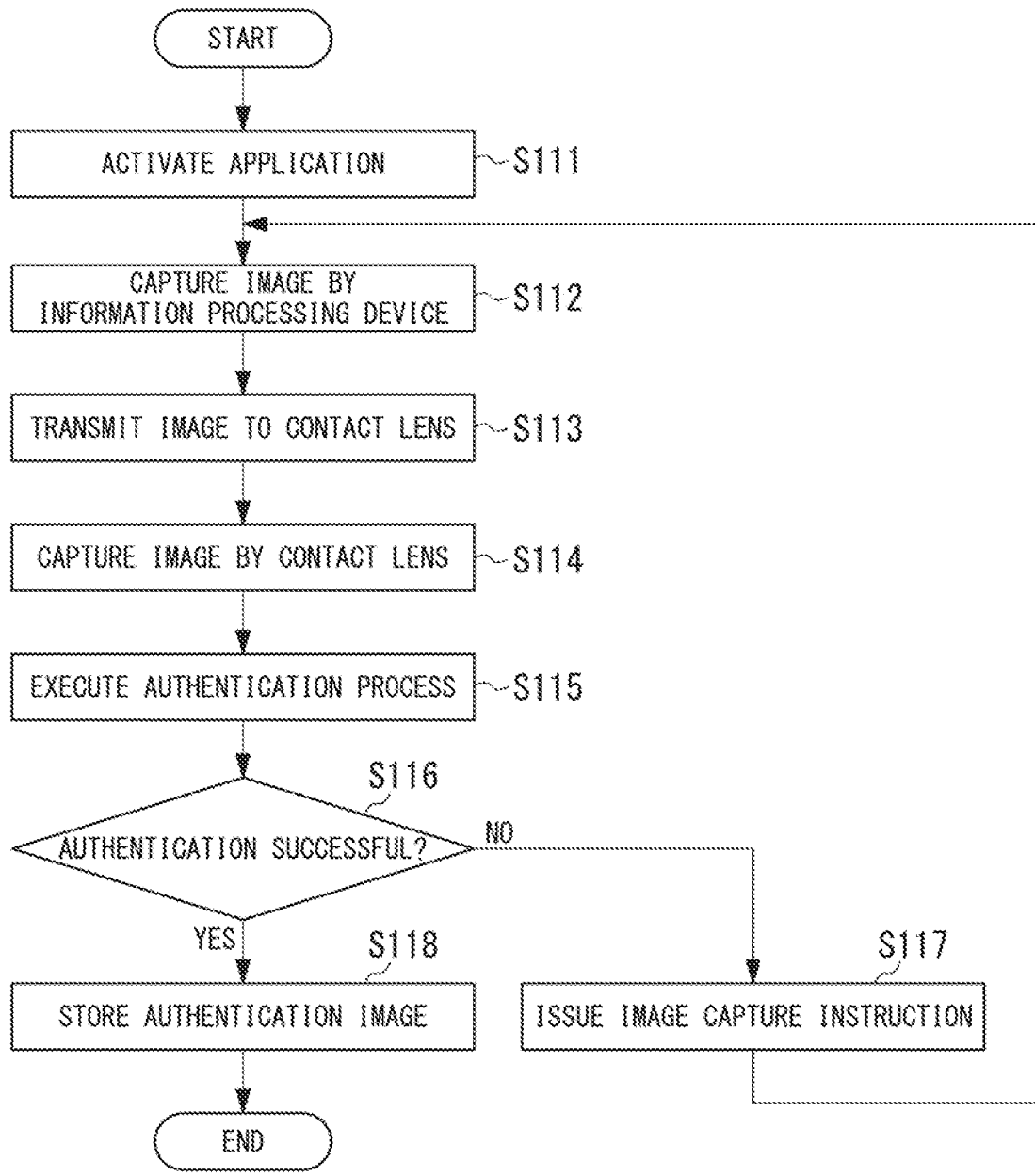
FIG. 26 is a flow chart illustrating an example of an iris image registration method according to a ninth exemplary embodiment of the present invention.

FIG. 26 is a flow chart showing an example of the iris image registration method according to the ninth exemplary embodiment of the present invention. In this method, an authentication image captured by the information processing device is registered in the memory unit 38.

The user operates an information processing device and activates a predetermined application program (step S111). At this time, the user is wearing the contact lens 10D. Next, the information processing device captures images of the user's eye by means of the imaging unit provided in the information processing device (step S112). Next, the information processing device transmits the captured image to the contact lens 10D (step S113).

When the contact lens 10D receives the image from the information processing device, the imaging unit 32 captures an image in which a portion of the user's eye appears (step S114). Next, the authentication unit 35 performs iris authentication by collating the image captured by the imaging unit 32 with the image received from the information processing device (step S115). The authentication unit 35 determines whether or not the authentication has succeeded (step S116). If the image captured by the imaging unit 32 and the image received from the information processing device are successfully collated, then this indicates that the image received from the information processing device can be used as an authentication image. On the other hand, if the collation between the image captured by the imaging unit 32 and the image received from the information processing device fails, then this indicates that the image received from the information processing device cannot be used as an authentication image.

If the authentication fails (step S116: No), the authentication unit 35 notifies the above-mentioned information processing device that the authentication failed. As a result thereof, the information processing device again displays an instruction to capture an image (step S117), the process returns to step S112, and an image in which the user's eye appears is captured again.

If the authentication succeeds (step S116: Yes), the authentication unit 35 records, in the memory unit 38, an authentication image received from the information processing device (step S118).

Thus, according to the ninth exemplary embodiment, the imaging unit 32 stores an authentication image over the range for which images can be captured. As a result thereof, the authentication unit 35 is able to perform iris authentication without requiring the contact lens 10D to be positioned.

In the present exemplary embodiment, it is determined whether or not an image captured by the information processing device is suitable as an authentication image by means of a determination by the authentication unit 35 as to whether or not the authentication has succeeded, but it is not limited thereto. For example, in another exemplary embodiment, it is possible to determine whether or not an image captured by the information processing device is suitable as an authentication image based on determinations of the spatial frequency or contrast of the image.

In another exemplary embodiment, it is not necessary for the contact lens 10D to be worn when capturing the image by means of the information processing device. In this case, the contact lens 10D performs the processing of step S114 and subsequent steps so as to determine whether or not the image captured by the information processing device is suitable as an authentication image after worn.

Tenth Exemplary Embodiment

Herebelow, an authentication system according to a tenth exemplary embodiment of the present invention will be explained.

Figure 27:
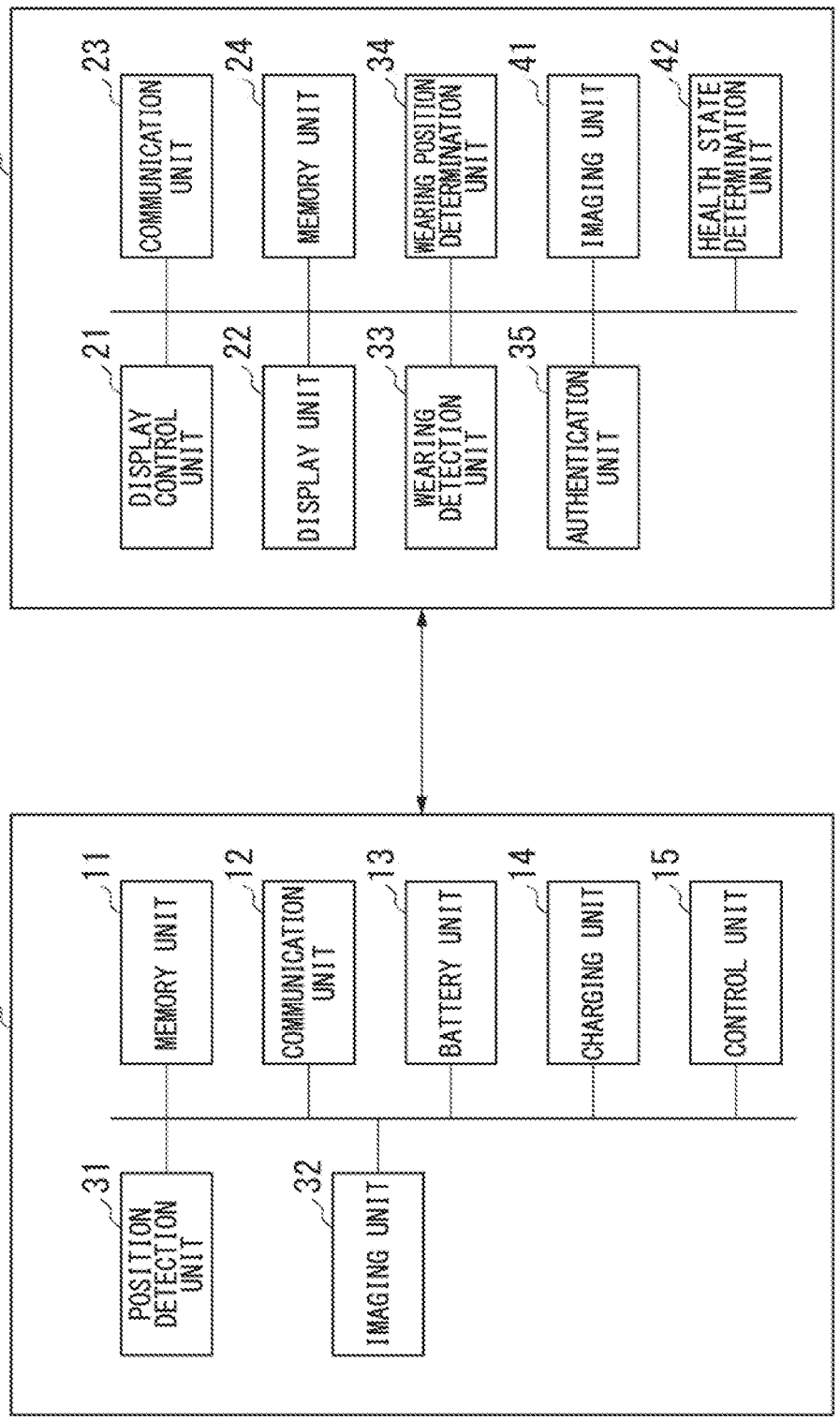
FIG. 27 is a diagram illustrating an example of an authentication system according to a tenth exemplary embodiment of the present invention.

FIG. 27 is a diagram illustrating an example of the authentication system according to the tenth exemplary embodiment of the present invention.

As illustrated in FIG. 27, the authentication system according to the present exemplary embodiment includes a wearable article 10E and an information processing device 20E. As in the seventh exemplary embodiment, the wearable article 10E (contact lens 10E) includes a memory unit 11, a communication unit 12, a battery unit 13, a charging unit 14, a control unit 15, a position detection unit 31 and an imaging unit 32.

As in the seventh exemplary embodiment, the information processing device 20E includes a display control unit 21, a display unit 22, a communication unit 23, a memory unit 24, a wearing detection unit 33, a wearing position detection unit 34 and an authentication unit 35. Additionally, the information processing device 20E further includes an imaging unit 41 and a health state determination unit 42. The imaging unit 41 is provided on the casing of the information processing device 20E, on a surface which is the same surface as that on which the display unit 22 is provided, and captures an image of the user facing the display unit 22. The health state determination unit 42 is a processing unit that performs the same processing as the health state determination unit 50D according to the seventh exemplary embodiment.

The authentication system according to the tenth exemplary embodiment assists in the positioning of the contact lens 10E by means of the information processing device 10E. The contact lens 10E according to the tenth exemplary embodiment does not have a marker diagram.

Figure 28:
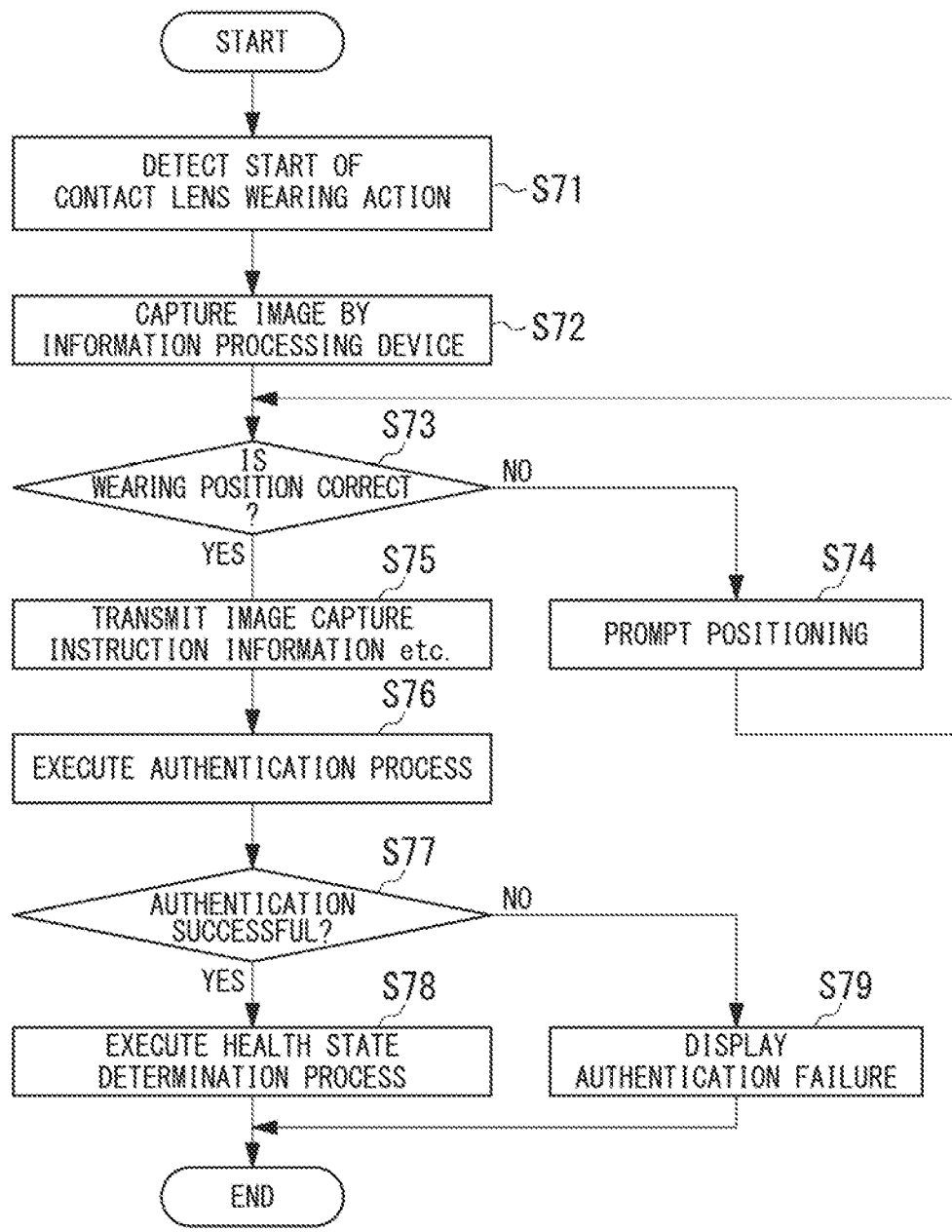
FIG. 28 is a flow chart illustrating an example of an authentication method according to a tenth exemplary embodiment of the present invention.

The functions of the tenth exemplary embodiment will be explained. FIG. 28 is a flow chart illustrating an example of the authentication method according to the tenth exemplary embodiment of the present invention. When the user puts in the contact lens 10E, the information processing device 20E detects the start of the wearing action, for example, by an operation by the user (e.g., pressing down a wearing start button, not illustrated) (step S71). At this time, the user holds the information processing device 20E so that the user's face faces the surface on which the display unit 22 is provided. When the information processing device 20E detects the start of the wearing action, the imaging unit 41 starts to capture an image (step S72). Since the imaging unit 41 is provided on the same surface as the display unit 22, the user's eye and the contact lens 10E appear in the image captured by the imaging unit 41.

The wearing position determination unit 34 determines whether or not the contact lens 10E is being worn at the position at which authentication is to be performed (step S73), based on the positions of predetermined circuits (for example, the memory unit 11, the communication unit 12, the battery unit 13, the charging unit 14, the control unit 15, the position detection unit 31 or the imaging unit 32), in the contact lens 10E, appearing in the image captured by the imaging unit 41. For example, if the predetermined circuits in the contact lens 10E appear at predetermined positions in the captured image, then the wearing position determination unit 34 determines that the contact lens 10E is being worn at the position at which authentication is to be performed. Additionally, for example, if the predetermined circuit in the contact lens 10E appears so as to be separated by at least a predetermined distance from the predetermined position in the captured image, then the wearing position determination unit 34 determines that the wearing position of the contact lens 10E is not the position at which authentication is to be performed. If the position is determined as not being the position at which authentication is to be performed (step S73: No), then the wearing position determination unit 34 displays, on the display unit 22, a screen prompting the user to position the contact lens 10E (step S74). The wearing position determination unit 34 repeats these processes until the wearing position determination unit 34 determines that the wearing position is the position at which authentication is to be performed. An example of a screen prompting the user to position the contact lens 10 includes the display of an arrow indicating the direction of rotation of the contact lens 10E.

If the position is determined to be the position at which authentication is to be performed (step S73: Yes), then the wearing position determination unit 34 transmits to the contact lens 10E, via the communication unit 23, image capture instruction information and captured image transmission instruction information (step S75). As a result thereof, the imaging unit 32 of the contact lens 10E captures an image of the user's eye and transmits the captured image to the information processing device 20E.

The wearing position determination unit 34 instructs the authentication unit 35 to start the authentication process. The authentication unit 35 performs iris authentication by collating the image captured by the imaging unit 32 with an iris image of a legitimate user that is prestored in the memory unit 38 (step S76). The authentication unit 35 outputs the authentication results to the health state determination unit 42. The health state determination unit 42 determines whether or not the authentication has succeeded (step S77). If the authentication has succeeded (step S77: Yes), then the health state determination unit 42 performs a user health state determination process (step S78). If the authentication fails (step S77: No), then the health state determination unit 42 displays that the authentication has failed on the display unit 22 (step S79). As a result thereof, the user is made aware that the authentication has failed.

According to the present exemplary embodiment, the information processing device 20E is capable of determining whether or not the contact lens 10E is being worn at the position at which iris authentication is to be performed. Additionally, the information processing device 20E is able to prompt the user to align the wearing position of the contact lens 10E with the position of the user's iris (position at which authentication is to be performed). As a result thereof, the information processing device 20E is able to authenticate whether a user wearing the contact lens 10E is a legitimate user by means of iris authentication.

Although the contact lens 10E according to the present exemplary embodiment does not have a marker diagram, it is not limited thereto. For example, in another exemplary embodiment, the contact lens 10E may have a marker diagram. In this case, the information processing device 20E determines the wearing position based on the angle of the marker diagram appearing in the image captured by the imaging unit 41.

Additionally, according to the present exemplary embodiment, the information processing device 20E performs the authentication process and the health state determination process, but it is not limited thereto. For example, in another exemplary embodiment, at least one of the authentication process and the health state determination process may be performed in the contact lens 10E, and the information processing device 20E may display the processing result thereof, as in the second exemplary embodiment.

According to the present exemplary embodiment, the information processing device 20E determines the wearing position of the contact lens 10E based on an image captured by the imaging unit 41, but it is not limited thereto. For example, in another exemplary embodiment, if the contact lens 10E is provided with an acceleration sensor, the information processing device 20E may determine the wearing position on the basis of the output from the acceleration sensor. In that case, the information processing device 20E specifies the wearing position of the contact lens 10 based on the direction of gravity detected by the acceleration sensor.

Eleventh Exemplary Embodiment

Herebelow, an authentication system according to an eleventh exemplary embodiment of the present invention will be explained.

Figure 29:
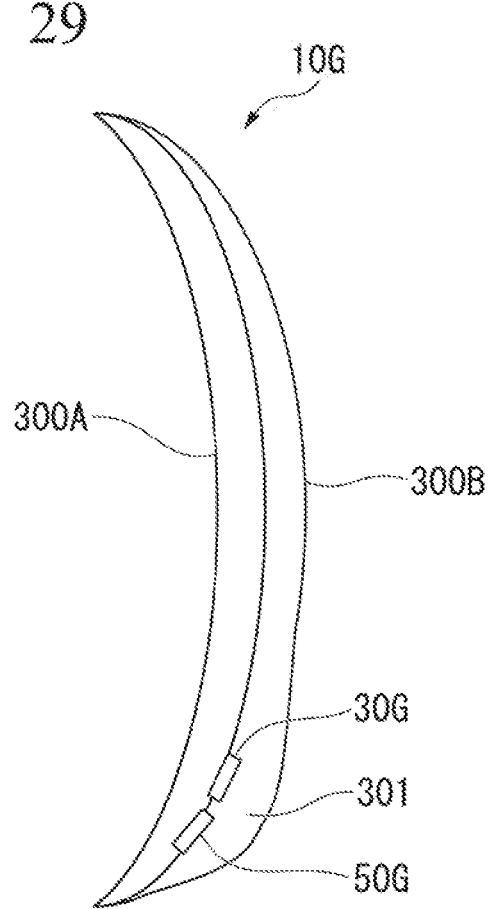
FIG. 29 is a section view illustrating an example of a wearable article according to an eleventh exemplary embodiment of the present invention.

FIG. 29 is a section view illustrating an example of a wearable article according to the eleventh exemplary embodiment of the present invention.

FIG. 29 illustrates a wearable article 10G (referred to as contact lens 10G), which is a contact lens type wearable terminal. The contact lens 10G has a laminated structure including a first-layer lens 300A and a second-layer lens 300B. The first-layer lens 300A forms a layer on a side that is worn over the user's eye. The second-layer lens 300B forms a layer on a side that contacts the outside air. The contact lens 10G further includes an authentication device 30G and a health state determination device 50G. The authentication device 30G and the health state determination device 50G are provided between the first-layer lens 300A and the second-layer lens 300B.

The contact lens 10G has a shape that is kept upright overall by means of gravity or blinking. Examples of shapes that are kept upright by gravity or by blinking include shapes having a thick portion 301 in a part of the contact lens 10G, such as a prism ballast shape or a double slab-off shape. Shapes that are kept upright by gravity or by blinking are generally used in contact lenses for astigmatism, and are normally not employed in normal contact lenses that do not require alignment of the rotation direction position.

A prism ballast shape is a shape in which the thickness of the contact lens 10G becomes gradually thicker from top to bottom. As a result thereof, each time the user blinks, the thicker side surface is pushed out and moved downward due to its own weight, thereby allowing the rotation direction position of the contact lens 10G to be held fixed. A double slab-off shape is a shape in which the upper and lower parts of the contact lens 10G are relatively thinner and the left and right parts are relatively thicker. As a result thereof, the upper and lower thin parts are pinched each time the user blinks, thereby allowing the rotational position of the contact lens 10G to be held fixed.

The authentication device 30G captures an image via the first-layer lens 300A. For this reason, the first-layer lens 300A is formed so as to have concentrically uniform thicknesses so that captured images are not distorted. Therefore, the thick portion 301 is included in the second-layer lens 300B. The authentication device 30G and the health state determination device 50G are provided on the inside of the thick portion 301 of the contact lens 10G, as shown in FIG. 29. As a result thereof, it is possible to make the overall thickness of the contact lens 10G thinner and to increase the amount of oxygen supplied to the cornea.

The authentication unit 35 starts the authentication process after the user blinks. As a result thereof, the authentication unit 35 is able to start the authentication process when, due to the blinking action, there is a high probability that the wearing position of the contact lens 10G is the position at which authentication is to be performed. Therefore, the authentication system according to the tenth exemplary embodiment does not need to be provided with a position detection unit 31 and a wearing position determination unit 34.

The above-mentioned authentication device 30 has a computer that is internal thereto. Additionally, the steps in the processes of the above-mentioned authentication device 30 are stored, in the form of a program, in a computer-readable recording medium, and the above-mentioned processes are performed by the computer reading and executing the program. In this case, a computer-readable recording medium refers to a magnetic disc, a magneto-optic disc, a CD-ROM, a DVD-ROM, a semiconductor memory device or the like. Additionally, the computer program may be transmitted to the computer over a communication line, and the computer may execute the program upon receiving this transmission.

The above-mentioned program may be for partially carrying out the above-mentioned functions. The above-mentioned program may be a so-called difference file (difference program) that is combined with a program that is already recorded in the computer system in order to carry out the above-mentioned functions.

All or some of the functions of the above-mentioned authentication device 30 may be carried out by utilizing hardware such as an ASIC (Application Specific Integrated Circuit), a PLD (Programmable Logic Device), an FPGA (Field-Programmable Gate Array) or the like.

In addition thereto, the features in the above-mentioned exemplary embodiments may be appropriately replaced with well-known features, within a range not departing from the scope of the present invention. Additionally, the technical scope of the invention is not limited to the above-mentioned exemplary embodiments, and various modifications may be made within a range not departing from the scope of the present invention.

All or some of the above-mentioned exemplary embodiments may be described as indicated in the following supplementary notes, but the invention is not to be construed as being limited to the following.

(Supplementary Note 1)

An authentication device comprising:

a wearing position determination unit that determines a wearing position, the wearing position being a position at which a wearable article comprising a sensor is being worn on a body; and an authentication unit that performs authentication by using biometric information of the body, the biometric information being detected by the sensor at the wearing position.

(Supplementary Note 2)

The authentication device according to supplementary note 1, further comprising:

a display unit that displays information regarding positional alignment between the wearable article and the body when the wearable article is being worn on the body.

(Supplementary Note 3)

The authentication device according to supplementary note 1 or 2, further comprising:

a wearing detection unit that detects that the wearable article has worn on the body, wherein the wearing position detection unit determines the wearing position when it is detected that the wearable article has worn on the body.

(Supplementary Note 4)

The authentication device according to any one of supplementary notes 1 to 3, wherein the sensor comprises an image sensor that obtains the biometric information by capturing an image of the body.

(Supplementary Note 5)

The authentication device according to any one of supplementary notes 1 to 4, wherein the wearable article comprises a finger ring having a ring shape, and the wearing position determination unit determines a wearing position of the finger ring based on a distance from a predetermined position on a finger on which the finger ring is being worn to the wearing position of the wearable article.

(Supplementary Note 6)

The authentication device according to any one of supplementary notes 1 to 4, wherein the wearable article comprises a finger ring having a ring shape, and the wearing position determination unit determines a wearing position of the finger ring based on a distance from an inner circumferential surface of the finger ring to a surface of a finger on which the finger ring is being worn, at a position at which the finger ring is being worn.

(Supplementary Note 7)

The authentication device according to any one of supplementary notes 1 to 3, wherein the wearable article comprises a finger ring having a ring shape, the sensor comprises an image sensor that captures an image at a position at which the finger ring is being worn, and the authentication unit performs vein authentication by collating an image captured by the image sensor with a pre-registered authentication image, the pre-registered authentication image comprising a vein pattern at a predetermined position of a finger on which the finger ring is being worn.

(Supplementary Note 8)

The authentication device according to any one of supplementary notes 1 to 3, wherein the wearable article comprises a finger ring having a ring shape, the sensor comprises an image sensor that captures an image at a position at which the finger ring is being worn, and the authentication unit performs vein authentication by collating the image captured by the image sensor with each of a plurality of pre-registered authentication images, the pre-registered authentication images comprising a vein pattern detected from each of a plurality of directions at a predetermined position of the finger on which the finger ring is being worn.

(Supplementary Note 9)

The authentication device according to any one of supplementary notes 1 to 3, wherein the wearable article comprises a contact lens, the sensor comprises an image sensor that obtains an image by capturing an image of the body, the wearing position determination unit determines a wearing position of the contact lens based on the image captured by the image sensor, and the authentication unit performs authentication by using an iris comprised in the image captured by the image sensor.

(Supplementary Note 10)

A wearable article comprising the authentication device according to any one of supplementary notes 1 to 4.

(Supplementary Note 11)

A finger ring comprising the authentication device according to any one of supplementary notes 5 to 8.

(Supplementary Note 12)

A contact lens comprising:

a surface that is coated with a fluorescent coating; and the authentication device according to supplementary note 9.

(Supplementary Note 13)

An authentication system comprising:

the authentication device according to any one of supplementary notes 1 to 9; and a display device that obtains, from the authentication device, information indicating the wearing position, and displays information for improving the wearing position based on the information indicating the wearing position.

(Supplementary Note 14)

An authentication system comprising:

a wearable article comprising a sensor that detects the biometric information; and an information processing device comprising the authentication device according to any one of supplementary notes 1 to 4.

(Supplementary Note 15)

An authentication method comprising:

determining a wearing position, the wearing position being a position at which a wearable article comprising a sensor is being worn on a body; and performing authentication by using biometric information of the body, the biometric information being detected by the sensor at the wearing position.

(Supplementary Note 16)

A program for causing a computer of an authentication device to execute:

determining a wearing position, the wearing position being a position at which a wearable article comprising a sensor is being worn on a body; and performing authentication by using biometric information of the body, the biometric information being detected by the sensor at the wearing position.

INDUSTRIAL APPLICABILITY

The present invention may be applied to an authentication device, an authentication system, an authentication method or a program.

REFERENCE SYMBOLS 10, 10B, 10C Wearable article
10A Ring

11 Memory unit
12 Communication unit
13 Battery unit
14 Charging unit
15 Control unit
20B Display device
20C Information processing device
30, 30B, 30C Authentication device
31 Position detection unit
32 Imaging unit
33 Wearing detection unit
34 Wearing position determination unit
35 Authentication unit
36 Display control unit
37 Display unit
38 Memory unit
310 Acceleration sensor
311A, 311B, 311C, 311D Electrostatic capacitive sensor
320 Light source
321 TFT sensor
370A, 370B, 370C LED lamp
40 Computation device
50D Health state determination device

The invention claimed is:

1. An authentication device comprising:
a ring;
a first sensor configured to acquire fingerprint information;
an authentication circuit configured to perform authentication based on fingerprint information stored in the ring and the acquired fingerprint information;
a controller configured to cause a function of the ring to be active based on a result of the authentication by the authentication circuit;
a second sensor configured to detect acceleration of the ring;
a plurality of third sensors, each configured to detect a distance to a finger inside the ring, the plurality of third sensors being provided on a circumference of the ring; and
a determination circuit configured to determine that the ring is positioned at an authentication position based on the acceleration detected by the second sensor and distances to the finger inside the ring detected by the plurality of third sensors,
wherein the authentication circuit is configured to perform the authentication when it is determined that the ring is positioned at the authentication position by the determination circuit.

2. The authentication device according to claim 1, wherein the first sensor is configured to acquire fingerprint information at the authentication position.

3. The authentication device according to claim 1, further comprising:
a second determination circuit configured to determine whether a user wearing the ring is an authorized user.

4. The authentication device according to claim 1, wherein the authentication circuit is configured to use the result of the authentication for personal identification.

5. The authentication device according to claim 1, further comprising:
a communication circuit configured to execute communication with an external device based on the result of the authentication.

6. The authentication device according to claim 5, wherein the controller is configured to control the communication circuit so that the communication circuit transmits personal information used for a payment service.

7. The authentication device according to claim 6, further comprising:
a memory configured to store the personal information used for the payment service.

8. The authentication device according to claim 6, wherein the controller is configured to cause use of the payment service to be invalid when a number of times that the authentication has been performed is equal to or more than a predetermined number.

9. The authentication device according to claim 1, further comprising:
a light configured to emit light based on the result of the authentication by the authentication circuit.

10. The authentication device according to claim 1, wherein the function of the ring includes permitting to enter or exit a secured room.

11. The authentication device according to claim 1, wherein the function of the ring includes permitting to use on a transit system.

12. An authentication method executed by an authentication device, the authentication device comprising a ring, the method comprising:
acquiring fingerprint information by a first sensor;
performing authentication based on fingerprint information stored in the ring and the acquired fingerprint information;
causing a function of the ring to be active based on a result of the authentication;
detecting acceleration of the ring by a second sensor;
detecting, by each of a plurality of third sensors, a distance to a finger inside the ring, the plurality of third sensors provided on a circumference of the ring; and
determining that the ring is positioned at an authentication position based on the detected acceleration detected by the second sensor and distances to the finger inside the ring detected by the plurality of third sensors,
wherein the authentication is performed when it is determined that the ring is positioned at the authentication position.

13. A non-transitory computer-readable recording medium storing a program for a computer of an authentication device, the authentication device comprising a ring, the program causing the computer to execute:
acquiring fingerprint information by a first sensor;
performing authentication based on fingerprint information stored in the ring and the acquired fingerprint information;
causing a function of the ring to be active based on a result of the authentication;
detecting acceleration of the ring by a second sensor;
detecting, by each of a plurality of third sensors, a distance to a finger inside the ring, the plurality of third sensors provided on a circumference of the ring; and
determining that the ring is positioned at an authentication position based on the detected acceleration detected by the second sensor and distances to the finger inside the ring detected by the plurality of third sensors,
wherein the authentication is performed when it is determined that the ring is positioned at the authentication position.

14. The authentication device according to claim 1, wherein
the second sensor is configured to detect the acceleration of the ring at predetermined intervals in time, and the determination circuit is configured to calculate a movement distance of the ring in a horizontal direction based on the acceleration detected at the predetermined intervals in time, and determine that the ring is positioned at the authentication position.

15. The authentication device according to claim 1, wherein
the determination circuit is configured to determine that the ring is positioned at the authentication position based on the acceleration detected by the second sensor, when a starting of a wearing action for wearing the ring on the finger is detected based on the distances to the finger inside the ring detected by the plurality of third sensors.

16. The authentication device according to claim 1, wherein
the determination circuit is configured to determine that the ring is positioned at the authentication position, on a basis of a movement distance of the ring in a horizontal direction based on the acceleration detected by the second sensor, and a position in a rotation direction based on a result of a comparison of the distances to the finger inside the ring detected by the plurality of third sensors.

17. The authentication device according to claim 1, wherein
the determination circuit is configured to determine that the ring is positioned at the authentication position based on the detected acceleration and a criteria value, and
wherein a tolerance range of the criteria value used for the determination is made narrower, when a retry of the authentication is performed due to a failure of the authentication.

* * * * *